United States Patent
Bolli et al.

(10) Patent No.: US 8,288,554 B2
(45) Date of Patent: Oct. 16, 2012

(54) PYRIDIN-3-YL DERIVATIVES AS IMMUNOMODULATING AGENTS

(75) Inventors: Martin Bolli, Allschwil (CH); David Lehmann, Galmiz (CH); Boris Mathys, Prattein (CH); Claus Mueller, Weil am Rhein (DE); Oliver Nayler, Arlesheim (CH); Beat Steiner, Dornach (CH); Jörg Velker, Huningue (FR)

(73) Assignee: Actelion Pharmaceuticals Ltd., Allschwil (CH)

( * ) Notice: Subject to any disclaimer, the term of this patent is extended or adjusted under 35 U.S.C. 154(b) by 65 days.

(21) Appl. No.: 12/310,763

(22) PCT Filed: Sep. 6, 2007

(86) PCT No.: PCT/IB2007/053593
§ 371 (c)(1),
(2), (4) Date: Mar. 3, 2010

(87) PCT Pub. No.: WO2008/029370
PCT Pub. Date: Mar. 13, 2008

(65) Prior Publication Data
US 2010/0168005 A1    Jul. 1, 2010

(30) Foreign Application Priority Data
Sep. 8, 2006 (WO) ................ PCT/IB2006/053187

(51) Int. Cl.
*C07D 417/00* (2006.01)
*C07D 413/04* (2006.01)
*A61K 31/44* (2006.01)

(52) U.S. Cl. .............. 546/268.7; 546/269.4; 514/341; 514/342

(58) Field of Classification Search ............... None
See application file for complete search history.

(56) References Cited

U.S. PATENT DOCUMENTS

| | | | |
|---|---|---|---|
| 3,647,809 A | 3/1972 | Reiter et al. | |
| 5,708,180 A | 1/1998 | Beck et al. | |
| 7,605,171 B2 * | 10/2009 | Colandrea et al. | 514/340 |
| 2004/0058894 A1 | 3/2004 | Doherty et al. | |
| 2007/0043104 A1 | 2/2007 | Luthman et al. | |
| 2007/0270438 A1 | 11/2007 | Bhattacharya et al. | |
| 2008/0064740 A1 | 3/2008 | Bolli et al. | |
| 2008/0176926 A1 | 7/2008 | Bolli et al. | |
| 2008/0194670 A1 | 8/2008 | Bolli et al. | |
| 2008/0249093 A1 | 10/2008 | Colandrea et al. | |
| 2008/0300294 A1 | 12/2008 | Bolli et al. | |
| 2008/0306124 A1 | 12/2008 | Albert et al. | |
| 2008/0318955 A1 | 12/2008 | Bolli et al. | |
| 2009/0005421 A1 | 1/2009 | Bolli et al. | |
| 2009/0275554 A1 | 11/2009 | Habashita et al. | |
| 2010/0048648 A1 | 2/2010 | Bolli et al. | |
| 2010/0063108 A1 | 3/2010 | Bolli et al. | |
| 2010/0075946 A1 | 3/2010 | Bolli et al. | |
| 2010/0084795 A1 | 4/2010 | Bolli et al. | |
| 2010/0087417 A1 | 4/2010 | Bolli et al. | |
| 2010/0087495 A1 | 4/2010 | Bolli et al. | |
| 2010/0234346 A1 | 9/2010 | Bolli et al. | |
| 2010/0240717 A1 | 9/2010 | Bolli et al. | |
| 2010/0261702 A1 | 10/2010 | Bolli et al. | |
| 2010/0331372 A1 | 12/2010 | Bolli et al. | |
| 2011/0028448 A1 | 2/2011 | Bolli et al. | |
| 2011/0028449 A1 | 2/2011 | Bolli et al. | |
| 2011/0046170 A1 | 2/2011 | Bolli et al. | |

FOREIGN PATENT DOCUMENTS

| | | |
|---|---|---|
| DE | 10237883 | 3/2004 |
| EP | 0476646 | 3/1992 |
| EP | 0702003 A2 | 6/1998 |
| EP | 1873153 | 1/2008 |
| JP | 2008120794 | 5/2008 |
| WO | WO91/15583 | 10/1991 |
| WO | WO99/46277 | 9/1999 |
| WO | WO 0045799 A2 * | 8/2000 |
| WO | WO 01/12627 | 2/2001 |
| WO | WO 02/068417 | 9/2002 |
| WO | WO03/062248 | 7/2003 |
| WO | WO 03/062252 | 7/2003 |
| WO | WO 03/105771 | 12/2003 |
| WO | WO2004/035538 | 4/2004 |
| WO | WO2004/056789 | 7/2004 |
| WO | WO2004/103279 | 12/2004 |
| WO | WO2005/014525 | 2/2005 |
| WO | WO2005/032465 | 4/2005 |
| WO | WO2005/058848 | 6/2005 |

(Continued)

OTHER PUBLICATIONS

Silverman, R. "The Organic Chemistry of Drug Design and Drug Action," 2004, Elsevier, pp. 29-32.*
Caplus 2000:553399.*
Patani, G. et al., Chem. Rev. 1996, vol. 96, pp. 3147-3176.*
Silverman, R. "The Organic Chemistry of Drug Design and Drug Action," 2004, Elsevier, p. 9.*
U.S. Appl. No. 12/310,801, Bolli, et al.
U.S. Appl. No. 12/673,918, Martin Bolli, et al.
Alvernhe et al; "Synthesis and Reactivity of 3-chloro-3-trifluoromethylacroleins: Stabilization of the Tetrahedral Intermediate in a Nucleophilic Vinylic "Substitution""; Bull. Soc. Chim. Fr.; 131, 1994, 167-172.

(Continued)

*Primary Examiner* — Janet Andres
*Assistant Examiner* — Heidi Reese
(74) *Attorney, Agent, or Firm* — Hoxie & Associates LLC

(57) ABSTRACT

The invention relates to pyridin-3-yl derivatives of Formula (I) wherein $R^1$, $R^2$, $R^3$, $R^4$, $R^5$; $R^6$ and A are as described in the description, their preparation and their use as pharmaceutically active compounds. Said compounds particularly act as immunomodulating agents.

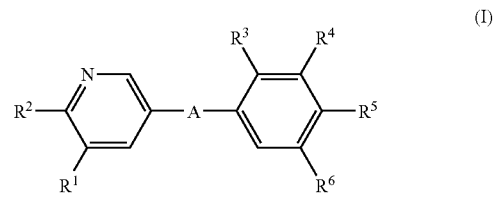

(I)

17 Claims, No Drawings

FOREIGN PATENT DOCUMENTS

| | | |
|---|---|---|
| WO | WO 2005/115382 | 12/2005 |
| WO | WO 2006/047195 | 5/2006 |
| WO | WO2006/100631 | 9/2006 |
| WO | WO2006/114400 | 11/2006 |
| WO | WO 2006/115188 | 11/2006 |
| WO | WO2006/131336 | 12/2006 |
| WO | WO2007/001973 | 1/2007 |
| WO | WO2007/085451 | 8/2007 |
| WO | WO 2007/098474 | 8/2007 |
| WO | WO 2007/132307 | 11/2007 |
| WO | WO2008/029370 | 3/2008 |
| WO | WO2008/035239 | 3/2008 |
| WO | WO2008/037476 | 4/2008 |
| WO | WO2008/076356 | 6/2008 |
| WO | WO2008/091967 | 7/2008 |
| WO | WO2008/114157 | 9/2008 |
| WO | WO2009/024905 | 2/2009 |
| WO | WO2009/057079 | 5/2009 |

OTHER PUBLICATIONS

Glennon et al; "B-Oxygenated Analogues of the 5-HT2A Serotonin Receptor Agonist 1-(4Bromo-2,5-dimethoxyphenyl)-2-aminopropane", Journal of Medicinal Chemistry, 2004, pp. 6034-6041, vol. 47.

Golub et al, "Molecular Classification of Cancer: Class Discovery and Class Prediction by Gene Expression Monitoring"; Science, 1999, vol. 286, 531-537.

Gronowitz et al; "On the Synthesis of Branched Saturated Fatty Acids"; Lipids, vol. 28, 1993, 889-897.

Knight et al; "Generation and Synthetic Utility of Dianions Derived from Thiophencarboxylic Acids"; J. Chem. Soc., Perkin Trans. 1; 1983; 791-794.

Lala et al; "Role of Nitric Oxide in Tumor Progression: Lessons From Experimental Tumors"; Cancer and Metastasis Reviews (1998), 17, 91-106.

Patani et al; "Bioisosterism: A Rational Approach in Drug Design"; Chem. Rev. 1996, vol. 96, No. 8, pp. 3147-3176.

Roth et al; "2-4-Diamino-5-benzylyrimidines and Analogs as Antibacterial Agents"; J. Med. Chem.; 1988; vol. 31, No. 1; pp. 122-129.

Tsukerman et al; "Basicity and Structure of .alpha., .beta.—unsaturated Ketones of a Heterocyclic Series. VII. Methyl-substituted Analogs of Chalcones"; Chemical Abstracts Service; XP002467039; STN Databse Accession No. 1971: 87024.

Wild et al; "Asymmetric Synthesis of (S)-(–)-acromelobic Acid"; Eur. J. Org. Chem.; 2003; pp. 4445-4440.

Zhen et al, "Discovery of Potent 3,5-Diphenyl-1,2,4-oxadiazole Sphingosine-l-phosphate-1(SIP1) Receptor Agonists with Exceptional Selectivity Against S1P2 and S1P", Journal of Medicinal Chemistry, 2005, pp. 6169-6173, vol. 48, No. 20.

HLA et al., An abundant transcript induced in differentiating human endothelial cells encodes a polypeptide with structural similarities to G-protein-coupled receptors, J. Biol. Chem. (1990) vol. 265, No. 16, pp. 9308-9313.

Gould, Salt selection for basic drugs, Int'l. J. Pharmaceutics (1986) vol. 33, pp. 201-217.

Gibson, Editor, Pharmaceutical Preformulation and Formulation, His Health Group, Englewood, CO, USA (2001).

Remington, The Science and Practice of Pharmacy, 20th Edition, Philadelphia College of Pharmacy and Science, 2003.

Mentzel et al., N-methoxy-N-methylamides (weinreb amides) in modern organic synthesis, J. Prakt. Chem. (1997) vol. 339, pp. 517-524.

Singh et al., The growing synthetic utility of weinreb's amide, J. Prakt. Chem. (2000) vol. 342, No. 4, pp. 340-347.

Khlestkin et al., Recent advances in the application of N,O-Dialkylhydroxylamines in organic chemistry, Current Organic Chemistry (2003) vol. 7, pp. 967-993.

Gangloff et al., Synthesis of 3,5-disubstituted-1,2,4-oxadiazoles using tetrabutylammonium fluoride as a mild and efficient catalyst, Tetrahedron Letters (2001) vol. 42, pp. 1441-1443.

Suzuki et al., Synthesis of the selective 5-hydroxytryptamine 4 ($5-HT_4$) receptor agonist (+)-(S)-2-chloro-5-methoxy-4-[5-(2-piperidylmethyl)-1,2,4-oxadiazol-3-yl]aniline, Chem. Pharm. Bull. (1999) vol. 47, No. 1, pp. 120-122.

Poulain et al., Parallel synthesis of 1,2,4-oxadiazoles from carboxylic acids using an improved, uranium-based, activation, Tetrahedron Letters (2001) vol. 42, pp. 1495-1498.

Srivastava et al., Synthesis of 3-aryl-5[thien-3-yl methyl]-1,2,4-oxadiazoles, Synthetic Comm. (1999) vol. 29, No. 9, pp. 1437-1450.

John et al., Reactions of (difluroramino) difluroacetonitrile and (difluroamino) difluoracetamidoxime, Inorg. Chem. (1988) vol. 27, pp. 3100-3104.

Hamze et al., Synthesis of various 3-substituted 1,2,4-oxadiazole-containing chiral $\beta^3$—and α-amino acides from Fmoc-protected aspartic acid, J. Org. Chem. (2003) vol. 68, pp. 7316-7321.

Brain et al., Novel procedure for the synthesis of 1,3,4-oxadiazoles from 1,2-diacylhydrazines using polymer-supported Burgess reagent under microwave conditions, Tetrahedron Letters (1999) vol. 40, pp. 3275-3278.

Ciu et al., Design and synthesis of highly constrained factor Xa inhibitors: amidine-substituted bis(benzoyl)-1[1,3]-diazepan-2-ones and bis(benzylidene)-bis(gem-dimethyl)cycloketones, Bioorg. Med. Chem. (2003) vol. 11, pp. 3379-3392.

Kaboudin et al., One-pot synthesis of 1,2,4-oxadiazoles mediated by microwave irradiation under solvent-free condition, Heterocycles (2003) vol. 60, No. 10, pp. 2287-2292.

Greene et al., Protective Groups in Organic Synthesis, 3rd Edition, Wiley, New York (1991).

Kocienski, Protecting Groups, Thieme Stuttgart (1994).

Garca et al., Synthesis, biological evaluation, and three-dimensional quantitative structure-activity relationship study of small-molecule positive modulators of adrenomedullin, J. Med. Chem. (2005) vol. 48, No. 12, pp. 4068-4075.

Kiryanov et al., Synthesis of 2-alkoxy-substituted thiophenes, 1,3-thiazoles, and related S-heterocycles via Lawesson's reagent-mediated cyclization under microwave irradiation: applications for liquid crystal synthesis, J. Org. Chem. (2001) vol. 66, No. 23, pp. 7925-7929.

Sato et al., Synthesis and evaluation of substituted 4-alkoxy-2-aminopyridines as novel neuropeptide Y1 receptor antagonists, Bioorg. & Med. Chem. Letters (2004) vol. 14, pp. 1761-1764.

La Mattina, The synthesis of 2-amino-4-(4-imidazoly)pyridines, J. Heterocyclic Chem. (1983) vol. 20, pp. 533-538.

Pesson et al., Antibacteriens de synthese—derives de l'acide pipemidique, Eur. J. Med. Chem. (1980) vol. 15, No. 3, pp. 263-268.

Furstner et al., Iron-catalyzed cross-coupling reactions, J. Am. Chem. Soc. (2002) vol. 124, No. 46, pp. 13856-13863.

Furstner et al., Iron-catalyzed cross-coupling reactions of alkyl-grignard reagents with aryl chlorides, tosylates, and triflates, Angew. Chem. (2002) vol. 41, No. 4, pp. 609-612.

Paine, A convenient synthesis of nicotinate esters from 3-cyanopyridones, J. Heterocyclic (1987) vol. 24, pp. 351-355.

Kerins et al., Generation of substituted sryrenes via Suzuki cross-coupling of aryl halides with 2,4,6-trivinylcyclotriboroxane, J. Org. Chem. (2002) vol. 67, No. 14, pp. 4968-4971.

Meyer et al., Synthesis of new 1,2,4- and 1,3,4-oxadiazole derivatives, Synthesis (2003), No. 6, pp. 899-905.

Trapani et al., Propofol analogues, J. Med. Chem. (1998) vol. 41, pp. 1846-1854.

Chakraborti et al., One-pot synthesis of nitriles from aldehydes under microwave irradiation: influence of the medium and mode of microwave irradiation on product formation. Tetrahedron (1999) vol. 55, pp. 13265-13268.

Ecke et al., ortho-Alkylation of aromatic amines, J. Org. Chem. (1957) vol. 22, pp. 639-642.

Xu et al., Acyclic analogues of adenosine bisphosphates as P2Y receptor antagonists: phosphate substitution leads to multiple pathways of inhibition of platelet aggregation, J. Med. Chem. (2002) vol. 45, pp. 5694-5709.

Yan et al., Discover of 3-arylpropionic acids as potent agonists of sphingosine-1-posphate receptor-1 ($S1P_1$) with high selectivity against all other known S1P receptor subtypes, Bioorg. Med. Chem. Letters (2006) vol. 16, pp. 3679-3683.

* cited by examiner

PYRIDIN-3-YL DERIVATIVES AS IMMUNOMODULATING AGENTS

CROSS REFERENCE TO RELATED APPLICATIONS

This application is a United States National Stage Application under 35 U.S.C. 371 of PCT/IB2007/053593 filed on Sep. 6, 2007, which claims the benefit of PCT/IB2006/053187 filed on Sep. 8, 2006, the contents of each of which are incorporated herein by reference in their entirety.

FIELD OF THE INVENTION

The present invention relates to S1P1/EDG1 receptor agonists of Formula (I) and their use as active ingredients in the preparation of pharmaceutical compositions. The invention also concerns related aspects including processes for the preparation of the compounds, pharmaceutical compositions containing a compound of the Formula (I), and their use as compounds improving vascular function and as immunomodulating agents, either alone or in combination with other active compounds or therapies. A further aspect of the invention relates to novel compounds of Formula (II) that serve as intermediates to prepare compounds of Formula (I).

BACKGROUND OF THE INVENTION

The human immune system is designed to defend the body against foreign micro-organisms and substances that cause infection or disease. Complex regulatory mechanisms ensure that the immune response is targeted against the intruding substance or organism and not against the host. In some cases, these control mechanisms are unregulated and autoimmune responses can develop. A consequence of the uncontrolled inflammatory response is severe organ, cell, tissue or joint damage. With current treatment, the whole immune system is usually suppressed and the body's ability to react to infections is also severely compromised. Typical drugs in this class include azathioprine, chlorambucil, cyclophosphamide, cyclosporin, or methotrexate. Corticosteroids which reduce inflammation and suppress the immune response, may cause side effects when used in long term treatment. Nonsteroidal anti-inflammatory drugs (NSAIDs) can reduce pain and inflammation, however, they exhibit considerable side effects. Alternative treatments include agents that activate or block cytokine signaling.

Orally active compounds with immunomodulating properties, without compromising immune responses and with reduced side effects would significantly improve current treatments of uncontrolled inflammatory disease.

In the field of organ transplantation the host immune response must be suppressed to prevent organ rejection. Organ transplant recipients can experience some rejection even when they are taking immunosuppressive drugs. Rejection occurs most frequently in the first few weeks after transplantation, but rejection episodes can also happen months or even years after transplantation. Combinations of up to three or four medications are commonly used to give maximum protection against rejection while minimizing side effects. Current standard drugs used to treat the rejection of transplanted organs interfere with discrete intracellular pathways in the activation of T-type or B-type white blood cells. Examples of such drugs are cyclosporin, daclizumab, basiliximab, everolimus, or FK506, which interfere with cytokine release or signaling; azathioprine or leflunomide, which inhibit nucleotide synthesis; or 15-deoxyspergualin, an inhibitor of leukocyte differentiation.

The beneficial effects of broad immunosuppressive therapies relate to their effects; however, the generalized immunosuppression which these drugs produce diminishes the immune system's defense against infection and malignancies. Furthermore, standard immunosuppressive drugs are often used at high dosages and can cause or accelerate organ damage.

DESCRIPTION OF THE INVENTION

The present invention provides novel compounds of Formula (I) that are agonists for the G protein-coupled receptor S1P1/EDG1 and have a powerful and long-lasting immunomodulating effect which is achieved by reducing the number of circulating and infiltrating T- and B-lymphocytes, without affecting their maturation, memory, or expansion. The reduction of circulating T-/B-lymphocytes as a result of S1P1/EDG1 agonism, possibly in combination with the observed improvement of endothelial cell layer function associated with S1P1/EDG1 activation, makes such compounds useful to treat uncontrolled inflammatory disease and to improve vascular functionality.

The compounds of the present invention can be utilized alone or in combination with standard drugs inhibiting T-cell activation, to provide a new immunomodulating therapy with a reduced propensity for infections when compared to standard immunosuppressive therapy. Furthermore, the compounds of the present invention can be used in combination with reduced dosages of traditional immunosuppressant therapies, to provide on the one hand effective immunomodulating activity, while on the other hand reducing end organ damage associated with higher doses of standard immunosuppressive drugs. The observation of improved endothelial cell layer function associated with S1P1/EDG1 activation provides additional benefits of compounds to improve vascular function.

The nucleotide sequence and the amino acid sequence for the human S1P1/EDG1 receptor are known in the art and are published in e.g.: Hla, T., and Maciag, T. *J. Biol. Chem.* 265 (1990), 9308-9313; WO 91/15583 published 17 Oct. 1991; WO 99/46277 published 16 Sep. 1999. The potency and efficacy of the compounds of Formula (I) are assessed using a GTPγS assay to determine $EC_{50}$ values and by measuring the circulating lymphocytes in the rat after oral administration, respectively (see in Examples).

The general terms used hereinbefore and hereinafter preferably have, within this disclosure, the following meanings, unless otherwise indicated:

Where the plural form is used for compounds, salts, pharmaceutical compositions, diseases and the like, this is intended to mean also a single compound, salt, or the like.

Any reference hereinbefore or hereinafter to a compound of Formula (I) is to be understood as referring also to salts, especially pharmaceutically acceptable salts, of a compound of Formula (I), as appropriate and expedient.

The term $C_{1-5}$-alkyl, alone or in combination with other groups, means saturated, branched or straight chain groups with one to five carbon atoms. Examples of $C_{1-5}$-alkyl groups are methyl, ethyl, n-propyl, iso-propyl, n-butyl, iso-butyl, n-pentyl, and iso-pentyl.

Likewise, the term $C_{1-4}$-alkyl, alone or in combination with other groups, means saturated, branched or straight chain groups with one to four carbon atoms. Examples of $C_{1-4}$-alkyl groups are methyl, ethyl, n-propyl, iso-propyl, n-butyl, and iso-butyl.

Likewise, the term $C_{1-3}$-alkyl, alone or in combination with other groups, means saturated, branched or straight chain groups with one to three carbon atoms and represents a methyl, ethyl, n-propyl, or iso-propyl group; preferred are methyl and ethyl.

Likewise, the term $C_{2-5}$-alkyl, alone or in combination with other groups, means saturated, branched or straight chain groups with two to five carbon atoms.

Likewise, the term $C_{2-4}$-alkyl, alone or in combination with other groups, means saturated, branched or straight chain groups with two to four carbon atoms. Examples of $C_{2-4}$-alkyl groups are ethyl, n-propyl, iso-propyl, n-butyl, and iso-butyl.

The term $C_{1-4}$-alkoxy, alone or in combination with other groups, means an R—O group, wherein R is a $C_{1-4}$-alkyl. Examples of $C_{1-4}$-alkoxy groups are methoxy, ethoxy, propoxy, iso-propoxy, and iso-butoxy, preferred are methoxy, ethoxy, propoxy, and iso-propoxy.

The term $C_{2-5}$-alkoxy, alone or in combination with other groups, means an R—O group, wherein R is a $C_{2-5}$-alkyl. Examples of $C_{2-5}$-alkoxy groups are ethoxy, propoxy, iso-propoxy, iso-butoxy, and iso-pentoxy.

The term halogen means fluoro, chloro, bromo or iodo, preferably fluoro or chloro, most preferably chloro.

Salts are preferably the pharmaceutically acceptable salts of the compounds of Formula (I).

The term "pharmaceutically acceptable salts" refers to non-toxic, inorganic or organic acid and/or base addition salts, Lit. e.g. "Salt selection for basic drugs", Int. J. Pharm. (1986), 33, 201-217.

The compounds of Formula (I) may contain one or more stereogenic or asymmetric centers, such as one or more asymmetric carbon atoms. Substituents at a double bond or a ring may be present in cis-(=Z-) or trans (=E-) form unless indicated otherwise. The compounds of Formula (I) may thus be present as mixtures of stereoisomers or preferably as pure stereoisomers. Mixtures of stereoisomers may be separated in a manner known to a person skilled in the art.

i) The invention relates to pyridin-3-yl derivatives of the Formula (I),

Formula (I)

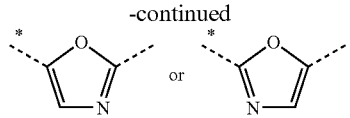

wherein

A represents *—CONH—$CH_2$—, *—CO—CH=CH—, *—CO—$CH_2CH_2$—,

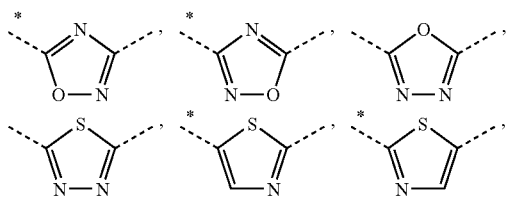

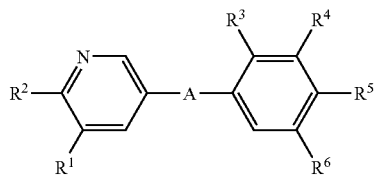

wherein the asterisks indicate the bond that is linked to the pyridine group of Formula (I);

$R^1$ represents hydrogen, $C_{1-4}$-alkyl, or chloro;

$R^2$ represents $C_{1-5}$-alkyl or $C_{1-4}$-alkoxy;

$R^3$ represents hydrogen, $C_{1-4}$-alkyl, $C_{1-4}$-alkoxy, or halogen;

$R^4$ represents hydrogen, $C_{1-4}$-alkyl, $C_{1-4}$-alkoxy, halogen, trifluoromethyl or trifluoromethoxy;

$R^5$ represents 2,3-dihydroxypropyl, di-(hydroxy-$C_{1-4}$-alkyl)-$C_{1-4}$-alkyl, —$CH_2$—$(CH_2)_k$—$NHSO_2R^{53}$, —$(CH_2)_n$CH(OH)—$CH_2$—$NHSO_2R^{53}$, —$CH_2$—$(CH_2)_k$—$NHCOR^{54}$, —$(CH_2)_n$CH(OH)—$CH_2$—$NHCOR^{54}$, —$CH_2$—$(CH_2)_n$—$CONR^{51}R^{52}$, —CO—$NHR^{51}$, 1-(3-carboxy-azetidinyl)-2-acetyl, 1-(2-carboxy-pyrrolidinyl)-2-acetyl, 1-(3-carboxy-pyrrolidinyl)-2-acetyl, 1-(3-carboxy-azetidinyl)-3-propionyl, 1-(2-carboxy-pyrrolidinyl)-3-propionyl, 1-(3-carboxy-pyrrolidinyl)-3-propionyl, —$(CH_2)_n$CH(OH)—$CH_2$—$NR^{51}R^{52}$, hydroxy, hydroxy-$C_{2-5}$-alkoxy, di-(hydroxy-$C_{1-4}$-alkyl)-$C_{1-4}$-alkoxy, 2,3-dihydroxy-propoxy, 2-hydroxy-3-methoxy-propoxy, —$OCH_2$—$(CH_2)_m$—$NR^{51}R^{52}$, 2-[(azetidine-3-carboxylic acid)-1-yl]-ethoxy, 2-[(azetidine-3-carboxylic acid $C_{1-5}$-alkylester)-1-yl]-ethoxy, 2-[(pyrrolidine-3-carboxylic acid)-1-yl]-ethoxy, 2-[(pyrrolidine-3-carboxylic acid $C_{1-5}$-alkylester)-1-yl]-ethoxy, —$OCH_2$—CH(OH)—$CH_2$—$NR^{51}R^{52}$, 3-[(azetidine-3-carboxylic acid)-1-yl]-2-hydroxypropoxy, 3-[(azetidine-3-carboxylic acid $C_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid $C_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid $C_{1-5}$-alkylester)-1-yl]-propoxy, —$OCH_2$—$(CH_2)_m$—$NHSO_2R^{53}$, —$OCH_2$—CH(OH)—$CH_2$—$NHSO_2R^{53}$, —$OCH_2$—$(CH_2)_m$—$NHCOR^{54}$, —$OCH_2$—CH(OH)—$CH_2$—$NHCOR^{54}$;

$R^{51}$ represents hydrogen, $C_{1-3}$-alkyl, 2-hydroxyethyl, 2-hydroxy-1-hydroxymethyl-ethyl, 2,3-dihydroxypropyl, carboxymethyl, 1-($C_{1-5}$-alkylcarboxy)methyl, 2-carboxyethyl, or 2-($C_{1-5}$-alkylcarboxy)ethyl;

$R^{52}$ represents hydrogen, methyl, or ethyl;

$R^{53}$ represents $C_{1-3}$-alkyl, methylamino, ethylamino, or dimethylamino;

$R^{54}$ represents hydroxymethyl, hydroxyethyl, aminomethyl, methylaminomethyl, dimethylaminomethyl, aminoethyl, 2-methylamino-ethyl, or 2-dimethylamino-ethyl;

k represents the integer 1, 2, or 3;

m represents the integer 1 or 2;

n represents 0, 1, or 2; and $R^6$ represents hydrogen, $C_{1-4}$-alkyl or halogen.

ii) Another embodiment of the invention relates to pyridin-3-yl derivatives according to embodiment i), wherein A represents -continued

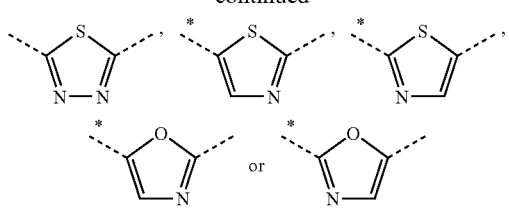

wherein the asterisks indicate the bond that is linked to the pyridine group of Formula (I).

iii) Another embodiment of the invention relates to pyridin-3-yl derivatives according to embodiment i), wherein A represents

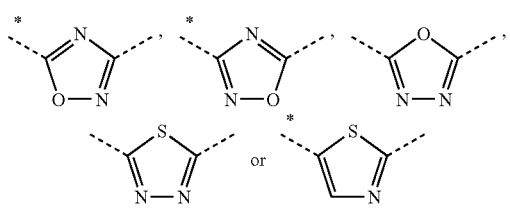

wherein the asterisks indicate the bond that is linked to the pyridine group of Formula (I).

iv) Another embodiment of the invention relates to pyridin-3-yl derivatives according to embodiment i), wherein A represents

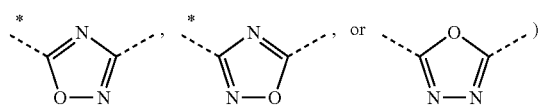

(especially A represents

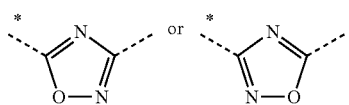)

wherein the asterisks indicate the bond that is linked to the pyridine group of Formula (I).

v) Another embodiment of the invention relates to pyridin-3-yl derivatives according to embodiment i), wherein A represents

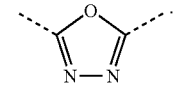

wherein the asterisks indicate the bond that is linked to the pyridine group of Formula (I).

vi) Another embodiment of the invention relates to pyridin-3-yl derivatives according to embodiment i), wherein A represents

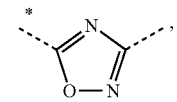

wherein the asterisk indicates the bond that is linked to the pyridine group of Formula (I).

vii) Another embodiment of the invention relates to pyridin-3-yl derivatives according to embodiment i), wherein A represents viii) Another embodiment of the invention relates to pyridin-3-yl derivatives according to any one of the embodiments i) to vii), wherein $R^1$ represents $C_{1-4}$-alkyl or chloro.

ix) Another embodiment of the invention relates to pyridin-3-yl derivatives according to any one of the embodiments i) to vii), wherein $R^1$ represents $C_{1-4}$-alkyl.

x) Another embodiment of the invention relates to pyridin-3-yl derivatives according to any one of the embodiments i) to vi), wherein $R^1$ represents methyl or ethyl.

xi) Another embodiment of the invention relates to pyridin-3-yl derivatives according to any one of the embodiments i) to vi), wherein $R^1$ represents methyl.

xii) Another embodiment of the invention relates to pyridin-3-yl derivatives according to any one of the embodiments i) to xi), wherein $R^2$ represents $C_{1-5}$-alkyl.

xiii) Another embodiment of the invention relates to pyridin-3-yl derivatives according to any one of the embodiments i) to xi), wherein $R^2$ represents $C_{2-4}$-alkyl.

xiv) Another embodiment of the invention relates to pyridin-3-yl derivatives according to any one of the embodiments i) to xi), wherein $R^2$ represents ethyl, n-propyl, iso-propyl, or iso-butyl.

xv) Another embodiment of the invention relates to pyridin-3-yl derivatives according to any one of the embodiments i) to xi), wherein $R^2$ represents n-propyl, or iso-butyl.

xvi) Another embodiment of the invention relates to pyridin-3-yl derivatives according to any one of the embodiments i) to xi), wherein $R^2$ represents $C_{1-4}$-alkoxy.

xvii) Another embodiment of the invention relates to pyridin-3-yl derivatives according to any one of the embodiments i) to xvi), wherein at least one of $R^3$, $R^4$ and $R^6$ represents a group other than hydrogen.

xviii) Another embodiment of the invention relates to pyridin-3-yl derivatives according to any one of the embodiments i) to xvi), wherein $R^3$ represents methyl or methoxy (especially methoxy), and $R^4$ and $R^6$ represent hydrogen.

xix) Another embodiment of the invention relates to pyridin-3-yl derivatives according to any one of the embodiments i) to xvi), wherein $R^3$ represents hydrogen.

xx) Another embodiment of the invention relates to pyridin-3-yl derivatives according to any one of the embodiments i) to xvi), wherein $R^3$ represents hydrogen; and $R^4$ represents $C_{1-4}$-alkyl, or $C_{1-4}$-alkoxy; and $R^6$ represents $C_{1-4}$-alkyl, or halogen.

xxi) Another embodiment of the invention relates to pyridin-3-yl derivatives according to any one of the embodiments i) to xvi), wherein $R^3$ represents hydrogen, $R^4$ represents $C_{1-3}$-alkyl, or methoxy (especially methyl, ethyl, or methoxy), and $R^6$ represents methyl, ethyl, or halogen (especially chloro).

xxii) Another embodiment of the invention relates to pyridin-3-yl derivatives according to any one of the embodiments i) to xvi), wherein $R^3$ represents hydrogen, and $R^4$ and $R^6$ represent a methyl group.

xxiii) Another embodiment of the invention relates to pyridin-3-yl derivatives according to any one of the embodiments i) to xvi), wherein $R^3$ represents hydrogen, $R^4$ represents a methyl group, and $R^6$ represents an ethyl group.

xxiv) Another embodiment of the invention relates to pyridin-3-yl derivatives according to any one of the embodiments i) to xvi), wherein $R^3$ represents hydrogen, $R^4$ represents a methoxy group, and $R^6$ represents chloro.

xxv) Another embodiment of the invention relates to pyridin-3-yl derivatives according to any one of the embodiments i) to xvi), wherein $R^3$ represents hydrogen, $R^4$ represents a methyl group, and $R^6$ represents chloro.

xxvi) Another embodiment of the invention relates to pyridin-3-yl derivatives according to any one of the embodiments i) to xxv), wherein $R^5$ represents 2,3-dihydroxypropyl, di-(hydroxy-$C_{1-4}$-alkyl)-$C_{1-4}$-alkyl, —$CH_2$—$(CH_2)_k$—$NHSO_2R^{53}$, —$(CH_2)_n CH(OH)$—$CH_2$—$NHSO_2R^{53}$, —$CH_2$—$(CH_2)_k$—$NHCOR^{54}$, —$(CH_2)_n CH(OH)$—$CH_2$—$NHCOR^{54}$, —$CH_2$—$(CH_2)_n$—$CONR^{51}R^{52}$, —$CO$—$NHR^{51}$, —$(CH_2)_n CH(OH)$—$CH_2$—$NR^{51}R^{52}$, hydroxy, hydroxy-$C_{2-5}$-alkoxy, di-(hydroxy-$C_{1-4}$-alkyl)-$C_{1-4}$-alkoxy, 2,3-dihydroxy-propoxy, 2-hydroxy-3-methoxy-propoxy, —$OCH_2$—$(CH_2)_m$—$NR^{51}R^{52}$, —$OCH_2$—$CH(OH)$—$CH_2$—$NR^{51}R^{52}$, —$OCH_2$—$(CH_2)_m$—$NHSO_2R^{53}$, —$OCH_2$—$CH(OH)$—$CH_2$—$NHSO_2R^{53}$, —$OCH_2$—$(CH_2)_m$—$NHCOR^{54}$, or —$OCH_2$—$CH(OH)$—$CH_2$—$NHCOR^{54}$.

xxvii) Another embodiment of the invention relates to pyridin-3-yl derivatives according to any one of the embodiments i) to xxv), wherein $R^5$ represents 2,3-dihydroxypropyl, —$CH_2$—$(CH_2)_k$—$NR^{51}R^{52}$, —$CH_2$—$(CH_2)_k$—$NHCOR^{54}$, —$(CH_2)_n CH(OH)$—$CH_2$—$NHCOR^{54}$, —$CH_2$—$(CH_2)_n$—$CONR^{51}R^{52}$, —$CO$—$NHR^{51}$, —$(CH_2)_n CH(OH)$—$CH_2$—$NR^{51}R^{52}$, hydroxy-$C_{2-5}$-alkoxy, di-(hydroxy-$C_{1-4}$-alkyl)-$C_{1-4}$-alkoxy, 2,3-dihydroxy-propoxy, 2-hydroxy-3-methoxy-propoxy, —$OCH_2$—$(CH_2)_m$—$NR^{51}R^{52}$, —$OCH_2$—$CH(OH)$—$CH_2$—$NR^{51}R^{52}$, —$OCH_2$—$(CH_2)_m$—$NHCOR^{54}$, or —$OCH_2$—$CH(OH)$—$CH_2$—$NHCOR^{54}$ (especially $R^5$ represents 2,3-dihydroxypropyl, —$CH_2$—$(CH_2)_k$—$NR^{51}R^{52}$, —$CH_2$—$(CH_2)_k$—$NHCOR^{54}$, —$(CH_2)_n CH(OH)$—$CH_2$—$NHCOR^{54}$, —$CH_2$—$(CH_2)_n$—$CONR^{51}R^{52}$, —$(CH_2)_n CH(OH)$—$CH_2$—$NR^{51}R^{52}$, hydroxy-$C_{2-5}$-alkoxy, di-(hydroxy-$C_{1-4}$-alkyl)-$C_{1-4}$-alkoxy, 2,3-dihydroxy-propoxy, 2-hydroxy-3-methoxy-propoxy, —$OCH_2$—$(CH_2)_m$—$NR^{51}R^{52}$, —$OCH_2$—$CH(OH)$—$CH_2$—$NR^{51}R^{52}$, —$OCH_2$—$(CH_2)_m$—$NHCOR^{54}$, or —$OCH_2$—$CH(OH)$—$CH_2$—$NHCOR^{54}$).

xxviii) Another embodiment of the invention relates to pyridin-3-yl derivatives according to any one of the embodiments i) to xxv), wherein $R^5$ represents hydroxy-$C_{2-5}$-alkoxy, di-(hydroxy-$C_{1-4}$-alkyl)-$C_{1-4}$-alkoxy, 2,3-dihydroxy-propoxy, —$OCH_2$—$(CH_2)_m$—$NR^{51}R^{52}$, —$OCH_2$—$CH(OH)$—$CH_2$—$NR^{51}R^{52}$, —$OCH_2$—$(CH_2)_m$—$NHCOR^{54}$, or —$OCH_2$—$CH(OH)$—$CH_2$—$NHCOR^{54}$.

xxix) Another embodiment of the invention relates to pyridin-3-yl derivatives according to any one of the embodiments i) to xxv), wherein $R^5$ represents 3-hydroxy-2-hydroxymethyl-propoxy, 2,3-dihydroxy-propoxy, or —$OCH_2$—$CH(OH)$—$CH_2$—$NHCOR^{54}$ (especially $R^5$ represents 2,3-dihydroxy-propoxy or —$OCH_2$—$CH(OH)$—$CH_2$—$NHCOR^{54}$, wherein $R^{54}$ represents hydroxymethyl).

xxx) Another embodiment of the invention relates to pyridin-3-yl derivatives according to any one of the embodiments i) to xxv), wherein $R^5$ represents —$OCH_2$—$CH(OH)$—$CH_2$—$NHCOR^{54}$, wherein $R^{54}$ represents hydroxymethyl.

xxxi) Another embodiment of the invention relates to pyridin-3-yl derivatives according to any one of the embodiments i) to xxv), wherein $R^5$ represents 2,3-dihydroxy-propoxy.

xxxii) Another embodiment of the invention relates to pyridin-3-yl derivatives according to embodiment i), wherein
A represents

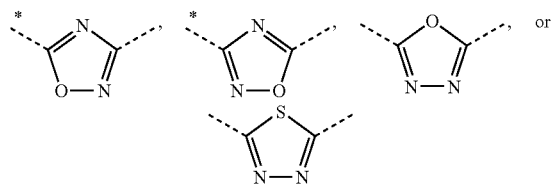

(especially A represents

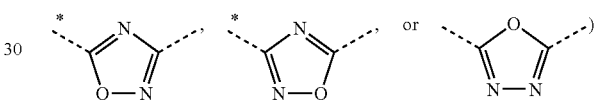

wherein the asterisks indicate the bond that is linked to the pyridine group of Formula (I);
$R^1$ represents methyl, ethyl, or chloro (especially methyl, or ethyl);
$R^2$ represents n-propyl, isobutyl, or isopropoxy (especially n-propyl or isobutyl);
$R^3$ represents hydrogen, methyl, or methoxy (especially hydrogen or methoxy);
$R^4$ represents hydrogen, methyl, ethyl or methoxy;
$R^5$ represents hydroxy-$C_{2-5}$-alkoxy, di-(hydroxy-$C_{1-4}$-alkyl)-$C_{1-4}$-alkoxy, 2,3-dihydroxy-propoxy, —$OCH_2$—$CH(OH)$—$CH_2$—$NR^{51}R^{52}$, or —$OCH_2$—$CH(OH)$—$CH_2$—$NHCOR^{54}$ (especially $R^5$ represents 2,3-dihydroxy-propoxy, or —$OCH_2$—$CH(OH)$—$CH_2$—$NHCOR^{54}$);
$R^{54}$ represents hydroxymethyl, methylaminomethyl, or 2-methylamino-ethyl; and
$R^6$ represents hydrogen, methyl, ethyl or chloro;
wherein for the present embodiment the meanings of one or more of the substituents or groups may be replaced by the meaning(s) given for said substituent(s) or group(s) in any one of embodiments v) to vii), x), xi), xv), xvii) to xix), xxii) to xxv), and xxix) to xxxi).

xxxiii) Another embodiment of the invention relates to pyridin-3-yl derivatives according to embodiment i), wherein
A represents

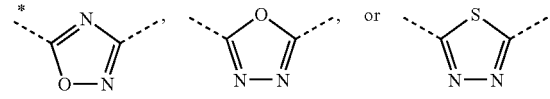

(especially A represents

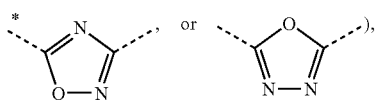

wherein the asterisks indicate the bond that is linked to the pyridine group of Formula (I);
$R^1$ represents hydrogen, $C_{1-4}$-alkyl, or chloro;
$R^2$ represents $C_{1-5}$-alkyl or $C_{1-4}$-alkoxy;
$R^3$ represents hydrogen;
$R^4$ represents $C_{1-4}$-alkyl or $C_{1-4}$-alkoxy;
$R^5$ represents hydroxy, hydroxy-$C_{2-5}$-alkoxy, di-(hydroxy-$C_{1-4}$-alkyl)-$C_{1-4}$-alkoxy, 2,3-dihydroxy-propoxy, —OCH$_2$—CH(OH)—CH$_2$—NR$^{51}$R$^{52}$, or —OCH$_2$—CH(OH)—CH$_2$—NHCOR$^{54}$;
$R^{51}$ represents hydrogen, 2-hydroxyethyl, or 2-hydroxy-1-hydroxymethyl-ethyl (especially hydrogen);
$R^{52}$ represents hydrogen;
$R^{54}$ represents hydroxymethyl; and
$R^6$ represents $C_{1-4}$-alkyl or halogen;
wherein for the present embodiment the meanings of one or more of the substituents or groups may be replaced by the meaning(s) given for said substituent(s) or group(s) in any one of embodiments vi) to xvi), xxi) to xxv), and xxix) to xxxi).

xxxiv) Examples of pyridin-3-yl derivatives according to Formula (I) are selected from:
3-{4-[5-(5-Chloro-6-isopropoxy-pyridin-3-yl)-[1,2,4]oxadiazol-3-yl]-2,6-dimethyl-phenoxy}-propane-1,2-diol;
N-(3-{4-[5-(5-Chloro-6-isopropoxy-pyridin-3-yl)-[1,2,4]oxadiazol-3-yl]-2,6-dimethyl-phenoxy}-2-hydroxy-propyl)-2-hydroxy-acetamide;
3-{4-[5-(6-Isobutyl-5-methyl-pyridin-3-yl)-[1,2,4]oxadiazol-3-yl]-2,6-dimethyl-phenoxy}-propane-1,2-diol;
2-Hydroxy-N-(2-hydroxy-3-{4-[5-(6-isobutyl-5-methyl-pyridin-3-yl)-[1,2,4]oxadiazol-3-yl]-2,6-dimethyl-phenoxy}-propyl)-acetamide;
N-(3-{2-Ethyl-4-[5-(6-isobutyl-5-methyl-pyridin-3-yl)-[1,2,4]oxadiazol-3-yl]-6-methyl-phenoxy}-2-hydroxy-propyl)-2-hydroxy-acetamide;
3-{4-[5-(5,6-Diisobutyl-pyridin-3-yl)-[1,2,4]oxadiazol-3-yl]-2,6-dimethyl-phenoxy}-propane-1,2-diol;
N-(3-{4-[5-(5,6-Diethyl-pyridin-3-yl)-[1,2,4]oxadiazol-3-yl]-2-ethyl-6-methyl-phenoxy}-2-hydroxy-propyl)-2-hydroxy-acetamide;
2-Hydroxy-N-(2-hydroxy-3-{4-[5-(6-isobutyl-5-methyl-pyridin-3-yl)-[1,2,4]oxadiazol-3-yl]-3-methyl-phenoxy}-propyl)-acetamide;
N-(3-{2-Chloro-4-[5-(6-isobutyl-5-methyl-pyridin-3-yl)-[1,2,4]oxadiazol-3-yl]-6-methyl-phenoxy}-2-hydroxy-propyl)-2-hydroxy-acetamide;
N-(3-{2-Chloro-4-[5-(6-isobutyl-5-methyl-pyridin-3-yl)-[1,2,4]oxadiazol-3-yl]-6-methoxy-phenoxy}-2-hydroxy-propyl)-2-hydroxy-acetamide;
N—((R)-3-{2-Ethyl-4-[5-(6-isobutyl-5-methyl-pyridin-3-yl)-[1,2,4]oxadiazol-3-yl]-6-methyl-phenoxy}-2-hydroxy-propyl)-2-hydroxy-acetamide;
N—((S)-3-{2-Ethyl-4-[3-(6-isobutyl-5-methyl-pyridin-3-yl)-[1,2,4]oxadiazol-5-yl]-6-methyl-phenoxy}-2-hydroxy-propyl)-2-hydroxy-acetamide;
N—((S)-3-{2-Ethyl-4-[5-(6-isobutyl-5-methyl-pyridin-3-yl)-[1,2,4]oxadiazol-3-yl]-6-methyl-phenoxy}-2-hydroxy-propyl)-2-hydroxy-acetamide;
(S)-3-{2-Ethyl-4-[5-(5-ethyl-6-isobutyl-pyridin-3-yl)-[1,2,4]oxadiazol-3-yl]-6-methyl-phenoxy}-propane-1,2-diol;
N-(3-{2-Ethyl-4-[5-(5-ethyl-6-isobutyl-pyridin-3-yl)-[1,2,4]oxadiazol-3-yl]-6-methyl-phenoxy}-2-hydroxy-propyl)-2-hydroxy-acetamide;
(R)-3-{2-Ethyl-4-[5-(6-isopropoxy-5-methyl-pyridin-3-yl)-[1,2,4]oxadiazol-3-yl]-6-methyl-phenoxy}-propane-1,2-diol;
(S)-3-{2-Ethyl-4-[5-(6-isopropoxy-5-methyl-pyridin-3-yl)-[1,2,4]oxadiazol-3-yl]-6-methyl-phenoxy}-propane-1,2-diol;
N—((R)-3-{2-Ethyl-4-[5-(6-isopropoxy-5-methyl-pyridin-3-yl)-[1,2,4]oxadiazol-3-yl]-6-methyl-phenoxy}-2-hydroxy-propyl)-2-hydroxy-acetamide;
N—((S)-3-{2-Ethyl-4-[5-(6-isopropoxy-5-methyl-pyridin-3-yl)-[1,2,4]oxadiazol-3-yl]-6-methyl-phenoxy}-2-hydroxy-propyl)-2-hydroxy-acetamide;
3-{2-Ethyl-4-[5-(6-isopropoxy-5-methyl-pyridin-3-yl)-[1,2,4]oxadiazol-3-yl]-6-methyl-phenyl}-N-(2-hydroxy-ethyl)-propionamide;
(R)-3-{2-Ethyl-4-[3-(6-isopropoxy-5-methyl-pyridin-3-yl)-[1,2,4]oxadiazol-5-yl]-6-methyl-phenoxy}-propane-1,2-diol;
(S)-3-{2-Ethyl-4-[3-(6-isopropoxy-5-methyl-pyridin-3-yl)-[1,2,4]oxadiazol-5-yl]-6-methyl-phenoxy}-propane-1,2-diol; and
3-{2-Ethyl-4-[5-(6-isopropoxy-5-methyl-pyridin-3-yl)-[1,2,4]oxadiazol-3-yl]-6-methyl-phenyl}-propionic acid.

xxxv) In another embodiment examples of pyridin-3-yl derivatives according to Formula (I) are selected from:
(R)-3-{4-[5-(5-Chloro-6-isopropoxy-pyridin-3-yl)-[1,2,4]oxadiazol-3-yl]-2,6-dimethyl-phenoxy}-propane-1,2-diol;
(S)-3-{4-[5-(5-Chloro-6-isopropoxy-pyridin-3-yl)-[1,2,4]oxadiazol-3-yl]-2,6-dimethyl-phenoxy}-propane-1,2-diol;
N—((R)-3-{4-[5-(5-Chloro-6-isopropoxy-pyridin-3-yl)-[1,2,4]oxadiazol-3-yl]-2,6-dimethyl-phenoxy}-2-hydroxy-propyl)-2-hydroxy-acetamide;
N—((S)-3-{4-[5-(5-Chloro-6-isopropoxy-pyridin-3-yl)-[1,2,4]oxadiazol-3-yl]-2,6-dimethyl-phenoxy}-2-hydroxy-propyl)-2-hydroxy-acetamide;
(R)-3-{4-[5-(6-Isobutyl-5-methyl-pyridin-3-yl)-[1,2,4]oxadiazol-3-yl]-2,6-dimethyl-phenoxy}-propane-1,2-diol;
(S)-3-{4-[5-(6-Isobutyl-5-methyl-pyridin-3-yl)-[1,2,4]oxadiazol-3-yl]-2,6-dimethyl-phenoxy}-propane-1,2-diol;
2-Hydroxy-N—((R)-2-hydroxy-3-{4-[5-(6-isobutyl-5-methyl-pyridin-3-yl)-[1,2,4]oxadiazol-3-yl]-2,6-dimethyl-phenoxy}-propyl)-acetamide;
2-Hydroxy-N—((S)-2-hydroxy-3-{4-[5-(6-isobutyl-5-methyl-pyridin-3-yl)-[1,2,4]oxadiazol-3-yl]-2,6-dimethyl-phenoxy}-propyl)-acetamide;
N—((R)-3-{2-Ethyl-4-[5-(6-isobutyl-5-methyl-pyridin-3-yl)-[1,2,4]oxadiazol-3-yl]-6-methyl-phenoxy}-2-hydroxy-propyl)-2-hydroxy-acetamide;
N—((S)-3-{2-Ethyl-4-[5-(6-isobutyl-5-methyl-pyridin-3-yl)-[1,2,4]oxadiazol-3-yl]-6-methyl-phenoxy}-2-hydroxy-propyl)-2-hydroxy-acetamide;
(R)-3-{4-[5-(5,6-Diisobutyl-pyridin-3-yl)-[1,2,4]oxadiazol-3-yl]-2,6-dimethyl-phenoxy}-propane-1,2-diol;
(S)-3-{4-[5-(5,6-Diisobutyl-pyridin-3-yl)-[1,2,4]oxadiazol-3-yl]-2,6-dimethyl-phenoxy}-propane-1,2-diol;
N—((R)-3-{4-[5-(5,6-Diethyl-pyridin-3-yl)-[1,2,4]oxadiazol-3-yl]-2-ethyl-6-methyl-phenoxy}-2-hydroxy-propyl)-2-hydroxy-acetamide;

N—((S)-3-{4-[5-(5,6-Diethyl-pyridin-3-yl)-[1,2,4]oxadiazol-3-yl]-2-ethyl-6-methyl-phenoxy}-2-hydroxy-propyl)-2-hydroxy-acetamide;

2-Hydroxy-N—((R)-2-hydroxy-3-{4-[5-(6-isobutyl-5-methyl-pyridin-3-yl)-[1,2,4]oxadiazol-3-yl]-3-methyl-phenoxy}-propyl)-acetamide;

2-Hydroxy-N—((S)-2-hydroxy-3-{4-[5-(6-isobutyl-5-methyl-pyridin-3-yl)-[1,2,4]oxadiazol-3-yl]-3-methyl-phenoxy}-propyl)-acetamide;

N—((R)-3-{2-Chloro-4-[5-(6-isobutyl-5-methyl-pyridin-3-yl)-[1,2,4]oxadiazol-3-yl]-6-methyl-phenoxy}-2-hydroxy-propyl)-2-hydroxy-acetamide;

N—((S)-3-{2-Chloro-4-[5-(6-isobutyl-5-methyl-pyridin-3-yl)-[1,2,4]oxadiazol-3-yl]-6-methyl-phenoxy}-2-hydroxy-propyl)-2-hydroxy-acetamide;

N—((R)-3-{2-Chloro-4-[5-(6-isobutyl-5-methyl-pyridin-3-yl)-[1,2,4]oxadiazol-3-yl]-6-methoxy-phenoxy}-2-hydroxy-propyl)-2-hydroxy-acetamide;

N—((S)-3-{2-Chloro-4-[5-(6-isobutyl-5-methyl-pyridin-3-yl)-[1,2,4]oxadiazol-3-yl]-6-methoxy-phenoxy}-2-hydroxy-propyl)-2-hydroxy-acetamide;

N—((R)-3-{2-Ethyl-4-[5-(6-isobutyl-5-methyl-pyridin-3-yl)-[1,2,4]oxadiazol-3-yl]-6-methyl-phenoxy}-2-hydroxy-propyl)-2-hydroxy-acetamide;

N—((S)-3-{2-Ethyl-4-[3-(6-isobutyl-5-methyl-pyridin-3-yl)-[1,2,4]oxadiazol-5-yl]-6-methyl-phenoxy}-2-hydroxy-propyl)-2-hydroxy-acetamide;

N—((S)-3-{2-Ethyl-4-[5-(6-isobutyl-pyridin-3-yl)-[1,2,4]oxadiazol-3-yl]-6-methyl-phenoxy}-2-hydroxy-propyl)-2-hydroxy-acetamide;

(S)-3-{2-Ethyl-4-[5-(5-ethyl-6-isobutyl-pyridin-3-yl)-[1,2,4]oxadiazol-3-yl]-6-methyl-phenoxy}-propane-1,2-diol;

N—((R)-3-{2-Ethyl-4-[5-(5-ethyl-6-isobutyl-pyridin-3-yl)-[1,2,4]oxadiazol-3-yl]-6-methyl-phenoxy}-2-hydroxy-propyl)-2-hydroxy-acetamide;

N—((S)-3-{2-Ethyl-4-[5-(5-ethyl-6-isobutyl-pyridin-3-yl)-[1,2,4]oxadiazol-3-yl]-6-methyl-phenoxy}-2-hydroxy-propyl)-2-hydroxy-acetamide;

(R)-3-{2-Ethyl-4-[5-(6-isopropoxy-5-methyl-pyridin-3-yl)-[1,2,4]oxadiazol-3-yl]-6-methyl-phenoxy}-propane-1,2-diol;

(S)-3-{2-Ethyl-4-[5-(6-isopropoxy-5-methyl-pyridin-3-yl)-[1,2,4]oxadiazol-3-yl]-6-methyl-phenoxy}-propane-1,2-diol;

N—((R)-3-{2-Ethyl-4-[5-(6-isopropoxy-5-methyl-pyridin-3-yl)-[1,2,4]oxadiazol-3-yl]-6-methyl-phenoxy}-2-hydroxy-propyl)-2-hydroxy-acetamide;

N—((S)-3-{2-Ethyl-4-[5-(6-isopropoxy-5-methyl-pyridin-3-yl)-[1,2,4]oxadiazol-3-yl]-6-methyl-phenoxy}-2-hydroxy-propyl)-2-hydroxy-acetamide;

3-{2-Ethyl-4-[5-(6-isopropoxy-5-methyl-pyridin-3-yl)-[1,2,4]oxadiazol-3-yl]-6-methyl-phenyl}-N-(2-hydroxyethyl)-propionamide;

(R)-3-{2-Ethyl-4-[3-(6-isopropoxy-5-methyl-pyridin-3-yl)-[1,2,4]oxadiazol-5-yl]-6-methyl-phenoxy}-propane-1,2-diol;

(S)-3-{2-Ethyl-4-[3-(6-isopropoxy-5-methyl-pyridin-3-yl)-[1,2,4]oxadiazol-5-yl]-6-methyl-phenoxy}-propane-1,2-diol; and 3-{2-Ethyl-4-[5-(6-isopropoxy-5-methyl-pyridin-3-yl)-[1,2,4]oxadiazol-3-yl]-6-methyl-phenyl}-propionic acid.

xxxvi) A further aspect of the invention relates to novel pyridin-3-yl derivatives of Formula (II)

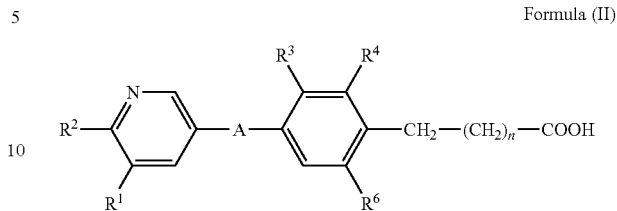

Formula (II)

wherein A, $R^1$, $R^2$, and n are as defined in claim 1; $R^3$ represents hydrogen; $R^4$ represents $C_{1-4}$-alkyl, or $C_{1-4}$-alkoxy; and $R^6$ represents $C_{1-4}$-alkyl, or halogen.

The compounds of Formula (I) and their pharmaceutically acceptable salts can be used as medicaments, e.g. in the form of pharmaceutical compositions for enteral or parental administration.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, *The Science and Practice of Pharmacy*, 20th Edition, Philadelphia College of Pharmacy and Science) by bringing the described compounds of Formula (I) or their pharmaceutically acceptable salts, optionally in combination with other therapeutically valuable substances, into a galenical administration form together with suitable, non-toxic, inert, pharmaceutically acceptable solid or liquid carrier materials and, if desired, usual pharmaceutical adjuvants.

The pharmaceutical compositions comprising a compound of Formula (I) are useful for the prevention and/or treatment of diseases or disorders associated with an activated immune system.

Such diseases or disorders are selected from the group consisting of rejection of transplanted organs, tissue or cells; graft-versus-host diseases brought about by transplantation; autoimmune syndromes including rheumatoid arthritis; systemic lupus erythematosus; antiphospholipid syndrome; Hashimoto's thyroiditis; lymphocytic thyroiditis; multiple sclerosis; myasthenia gravis; type I diabetes; uveitis; episcleritis; scleritis; Kawasaki's disease, uveo-retinitis; posterior uveitis; uveitis associated with Behcet's disease; uveo-meningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; psoriatic arthritis; atopic dermatitis; myopathy; myositis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; scleroderma; alopecia greata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' opthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchiolitis; bronchitis; endometriosis; orchitis; gastric ulcers; ischemic bowel diseases; inflammatory bowel diseases; necrotizing enterocolitis; intestinal lesions associated with thermal burns; coeliac disease; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; tubulointerstitial nephritis; interstitial cystitis; multiple myositis; Guillain-Barré syndrome; Meniere's disease; polyneuritis; multiple neuritis; myelitis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; autoimmune thrombocytopenia; agranulocytosis; pernicious anemia; megaloblastic anemia; anerythroplasia; osteoporosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; myocarditis; scleroderma; Wegener's granuloma; Sjogren's syndrome; adiposis; eosinophilic fascitis; lesions of gingiva, periodontium, alveolar bone, substantia ossea dentis; male pattern alopecia or alopecia senilis; muscular dystrophy; pyoderma; Sezary's syndrome; hypophysitis; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic leukemias; lymphoma; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; peripheral artery disease; carcinogenesis; solid cancer tumors; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; and "acute-on-chronic" liver failure.

Preferred diseases or disorders to be treated and/or prevented with the compounds of Formula (I) are selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, uveoretinitis; atopic diseases such as rhinitis, conjunctivitis, dermatitis; asthma; type I diabetes; post-infectious autoimmune diseases including rheumatic fever and post-infectious glomerulonephritis; solid cancers and tumor metastasis.

Particularly preferred diseases or disorders to be treated and/or prevented with the compounds of Formula (I) are selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis.

The present invention also relates to a method for the prevention or treatment of a disease or disorder mentioned herein comprising administering to a subject a pharmaceutically active amount of a compound of Formula (I).

Furthermore, compounds of the Formula (I) are also useful, in combination with one or several immunomodulating agents, for the prevention and/or treatment of the diseases and disorders mentioned herein. According to a preferred embodiment of the invention, said agents are selected from the group consisting of immunosuppressants, corticosteroids, NSAID's, cytotoxic drugs, adhesion molecule inhibitors, cytokines, cytokine inhibitors, cytokine receptor antagonists and recombinant cytokine receptors.

The present invention also relates to the use of a compound of Formula (I) for the preparation of a pharmaceutical composition, optionally for use in combination with one or several immunomodulating agents, for the prevention or treatment of the diseases and disorders mentioned herein.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

Compounds of the Formula (I) of the present invention can be prepared according to the general sequence of reactions outlined below. Only a few of the synthetic possibilities leading to compounds of Formula (I) are described.

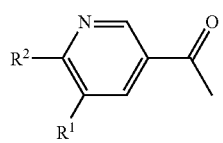

Structure 1

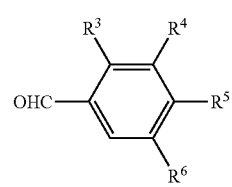

Structure 2

In case A represents —CO—CH=CH—, the compounds of Formula (I) may be prepared by reacting a compound of Structure 1 with a compound of Structure 2 in the presence of a base or an acid. The functional groups present in the residues $R^3$ to $R^6$ may require temporary protection or may even be introduced in additional steps that follow the condensation reaction. Compounds of Formula (I) wherein A represents —CO—CH$_2$—CH$_2$— may be prepared by reacting a compound of Formula (I) wherein A represents —CO—CH=CH— with hydrogen in the presence of a catalyst such as Pd/C, Pt/C, PtO$_2$, etc. in a solvent such as EtOH, MeOH, THF, etc. or mixtures thereof.

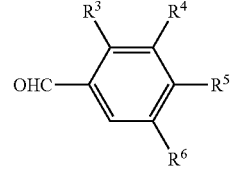

Structure 3

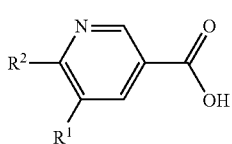

Structure 4

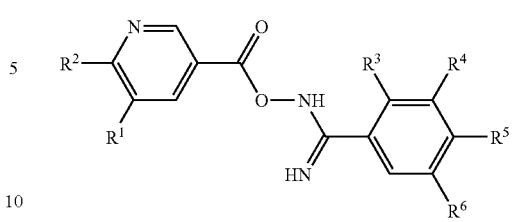

Structure 6

Compounds of Structure 1 may be prepared by reacting a compound of Structure 3 with a methyl Grignard reagent or by treating a compound of Structure 4 with 2 eq. of methyllithium in a solvent such as ether, THF, etc. at temperatures between −20 and 50° C. The Weinreb amide compound of Structure 3 is prepared by treating a compound of Structure 4 with N,O-dimethylhydroxylamine hydrochloride in the presence of coupling reagent such as EDC, DCC, etc. (M. Mentzel, H. M. R. Hoffmann, N-Methoxy N-methyl amides (Weinreb amides) in modern organic synthesis, *Journal fuer Praktische Chemie/Chemiker-Zeitung* 339 (1997), 517-524; J. Singh, N. Satyamurthi, I. S. Aidhen, The growing synthetic utility of Weinreb's amide, *Journal fuer Praktische Chemie* (Weinheim, Germany) 342 (2000) 340-347; V. K. Khlestkin, D. G. Mazhukin, Recent advances in the application of N,O-dialkylhydroxylamines in organic chemistry, *Current Organic Chemistry* 7 (2003), 967-993).

Compounds of Structure 6 may be prepared by reacting a compound of Structure 4 with a compound of Structure 7 in a solvent such as DMF, THF, DCM, etc. in the presence or absence of one or more coupling agents such as TBTU, DCC, EDC, HBTU, HOBt, CDI, etc. and in the presence or absence of a base such as NEt₃, DIPEA, NaH, K₂CO₃, etc. (Lit: e.g. A. Hamze, J.-F. Hernandez, P. Fulcrand, J. Martinez, *J. Org. Chem.* 68 (2003) 7316-7321; and the literature cited above).

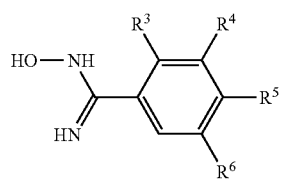

Structure 7

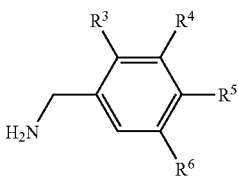

Structure 5

Compounds of Formula (I) which represent a 3-pyridin-3-yl-[1,2,4]oxadiazole derivative are prepared in an analogous fashion (Lit. e.g. C. T. Brain, J. M. Paul, Y. Loong, P. J. Oakley, *Tetrahedron Lett.* 40 (1999) 3275-3278) by reacting a compound of Structure 8 with a compound of Structure 9 and subsequent cyclisation of the corresponding hydroxyamidine ester intermediate.

Compounds of Formula (I) wherein A represents —CO—NH—CH₂— may be prepared by coupling a compound of Structure 5 with a compound with Structure 4 by using a coupling reagent such as EDC, DCC, TBTU, PyBOP, etc. or by coupling a compound of Structure 5 with the corresponding acid chloride or bromide of a compound of Structure 4. Compounds of Formula (I) which represent a 5-pyridin-3-yl-[1,2,4]oxadiazole derivative, are prepared by reacting a compound of Structure 6 in a solvent such as dioxane, THF, DME, xylene, toluene, benzene, pyridine, DMF, DCM, acetic acid, TFA, etc. at rt or elevated temperatures in the presence or absence of auxiliaries such as acids (e.g. TFA, acetic acid, HCl, etc.), bases (e.g. NaH, NaOAc, Na₂CO₃, K₂CO₃, NEt₃, etc.), tetraalkylammonium salts, or water removing agents (e.g. oxalyl chloride, a carboxylic acid anhydride, POCl₃, PCl₅, P₄O₁₀, molecular sieves, Burgess reagent, etc.) (Lit: e.g. A. R. Gangloff, J. Litvak, E. J. Shelton, D. Sperandio, V. R. Wang, K. D. Rice, *Tetrahedron Lett.* 42 (2001), 1441-1443; T. Suzuki, K. Iwaoka, N. Imanishi, Y. Nagakura, K. Miyta, H. Nakahara, M. Ohta, T. Mase, *Chem. Pharm. Bull.* 47 (1999), 120-122; R. F. Poulain, A. L. Tartar, B. P. Déprez, *Tetrahedron Lett.* 42 (2001), 1495-1498; R. M. Srivastava, F. J. S. Oliveira, D. S. Machado, R. M. Souto-Maior, *Synthetic Commun.* 29 (1999), 1437-1450; E. O. John, J. M. Shreeve, *Inorganic Chemistry* 27 (1988), 3100-3104; B. Kaboudin, K. Navaee, *Heterocycles* 60 (2003), 2287-2292).

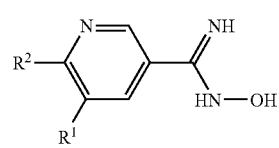

Structure 8

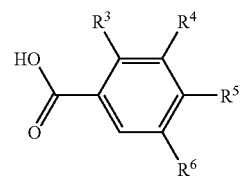

Structure 9

Compounds of Structure 7 and 8 may be prepared by reacting a compound of Structure 10 and 11, respectively, with hydroxylamine or one of its salts in a solvent such as MeOH, EtOH, pyridine, etc. in the presence or absence of a base such as Na₂CO₃, K₂CO₃, NEt₃, KOtBu, etc. (Lit: e.g. T. Suzuki, K. Iwaoka, N. Imanishi, Y. Nagakura, K. Miyta, H. Nakahara, M. Ohta, T. Mase, *Chem. Pharm. Bull.* 47 (1999), 120-122; J. Cui, D. Crich, D. Wink, M. Lam, A. L. Rheingold, D. A. Case, W. T. Fu, Y. Zhou, M. Rao, A. J. Olson, M. E. Johnson, *Bioorg. Med. Chem.* 11 (2003), 3379-3392; R. Miller, F. Lang, Z. J. Song, D. Zewge, WO 2004/035538 (Merck & Co., Inc., USA); B. Kaboudin, K. Navaee, *Heterocycles* 60 (2003), 2287-2292).

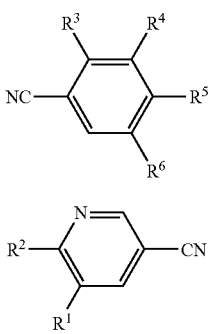

Structure 10

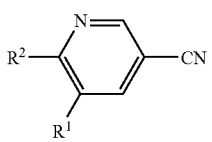

Structure 11

Depending on the nature of the functionalities present in the residues R³ to R⁶ in Structures 2, 5, 6, 7, 9, and 10, these functionalities may require temporary protection. Appropriate protecting groups are known to a person skilled in the art and include e.g. a benzyl or a trialkylsilyl group to protect an alcohol, a ketal to protect a diol, etc. These protecting groups may be employed according to standard methodology (e.g. T. W. Greene, P. G. M. Wuts, Protective Groups in Organic Synthesis, 3$^{rd}$ Edition, Wiley New York, 1991; P. J. Kocienski, Protecting Groups, Thieme Stuttgart, 1994). Alternatively, the desired residues R³ to R⁶, in particular R⁵, may also be introduced in later steps that follow the coupling of the pyridine compounds of Structure 1, 4, 8 or 11 with the phenyl derivatives of Structure 2, 5, 7, 9 or 10 by using a suitable precursor of a compound of Structure 2, 5, 7, 9 and 10. The phenyl compounds of Structure 2, 5, 7, 9 and 10 or their precursors are either commercially available or are prepared according to procedures known to a person skilled in the art.

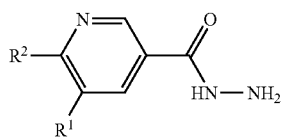

Structure 12

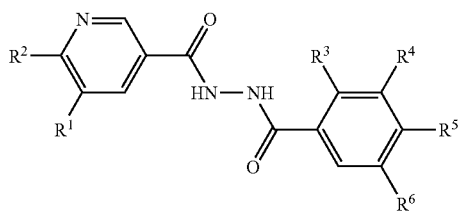

Structure 13

Compounds of Formula (I) which represent a 2-pyridin-3-yl-[1,3,4]oxadiazole or a 2-pyridin-3-yl-[1,3,4]thiadiazole derivative are prepared similarly by reacting a compound of Structure 4 with hydrazine (by using a coupling reagent such as TBTU, DCC, EDC, HBTU, PyPOB, HOBt, CDI, etc.) to form a compound of Structure 12 which is then coupled with a compound of Structure 9 to give a compound of Structure 13. A compound of Structure 13 can also be prepared by following the reverse reaction order i.e. by first coupling a compound of Structure 9 with hydrazine followed by reacting the corresponding hydrazide intermediate with a compound of Structure 4. Dehydration of a compound of Structure 13 to form the desired 2-pyridin-3-yl-[1,3,4]oxadiazole derivative is affected by treating a compound of Structure 13 with a reagent such as POCl₃, CCl₄ or CBr₄ in combination with PPh₃, P₂O₅, Burgess reagent, etc. in a solvent such as toluene, MeCN, dioxane, THF, CHCl₃, etc. at temperatures between 20 and 120° C. in the presence or absence of microwave irradiation. (Lit. e.g. M. A. Garcia, S. Martin-Santamaria, M. Cacho, F. Moreno de la Llave, M. Julian, A. Martinez, B. De Pascual-Teresa, A. Ramos, *J. Med. Chem.* 48 (2005) 4068-4075, C. T. Brain, J. M. Paul, Y. Loong, P. J. Oakley, *Tetrahedron Lett.* 40 (1999) 3275-3278). Likewise, 2-pyridin-3-yl-[1,3,4]thiadiazole derivatives are obtained by cyclising a compound of Sturcture 13 with Lawesson's reagent optionally in combination with P₂S₅ in the presence or absence of a solvent such as pyridine, toluene, THF, MeCN, etc. at elevated temperatures with or without microwave irradiation (Lit. e.g. A. A. Kiryanov, P. Sampson, A. J. Seed, *J. Org. Chem.* 66 (2001) 7925-7929).

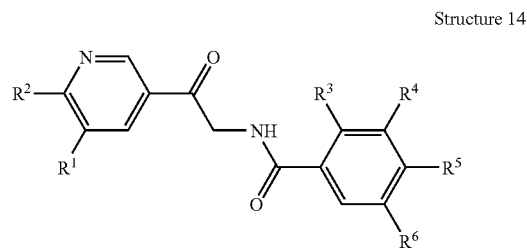

Structure 14

Compounds of Formula (I) which represent a 5-pyridin-3-yl-oxazole or a 5-pyridin-3-yl-thiazole derivative are prepared by treating a compound of Structure 14 either with POCl₃, PCl₅, I₂ in combination with PPh₃ and NEt₃, trifluoroacetic anhydride, Burgess reagent, etc. in a solvent such as toluene, benzene, dioxane, THF, etc. at temperatures between 20 and 120° C. or with Lawesson's reagent optionally in combination with P₂S₅ in the presence or absence of a solvent such as pyridine, toluene, THF, MeCN, etc. at elevated temperatures with or without microwave irradiation as mentioned above (Lit. e.g. N. Sato, T. Shibata, M. Jitsuoka, T. Ohno, T. Takahashi, T. Hirohashi, T. Kanno, H. Iwaasa, A. Kanatani, T. Fukami, Takehiro *Bioorg. & Med. Chem. Lett.* 14 (2004) 1761-1764). The compounds of Structure 14 are prepared by reacting a compound of Structure 15 with a compound of Structure 9. The aminoketon of Structure 15 can be prepared from a compound of Structure 1 by procedures given in the literature (e.g. J. L. LaMattina, *J. Heterocyclic Chem.* 20 (1983) 533-538; M. Pesson, M. Antoine, P. Girard, J. L. Benichon, S. Chabassier, P. De Lajudie, S. Patte, F. Roquet, G. Montay, *Eur. J. Med. Chem.* 15 (1980) 263-268). Compounds of Formula (I) which represent a 2-pyridin-3-yl-oxazole or a 2-pyridin-3-yl-thiazole derivative are prepared in an analogues fashion from a compound of Structure 16 and a compound of Structure 4.

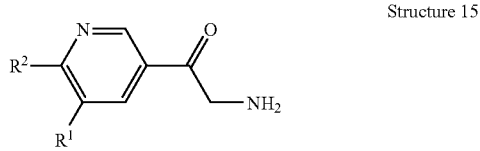

Structure 15

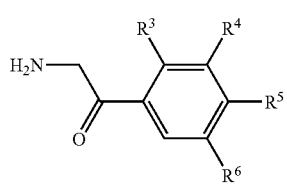

Structure 16

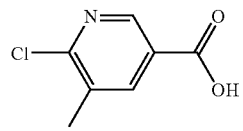

Structure 17

Alternatively, the bonds between the pyridine or the phenylring and the central 5-membered heteroaromatic ring can also be formed by applying palladium catalysed cross coupling reactions.

Methods that effect the transformation of a compound of Structure 4 into a compound of Structure 11, or the opposite, are known to a person skilled in the art.

Compounds of the Structure 4 may be prepared by reacting a 5,6-dichloronicotinic acid ester with an alkyl Grignard reagent in the presence of Fe(acac)$_3$ in a solvent such as THF, dioxane, DMF, NMP, etc., or combinations thereof, at temperatures ranging from −78 to 25° C. (Fürstner conditions, Lit. e.g. A. Fürstner, A. Leitner, M. Mendez, H. Krause *J. Am. Chem. Soc.* 124 (2002) 13856-13863; A. Fürstner, A. Leitner *Angew. Chem.* 114 (2002) 632-635). The reaction conditions can be chosen such that either the 5-chloro-6-alkyl-nicotinic acid ester or the 5,6-dialkyl-nicotinic acid ester is obtained as the main product. The two chlorine atoms in a 5,6-dichloronicotinic acid ester may also be substituted either sequentially or in one step by two alk-1-enyl groups, which may be the same or different, by treating 5,6-dichloronicotinic acid ester with the appropriate alkenyl boron derivative under Suzuki coupling conditions known to a person skilled in the art. The obtained 5,6-di-alkenyl-nicotinic acid ester is hydrogenated to the corresponding 5,6-dialkyl-nicotinic acid ester. In addition, a procedure in which the Fürstner and the Suzuki conditions are employed sequentially can be envisaged. The 5,6-dichloronicotinic acid ester may also be treated with an alcohol or an alcoholate at elevated temperatures to furnish the corresponding 5-chloro-6-alkoxy-nicotinic acid esters. Finally, cleavage of the ester functionality delivers the compounds of Structure 4.

Alternatively, compounds of Structure 4, wherein R$^1$ represents a methyl group, can be prepared from a compound of Structure 17 via formation of the corresponding 6-chloro-5-methyl-nicotinic acid esters using methods well known in the art, followed by derivatisation using Fürstner or Suzuki conditions as described above and subsequent cleavage of the ester function. The compound of Structure 17 can be prepared from known 6-chloro-3-formyl-5-methyl-pyridine (Lit. e.g. EP-0702003) by oxidation of the formyl group to the carboxylic acid using oxidation reagents well known in the art such as aq. H$_2$O$_2$ in formic acid, KMnO$_4$, etc. in the presence or absence of a solvent such as toluene, THF, MeCN, acetone, etc. at temperatures between 0 and 120° C. Compounds of Structure 11, wherein R$^1$ represents a methyl group, can alternatively be prepared as described above from compounds of Structure 4, wherein R$^1$ represents a methyl group; or according to literature methods (Lit.: e.g. J. B. Paine III, *J. Heterocyclic Chem.* 1987, 351-355).

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1 (R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as NEt$_3$, diethylamine) and eluent B (hexane), at a flow rate of 0.8 to 150 mL/min.

Experimental Part

I) Chemistry

The following examples illustrate the invention but do not at all limit the scope thereof.

All temperatures are stated in ° C. Compounds are characterized by $^1$H-NMR (300 MHz) or $^{13}$C-NMR (75 MHz) (Varian Oxford; chemical shifts are given in ppm relative to the solvent used; multiplicities: s=singlet, d=doublet, t=triplet; p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 μm, 120 Å, gradient: 5-95% MeCN in water, 1 min, with 0.04% TFA, flow: 4.5 mL/min), $t_R$ is given in min, (retention times marked with * or as LC-MS* refer to LC run under basic conditions, i.e. eluting with a gradient of MeCN in water containing 13 mM of ammonium hydroxide, other wise identical conditions); by TLC (TLC-plates from Merck, Silica gel 60 F$_{254}$); or by melting point. Compounds are purified by preparative HPLC (column: X-terra RP18, 50×19 mm, 5 μm, gradient: 10-95% MeCN in water containing 0.5% of formic acid) or by MPLC (Labomatic MD-80-100 pump, Linear UVIS-201 detector, column: 350×18 mm, Labogel-RP-18-5s-100, gradient: 10% MeOH in water to 100% MeOH). Racemates can be separated into their enantiomers by preparative HPLC (column: ChiralPaK AD 20×250 mm, 5 μm, 15% EtOH in hexane).

Abbreviations (as Used Herein):

| | |
|---|---|
| aq. | aqueous |
| atm | atmosphere |
| BSA | bovine serum albumin |
| Burgess reagent | methoxycarbonylsulfamoyl triethylammonium hydroxide |
| CC | column chromatography |
| CDI | carbonyl diimidazole |
| DCC | dicyclohexyl carbodiimide |
| DCM | dichloromethane |
| DEAD | diethyl-diazodicarboxylate |
| DIPEA | Hüning's base, diethylisopropylamine |
| DME | 1,2-dimethoxyethane |
| DMF | dimethylformamide |
| DMSO | dimethylsulfoxide |
| dppf | 1,1'-bis(diphenylphosphino)ferrocene |
| EA | ethyl acetate |
| EDC | N-(3-dimethylaminopropyl)-N'-ethyl-carbodiimide |
| ether | diethyl ether |
| EtOH | ethanol |
| Fe(acac)$_3$ | iron(III) acetylacetone-complex |
| h | hour(s) |

-continued

| | |
|---|---|
| HBTU | O-(benzotriazol-1-yl)-N,N,N',N'-tetramethyluronium hexafluorophosphate |
| HOBt | 1-hydroxy-benzotriazole |
| HPLC | high performance liquid chromatography |
| HV | high vacuum conditions |
| Lawesson's reagent | 2,4-bis(4-methoxyphenyl)-1,3,2,4-dithiadiphosphetane-2,4-disulfide |
| LC-MS | liquid chromatography - mass spectrometry |
| MeCN | acetonitrile |
| MeOH | methanol |
| min | minute(s) |
| MPLC | medium pressure liquid chromatography |
| NaOAc | sodium acetate |
| NEt$_3$ | triethylamine |
| NMO | N-methyl-morpholine-N-oxide |
| NMP | 1-methyl-2-pyrrolidone |
| OAc | acetate |
| org. | organic |
| Ph | phenyl |
| PPh$_3$ | triphenylphosphine |
| PyBOP | benzotriazol-1-yl-oxy-tris-pyrrolidino-phosphonium-hexafluoro-phosphate |
| prep. | preparative |
| rac | racemic |
| rt | room temperature |
| sat. | saturated |
| S1P | sphingosine 1-phosphate |
| TBME | tert.-butyl methyl ether |
| TBTU | 2-(1H-benzotriazole-1-yl)-1,2,3,3-tetramethyluronium tetrafluoroborate |
| tert. | tertiary |
| TFA | trifluoroacetic acid |
| THF | tetrahydrofuran |
| TLC | thin layer chromatography |
| t$_R$ | retention time |

Synthesis of Intermediates
Nicotinic Acid 1

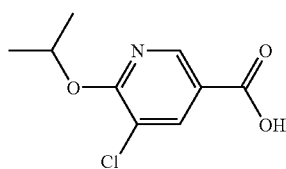

5,6-Dichloronicotinic acid (1.95 g, 10 mmol) is added to a solution of KOtBu (2.28 g, 20 mmol) in isopropanol (20 mL). The mixture is heated at 80° C. for 15 h. The mixture is diluted with water (60 mL) and acidified with 1M aq. HCl. The aq. solution is extracted with ether (5×50 mL) and the combined org. extracts are dried (Na$_2$SO$_4$), filtered and evaporated to provide 5-chloro-6-isopropoxy-nicotinic acid; $^1$H NMR (d$^6$-DMSO) δ 1.38 (d, J=6.2 Hz, 7H), 5.44 (hept, J=6.2 Hz, 1H), 8.18 (d, J=2.1 Hz, 1H), 8.65 (d, J=2.1 Hz, 1H)

Nicotinic Acid 2

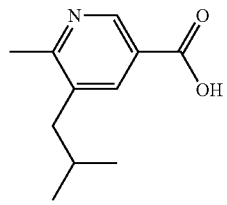

a) A suspension of 5,6-dichloronicotinic acid (5.25 g, 27.3 mmol) in toluene (200 mL) is heated to 80° C. and then slowly treated with N,N-dimethylformamide di-tert. butylacetal (20.0 g, 98.0 mmol). The mixture becomes slightly yellow and clear. Heating and stirring is continued for 3 h before the solution is cooled to rt, diluted with ether and washed with sat. aq. Na$_2$CO$_3$-solution. The org. phase is dried over MgSO$_4$, filtered and the solvent is evaporated. The residue is purified by MPLC (SiO$_2$) to give 5,6-dichloronicotinic acid tert.-butyl ester (5.13 g).

$^1$H NMR (CDCl$_3$): δ 1.62 (s, 9H), 8.30 (d, J=2.0 Hz, 1H), 8.83 (d, J=2.0 Hz, 1H).

b) To a solution of 5,6-dichloronicotinic acid tert.-butyl ester (3.37 g, 13.6 mmol), Fe(acac)$_3$ (719 mg, 2.04 mmol) and NMP (1.95 mL, 20 mmol) in THF (300 mL), a solution of methylmagnesium chloride in THF (3M, 5.4 mL, 16.3 mmol) is slowly added at −78° C. The brown solution turns turbid and black. Stirring is continued for 1 h at −75° C. before it is warmed to 0° C. The reaction is incomplete and the mixture is cooled again at −70° C. A further batch of methylmagnesium bromide in THF (3M, 5.4 mL, 16.3 mmol) is slowly added at −70° C. The dark green mixture is slowly warmed to −20° C. and carefully quenched with 0.7N aq. HCl (150 mL). The mixture is extracted with ether (5×60 mL). The combined org. extracts are dried over Na$_2$SO$_4$, filtered and evaporated to give crude 5-chloro-6-methyl-nicotinic acid tert.-butyl ester as a yellow oil (4.66 g); LC-MS: t$_R$=1.03 min, [M+1]$^+$=228.22.

c) 5-Chloro-6-methyl-nicotinic acid tert.-butyl ester (3.09 g, 13.5 mmol), Fe(acac)$_3$ (719 mg, 2.04 mmol) and NMP (1.95 mL, 20 mmol) are dissolved in THF (3M, 500 mL) and cooled at −78° C. A solution of isobutylmagnesium bromide in THF (2M, 13.6 mmol) is slowly added at −75° C. The brown solution turns turbid and yellow. Stirring is continued for 1 h at −75° C. before it is slowly warmed to rt. The reaction is incomplete, further Fe(acac)$_3$ (719 mg, 2.04 mmol) is added and the mixture is cooled again at −70° C. Further methylmagnesium bromide in THF (2M, 13.6 mmol) is slowly added at −70° C. The dark green mixture is slowly warmed to rt and stirred for 15 h. The mixture is carefully quenched with 0.7N aq. HCl (150 mL). The mixture is extracted with EA (6×60 mL). The combined org. extracts are dried over Na$_2$SO$_4$, filtered and evaporated. The residue is purified by reversed phase MPLC to give 6-methyl-5-isobutyl-nicotinic acid tert.-butyl ester as black oil (0.50 g); LC-MS: t$_R$=0.84 min, [M+1]$^+$=250.14.

d) A solution of 6-methyl-5-isobutyl-nicotinic acid tert.-butyl ester (0.50 g, 2 mmol) is dissolved in dioxane (20 mL) and 4 N HCl in dioxane (30 mL) is added. The mixture is stirred for 3 h. The solvent is evaporated to give 6-methyl-5-isobutyl-nicotinic acid hydrochloride (0.52 g); LC-MS: t$_R$=0.54 min; [M+1]$^+$=194.29; $^1$H NMR (d$^6$-DMSO) δ 0.91 (d, J=6.5 Hz, 6H), 1.91 (hept, J=6.5 Hz), 2.68 (d, J=7.3 Hz, 2H), 2.73 (s, 3H), 8.47 (d, J=1.8 Hz, 1H), 8.90 (d, J=2.0 Hz, 1H).

Nicotinic Acid 3

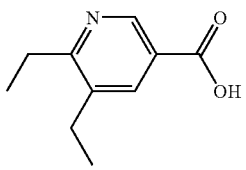

a) To a solution of 5,6-dichloronicotinic acid tert.-butyl ester (5.00 g, 20.0 mmol), and 2,4,6-trivinylcyclotriboroxane pyridine complex (9.700 mg, 40 mmol) in dioxane (30 mL), a solution of 2 M aq. K$_2$CO$_3$ (6 mL) followed by Pd(PPh$_3$)$_4$ (620 mg, 0.38 mmol) and PPh$_3$ (620 mg, 3.8 mmol) is added. The mixture is stirred at 100° C. for 2 h, cooled to rt and diluted with ether (200 mL). The mixture is extracted with 1M aq. NaOH (2×50 mL) and brine (50 mL). The org. phase is dried (Na$_2$SO$_4$), filtered and evaporated. The residue is purified by FC (SiO$_2$, EA-heptane) to give 5-chloro-6-vinyl-nicotinic acid tert.-butyl ester (4.0 g) as a yellow oil; LC-MS: $t_R$=1.05 min, [M+1+CH$_3$CN]$^+$=281.36.

b) A mixture of 5-chloro-6-vinyl-nicotinic acid tert.-butyl ester (2.0 g), Cs$_2$CO$_3$ (3.4 g), tri(tert.-butyl)phosphine (0.04 eq.), tris(dibenzylidenacetone)dipalladium (0.02 eq.), and 2,4,6-trivinylcyclotriboroxane pyridine complex (2.0 g) in dioxane (30 mL) is degassed and heated at 100° C. for 15 h. The mixture is cooled to rt, and diluted with ether (200 mL). The mixture is extracted with 1M aq. NaOH (2×50 mL) and brine (50 mL). The org. phase is dried (Na$_2$SO$_4$), filtered and evaporated. The residue is purified by FC (SiO$_2$, EA-heptane) to give 5,6-divinyl-nicotinic acid tert.-butyl ester (0.89 g) as an oil. LC-MS: $t_R$=1.01 min, [M+1]$^+$=232.04.

c) To a solution of 5,6-divinyl-nicotinic acid tert-butyl ester (890 mg, 3.8 mmol) in THF (20 mL) containing some MeOH, Pd/C (100 mg, 10% Pd) is added and the mixture is stirred under 1 atm of H$_2$ at rt for 3 h. The catalyst is filtered off and the filtrate is evaporated. The remaining residue is purified by FC (SiO$_2$, EA-heptane) to give 5,6-diethyl-nicotinic acid tert-butyl ester (860 mg) as an oil; LC-MS: $t_R$=0.79 min, [M+1]$^+$=236.14.

d) A solution of 5,6-diethyl-nicotinic acid tert-butyl ester (860 mg, 3.65 mmol) in 6 N aq. HCl (15 mL) is stirred at 65° C. for 3 h before the solvent is evaporated. The residue is dried under HV to give 5,6-diethyl-nicotinic acid hydrochloride (923 mg) as an oil; LC-MS: $t_R$=0.50 min, [M+1]$^+$=180.05.

Nicotinic Acid 4

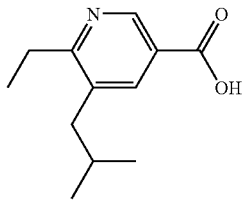

6-Ethyl-5-isobutyl-nicotinic acid is prepared in analogy to Nicotinic acid 3 from 5-chloro-6-vinyl-nicotinic acid tert.-butyl ester and 2,4,6-tri-(2-methyl-propenyl)cycloboroxane pyridine complex, prepared in analogy to a procedure given by F. Kerins, D. F. O'Shea *J. Org. Chem.* 67 (2002) 4968-4971); LC-MS: $t_R$=0.64 min, [M+1]$^+$=207.98.

Nicotinic Acid 5

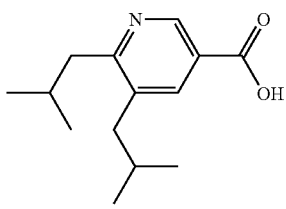

a) A solution of 5,6-dichloronicotinic acid (5.0 g, 26 mmol) in dry EtOH (300 mL) and chlorotrimethylsilane (33 mL, 10 eq.) is stirred at rt for 16 h. The solvent is evaporated, the residue dissolved in ether (200 mL) and washed with a solution of sat. aq. Na$_2$CO$_3$ (75 mL) and brine (50 mL). The org. phase is dried over Na$_2$SO$_4$, filtered and evaporated to give 5,6-dichloronicotinic acid ethyl ester (5.8 g) as a solid; LC-MS: $t_R$=0.96 min, [M+1]$^+$=219.93.

b) To a solution of 5,6-dichloronicotinic acid ethyl ester (0.8 g, 3.6 mmol), and 2,4,6-tri-(2-methyl-propenyl)-cycloboroxane pyridine complex (1.78 g, 5.49 mmol) in DME (20 mL), a solution of 2 M aq. K$_2$CO$_3$ (5 mL) followed by Pd(PPh$_3$)$_4$ (50 mg, 0.068 mmol) and PPh$_3$ (110 mg, 0.68 mmol) is added. The mixture is stirred at 100° C. for 2 days before it is cooled to rt and diluted with ether (100 mL). The phases are separated and the aq. phase re-extracted with ether (50 mL). The combined org. extracts are washed with 1M aq. NaOH (2×40 mL) and brine (40 mL), dried (Na$_2$SO$_4$), filtered and evaporated. The crude product is purified by FC (SiO$_2$, EA-heptane) to give 5,6-di(2-methyl-propenyl)-nicotinic acid ethyl ester (52 mg) as a colourless oil; LC-MS: $t_R$=1.11 min, [M+1]$^+$=260.24.

c) 5,6-di(2-methyl-propenyl)-nicotinic acid ethyl ester (52 mg, 0.3 mmol) is dissolved in THF (10 mL), Pd/C (20 mg, 10% Pd) is added and the mixture is stirred under 1 atm H$_2$ at rt for 15 h. The catalyst is filtered off and the filtrate is evaporated to give 5,6-diisobutyl-nicotinic acid ethyl ester (52 mg) as an oil; LC-MS: $t_R$=1.12 min, [M+1]$^+$=264.19.

d) A solution of 5,6-diisobutyl-nicotinic acid ethyl ester (52 mg, 0.2 mmol) in 6 N aq. HCl (2 mL) is stirred at 65° C. for 15 h before it is cooled to rt and extracted with ether (2×10 mL). The aq. phase is evaporated and the residue is dried under HV to give 5,6-diisobutyl-nicotinic acid hydrochloride (0.12 g) as a colourless solid; LC-MS: $t_R$=0.73 min; [M+1]$^+$=236.40.

Nicotinic Acid 6

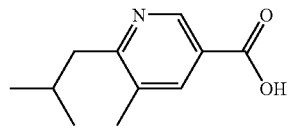

a) Phosphoroxychloride (183 mL, 2 mol) is heated at 90° C. and a mixture of commercially available 2-methyl-2-butennitrile (73 g, 0.9 mol) and DMF (154 mL, 2 mol) is added slowly while keeping the temperature at 100 to 110° C. The mixture is stirred at 110° C. for 15 h, cooled to rt and diluted with DCM (500 mL). The mixture is cooled at 0° C. and carefully quenched with water (500 mL). The phases are separated and the aq. phase extracted with DCM (total of 800 mL). The combined org. extracts are dried (Na$_2$SO$_4$), filtered and evaporated. The residue is crystallised from cyclohexane to provide 6-chloro-3-formyl-5-methyl-pyridine (28.3 g) as slightly yellow crystals; LC-MS: $t_R$=0.76 min, [M+1]$^+$=156.14.

b) A solution of 6-chloro-3-formyl-5-methyl-pyridine (10 g, 64 mmol) in formic acid (200 mL) is cooled at 0° C. and an aq. 50% wt solution of H$_2$O$_2$ in water (9.6 mL, 360 mmol) is added at this temperature. The mixture is stirred at 0° C. for 15 h, carefully diluted with water (200 mL) and extracted with DCM (8×100 mL). The combined org. extracts are washed with 1M aq. HCl (100 mL) (check for remaining peroxide), dried (MgSO$_4$), filtered and evaporated. The residue is dried to give 6-chloro-5-methyl-nicotinic acid (9.56 g); LC-MS: $t_R$=0.72 min, [M+1]$^+$=172.0.

c) A solution of 6-chloro-5-methyl-nicotinic acid (13.85 g, 80.75 mmol) in dry EtOH (200 mL) containing some drops of concentrated H$_2$SO$_4$ is stirred at reflux for 2 days. The solution is cooled to rt, the solvent evaporated, the residue dissolved in EA (200 mL) and washed with a solution of sat. aq. Na₂CO₃ (2×80 mL), 1M aq. KHSO₄ (2×80 mL) and brine (50 mL). The org. phase is dried over MgSO₄, filtered and evaporated to give 6-chloro-5-methyl-nicotinic acid ethyl ester (12.65 g) as a solid; LC-MS: $t_R$=0.92 min; [M+1]⁺=200.10; ¹H NMR (CDCl₃) δ 1.43 (t, J=7.0 Hz, 3H), 2.46 (s, 3H), 4.43 (q, J=7.3 Hz, 2H), 8.16 (m, 1H), 8.84 (d, J=2.0 Hz, 1H).

d) To a solution of 6-chloro-5-methyl-nicotinic acid ethyl ester (4.98 g, 24.9 mmol), 2,4,6-tri-(2-methyl-propenyl)-cycloboroxane pyridine complex (5.74 g, 17.7 mmol, prepared in analogy to a procedure given by F. Kerins, D. F. O'Shea *J. Org. Chem.* 67 (2002) 4968-4971), and PPh₃ (1.15 g, 4.4 mmol) in DME (60 mL), a solution of 2 M aq. K₂CO₃ (20 mL) is added. The mixture is degassed and flushed with N₂ before Pd(PPh₃)₄ (460 mg, 0.4 mmol) is added. The mixture is stirred at 90° C. for 20 h before it is cooled to rt, diluted with EA (150 mL) and washed with sat. aq. NaHCO₃ (2×50 mL). The org. extract is dried over MgSO₄, filtered and evaporated. The crude product is purified by FC (SiO₂, heptane-EA) to give 5-methyl-6-(2-methyl-propenyl)-nicotinic acid ethyl ester (3.98 g) as an orange oil; LC-MS: $t_R$=0.72 min, [M+1]⁺=220.15.

e) 5-Methyl-6-(2-methyl-propenyl)-nicotinic acid ethyl ester (3.98 g, 18.2 mmol) is dissolved in THF (100 mL) and MeOH (100 mL), Pd/C (500 mg, 10% Pd) is added and the mixture is stirred under 1 atm H₂ at rt for 15 h. The catalyst is filtered off and the filtrate is evaporated to give 6-isobutyl-5-methyl-nicotinic acid ethyl ester (3.76 g) as a colourless oil; LC-MS: $t_R$=0.75 min; [M+1]⁺=222.15; ¹H NMR (CDCl₃) δ 0.97 (d, J=6.8 Hz, 6H), 1.42 (t, J=7.3 Hz, 3H), 2.20 (hept, J=6.8 Hz, 1H), 2.38 (s, 3H), 2.75 (d, J=7.0 Hz, 2H), 4.41 (q, J=7.3 Hz, 2H), 8.03 (d, J=1.8 Hz, 1H), 9.00 (d, J=2.0 Hz, 1H).

f) A solution of 6-isobutyl-5-methyl-nicotinic acid ethyl ester (3.75 g, 16.95 mmol) in 12.5% aq. HCl (50 mL) is stirred at 65° C. for 24 h before the solvent is evaporated. The residue is dried under HV to give 6-isobutyl-5-methyl-nicotinic acid hydrochloride (3.55 g) as a white powder; LC-MS: $t_R$=0.57 min, [M+1]⁺=194.25.

Nicotinic Acid 7

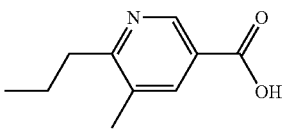

5-Methyl-6-propyl-nicotinic acid (1.85 g as hydrochloride) is prepared in analogy to Nicotinic acid 6 from 6-chloro-5-methyl-nicotinic acid ethyl ester (2.0 g) and commercially available trans-1-propen-1-yl broronic acid (1.3 g); ¹H NMR (d⁶-DMSO) δ 0.96 (t, J=7.3 Hz, 3H), 1.72 (m, 2H), 3.05 (t, J=7.5 Hz, 2H), 8.66 (m, 1H), 8.86 (d, J=1.5 Hz, 1H).

Nicotinic Acid 8

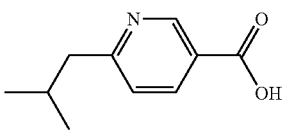

6-Isobutyl-nicotinic acid is prepared in analogy to Nicotinic acid 2 from commercially available 6-chloronicotinic acid ethyl ester and isobutylmagnesium chloride; LC-MS: $t_R$=0.52 min, [M+1]⁺=180.30.

Nicotinic Acid 9

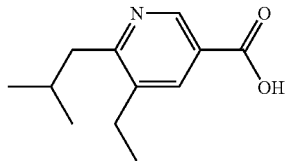

a) To a solution of 5,6-dichloronicotinic acid ethyl ester (2.40 g, 10.9 mmol) and 2,4,6-tris-(2-methyl-propenyl)-cyclotriboroxane pyridine complex (2.02 g, 6.22 mmol, prepared in analogy to a procedure given by F. Kerins, D. F. O'Shea *J. Org. Chem.* 67 (2002) 4968-4971) in dioxane (40 mL) and 2 M aq. K₂CO₃ solution (10 mL), PPh₃ (114 mg, 0.436 mmol) is added. The mixture is degassed and put under N₂ before Pd(PPh₃)₄ (160 mg, 0.218 mmol) is added. The mixture is stirred at 100° C. for 1.5 h before another portion of 2,4,6-tris-(2-methyl-propenyl)-cyclotriboroxane pyridine complex (1.01 g, 3.11 mmol) is added. Stirring is continued at 100° C. for 3 h before the mixture is cooled to rt, diluted with ether, washed with 1N aq. NaOH solution followed by water, dried over MgSO₄, filtered and concentrated. The crude product is purified by CC on silica gel eluting with heptane:EA 9:1 to give 5-chloro-6-(2-methyl-propenyl)-nicotinic acid ethyl ester (2.4 g) as an oil; LC-MS: $t_R$=1.05 min, [M+1]⁺=240.02. To a solution of this material in dioxane (40 mL), 2,4,6-trivinylcyclotriboroxane pyridine complex (1.84 g, 7.63 mmol), Cs₂CO₃ (4.62 g, 14.2 mmol) followed by tri-tert-butylphosphine (88 mg, 0.436 mmol) is added. The mixture is degassed and put under N₂ before Pd₂(dba)₃ (200 mg, 0.218 mmol) is added. The mixture is stirred at 100° C. for 16 h before another portion of 2,4,6-trivinylcyclotriboroxane pyridine complex (1.84 g, 7.63 mmol) and Pd₂(dba)₃ (200 mg, 0.218 mmol) is added. Stirring is continued at 100° C. for 24 h before the mixture is diluted with EA, washed with 1N aq. NaOH solution, dried over MgSO₄, filtered and concentrated. The crude product is purified by CC on silica gel eluting with heptane:EA 10:1 to give a first portion of 6-(2-methyl-propenyl)-5-vinyl-nicotinic acid ethyl ester. In addition, unreacted 5-chloro-6-(2-methyl-propenyl)-nicotinic acid ethyl ester is isolated. This material is again treated with 2,4,6-trivinylcyclotriboroxane pyridine complex as described before. Work-up, purification and combining the two portions give 6-(2-methyl-propenyl)-5-vinyl-nicotinic acid ethyl ester (1.37 g) as an oil; LC-MS: $t_R$=0.87 min, [M+1]⁺=232.13.

b) To solution of 6-(2-methyl-propenyl)-5-vinyl-nicotinic acid ethyl ester (1.37 g, 6.74 mmol) in THF (20 mL), Pd/C (100 mg, 10% Pd) followed by EtOH (20 mL) is added. The mixture is stirred under 1 atm of H₂ at rt for 24 h. The catalyst is removed by filtration and the filtrate is concentrated. The crude product is purified by CC on silica gel eluting with heptane:EA 4:1 to give 5-ethyl-6-isobutyl-nicotinic acid ethyl ester (970 mg) as a colourless oil, LC-MS: $t_R$=0.79 min, [M+1]⁺=236.20; ¹H NMR (CDCl₃): δ0.97 (d, J=6.8 Hz, 6H), 1.27 (t, J=7.5 Hz, 3H), 1.42 (t, J=7.0 Hz, 3H), 2.17-2.28 (m, 1H), 2.69-2.78 (m, 4H), 4.42 (q, J=7.0 Hz, 2H), 8.07 (s, 1H), 9.00 (s, 1H).

c) A solution of 5-ethyl-6-isobutyl-nicotinic acid ethyl ester (970 mg, 4.12 mmol) in 25% aq.

HCl is stirred at 95° C. for 8 h. The solvent is evaporated and the residue is dried under high vacuum to give 5-ethyl-6-isobutyl-nicotinic acid hydrochloride (1.15 g, presumably as hydrate) as a colourless resin, LC-MS: $t_R$=0.62 min, [M+1]⁺=208.35.

Nicotinic Acid 10

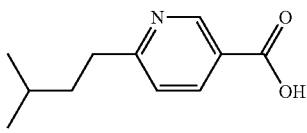

6-(3-Methyl-butyl)-nicotinic acid is prepared by reacting 6-chloro-nicotinic acid tert-butly ester with 3-methyl-butyl-magnesium bromide under Fürstner conditions as described for Nicotinic acid 2; LC-MS: $t_R$=0.58 min, [M+1]$^+$=194.30.

Nicotinic Acid 11

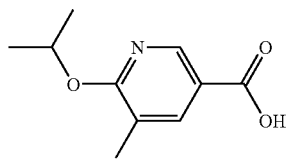

a) To a solution of potassium tert. butylate (1.26 g, 11.3 mmol) in isopropanol (30 mL), 2,5-dibromo-3-picoline (2.89 g, 11.3 mmol) is added. The mixture is stirred at 80° C. for 15 h before another portion of potassium tert.-butylate (2.53 g, 27.5 mmol) is added. Stirring is continued at 80° C. for 24 h before the mixture is diluted with sat. aq. NaHCO$_3$-solution. The mixture is extracted with ether, the org. extract is dried over MgSO$_4$, filtered and concentrated. The crude product is purified by CC on silica gel eluting with heptane:EA 9:1 to give 5-bromo-2-isopropoxy-3-methyl-pyridine (1.24 g) as a colourless oil; LC-MS: $t_R$=1.06 min; [M+1]$^+$=230.00; $^1$H NMR (CDCl$_3$): δ1.35 (d, J=6.3 Hz, 6H), 2.16 (s, 3H), 5.27 (hept, J=6.3 Hz, 1H), 7.48 (d, J=1.5 Hz, 1H), 8.02 (d, J=2.0 Hz, 1H).

b) A solution of 5-bromo-2-isopropoxy-3-methyl-pyridine (1.24 g, 5.39 mmol) and 2,4,6-trivinylcyclotriboroxane pyridine complex (1.27 g, 5.26 mmol) in DME (12 mL) and 2 M aq. K$_2$CO$_3$ (5 mL) is degassed and put under argon before Pd(PPh$_3$)$_4$ (112 mg, 0.097 mmol) is added. The mixture is stirred at 80° C. for 15 h before it is cooled to rt, diluted with ether (50 mL), washed with sat. aq. NaHCO$_3$ solution (2×30 mL), dried over MgSO$_4$, filtered and concentrated. The crude product is purified by CC on silica gel eluting with heptane:EA 9:1 to give 2-isopropoxy-3-methyl-5-vinyl-pyridine (703 mg) as pale yellow oil; LC-MS: $t_R$=1.01 min; [M+1]$^+$=178.11.

c) To a solution of 2-isopropoxy-3-methyl-5-vinyl-pyridine (703 mg, 3.97 mmol) in acetone (80 mL), KMnO$_4$ (1.60 g, 10.1 mmol) is added and the mixture is stirred at rt for 18 h. The dark brown suspension is filtered and the clear, colourless filtrate is evaporated to dryness to give 6-isopropoxy-5-methyl-nicotinic acid (1.06 g, as potassium salt) as an off-white solid; LC-MS: $t_R$=0.86 min; [M+1]$^+$=196.09; $^1$H NMR (D$_2$O): δ1.31 (d, J=6.3 Hz, 6H), 2.14 (s, 3H), 5.15 (hept, J=7.0 Hz, 1H), 7.91 (s, 1H), 8.34 (s, 1H).

N-Hydroxy-6-isobutyl-5-methyl-nicotinamidine

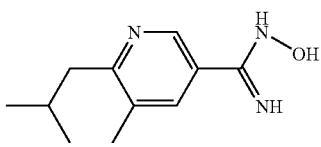

a) A solution of 6-isobutyl-5-methyl-nicotinic acid ethyl ester (2.86 g, 12.9 mmol) in 7 N NH$_3$ in MeOH (80 mL) is stirred at 60° C. for 20 h before the solvent is removed in vacuo. The residue is dried to give 6-isobutyl-5-methyl-nicotinamide (1.89 g) as a yellow oil; LC-MS: $t_R$=0.66 min, [M+1]$^+$=193.29; $^1$H NMR (D$_6$-DMSO): δ 0.91 (d, J=6.5 Hz, 6H), 2.08-2.20 (m, 1H), 2.32 (s, 3H), 2.65 (d, J=7.3 Hz, 2H), 7.43 (s, 1H), 7.95 (s, 1H), 8.01 (m, 1H), 8.78 (s, 1H).

b) To a solution of 6-isobutyl-5-methyl-nicotinamide (1.89 g, 9.85 mmol) in DCM (40 mL) and pyridine (2.83 g, 39.4 mmol), TFA anhydride (5.17 g, 24.6 mmol) is added portionwise at 0° C. The mixture is stirred at rt for 24 h, diluted with DCM and washed with water, 4% aq. citric acid solution followed by sat. aq. NaHCO$_3$ solution. The org. extract is dried over MgSO$_4$, filtered and concentrated. The crude product is purified by CC on silica gel eluting with heptane:EA 9:1 to give 6-isobutyl-5-methyl-nicotinonitrile (1.35 g) as a white solid; LC-MS: $t_R$=0.89 min, [M+1]$^+$=175.11.

c) To a solution of potassium tert-butylate (3.04 g, 27.1 mmol) in MeOH (60 mL), hydroxylamine hydrochloride (1.62 g, 23.2 mmol) is added at 0° C. To this suspension, 6-isobutyl-5-methyl-nicotinonitrile (1.35 g, 7.75 mmol) is added. The mixture is refluxed for 3 h, cooled to rt, filtered and the filtrate is evaporated to dryness. The residue is suspended in a small amount of water and then extracted with EA. The org. extract is concentrated and dried under high vacuum to give N-hydroxy-6-isobutyl-5-methyl-nicotinamidine (1.53 g) as a pale yellow oil; LC-MS: $t_R$=0.68 min, [M+1]$^+$=208.22; $^1$H NMR (D$_6$-DMSO): δ 0.91 (d, J=6.8 Hz, 6H), 2.06-2.17 (m, 1H), 2.29 (s, 3H), 2.61 (d, J=7.0 Hz, 2H), 5.85 (s br, 2H), 7.76 (s, 1H), 8.60 (s, 1H), 9.68 (s, 1H).

N-Hydroxy-6-isopropoxy-5-methyl-nicotinamidine

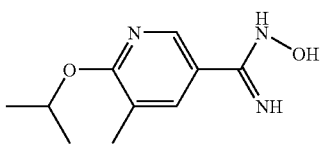

The title compound is prepared in analogy to N-hydroxy-6-isobutyl-5-methyl-nicotinamidine from Nicotinic acid 11; LC-MS: $t_R$=0.64 min, [M+1]$^+$=210.08.

4-Allyloxy-N-hydroxy-benzamidine

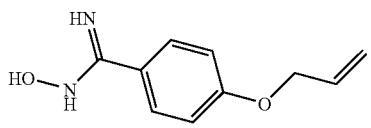

The title compound is prepared in analogy to 4-allyloxy-N-hydroxy-3,5-dimethyl-benzamidine by allylating commercially available 4-hydroxy-benzonitrile followed by transforming the nitrile to the hydroxyamidine; LC-MS: $t_R$=0.59 min, [M+1]$^+$=193.58.

4-Allyloxy-N-hydroxy-2-methyl-benzamidine

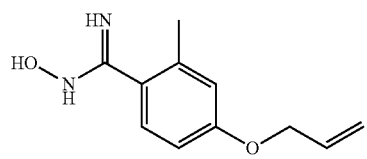

The title compound is prepared in analogy to 4-allyloxy-3-ethyl-N-hydroxy-5-methyl-benzamidine starting from commercially available 4-hydroxy-2-methyl-benzaldehyde; LC-MS: $t_R$=0.62 min, [M+1]$^+$=207.10; $^{13}$C NMR (CDCl$_3$): δ 20.72, 68.91, 104.72, 112.75, 116.45, 118.32, 118.53, 132.25, 134.19, 144.09, 161.71.

4-Allyloxy-N-hydroxy-2-methoxy-benzamidine

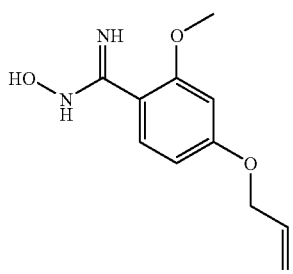

The title compound is prepared from commercially available 4-hydroxy-2-methoxy-benzaldehyde following literature procedures (references cited for 3-ethyl-4,N-dihydroxy-5-methyl-benzamidine); LC-MS: $t_R$=0.64 min; [M+1]$^+$=223.24; $^1$H NMR (D$_6$-DMSO): δ 9.33 (s br, 1H), 7.30 (d, J=8.2 Hz, 1H), 6.60 (d, J=2.3 Hz, 1H), 6.50 (dd, J=2.3, 8.2 Hz, 1H), 6.10-5.94 (m, 1H), 5.50 (s, 2H), 5.40 (d, J=17.0 Hz, 1H), 5.24 (d, J=10.6 Hz, 1H), 4.57 (d, J=4.7 Hz, 2H), 3.76 (s, 3H).

4-Allyloxy-N-hydroxy-3-methoxy-benzamidine

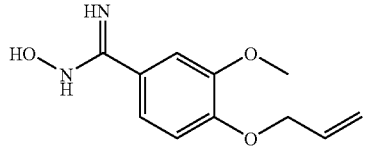

The title compound is prepared in analogy to 4-allyloxy-N-hydroxy-3,5-dimethyl-benzamidine by allylating commercially available 4-hydroxy-3-methoxy-benzonitrile followed by transforming the nitrile to the hydroxyamidine; LC-MS: $t_R$=0.59 min, [M+1]$^+$=223.18.

4-Allyloxy-3-bromo-N-hydroxy-benzamidine

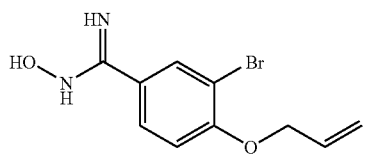

The title compound is prepared in analogy to 4-allyloxy-N-hydroxy-3,5-dimethyl-benzamidine by allylating commercially available 3-brome-4-hydroxy-benzonitrile followed by transforming the nitrile to the hydroxyamidine; LC-MS: $t_R$=0.68 min, [M+1]$^+$=270.96.

4-Allyloxy-3-chloro-N-hydroxy-5-methyl-benzamidine

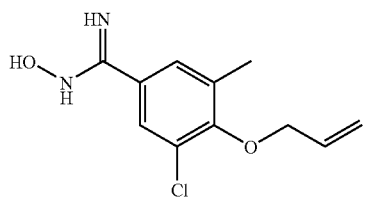

The title compound is prepared in analogy to 4-allyloxy-3-ethyl-N-hydroxy-5-methyl-benzamidine starting from commercially available 3-chloro-4-hydroxy-5-methyl-benzaldehyde; LC-MS: $t_R$=0.69 min, [M+1]$^+$=241.10.

4-Allyloxy-N-hydroxy-3,5-dimethyl-benzamidine

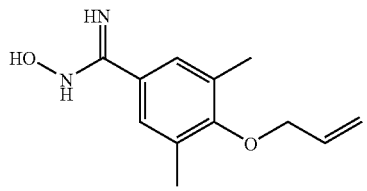

The title compound is prepared by allylating commercially available 4-hydroxy-3,5-dimethyl-benzonitrile with allylbromide in the presence of NaOH in isopropanol at rt. The nitrile is then transformed to the hydroxyamidine according to literature procedures (e.g. E. Meyer, A. C. Joussef, H. Gallardo, Synthesis 2003, 899-905); $^1$H NMR (CD$_3$OD): δ 7.27 (s, 2H), 6.10 (m, 1H), 5.42 (m, 1H), 5.26 (m, 1H), 4.31 (dt, J=5.6, 1.5 Hz, 2H), 2.29 (s, 6H).

4-Allyloxy-3-ethyl-N-hydroxy-5-methyl-benzamidine

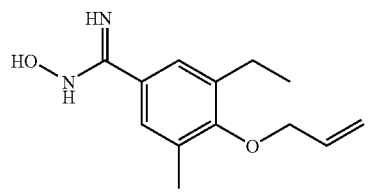

The title compound is prepared by allylating 3-ethyl-4-hydroxy-5-methyl-benzaldehyde which is prepared from 2-ethyl-6-methyl-phenol following literature procedures (see 3-ethyl-4,N-dihydroxy-5-methyl-benzamidine). The aldehyde is then transformed into the corresponding hydroxyamidine according to literature procedures (see 3-ethyl-4,N-dihydroxy-5-methyl-benzamidine); LC-MS: t$_R$=0.72 min; [M+1]$^+$=235.09; $^1$H NMR (CD$_3$OD): δ 7.31 (s, 1H), 7.29 (s, 1H), 6.10 (m, 1H), 5.43 (dd, J=17.0, 1.5 Hz, 1H), 5.27 (dd, J=10.3, 1.2 Hz, 1H), 4.81 (s br, 3H), 4.31 (d, J=5.6 Hz, 2H), 2.67 (q, J=7.6 Hz, 2H), 2.30 (s, 3H), 1.23 (t, J=7.6 Hz, 4H).

4-Allyloxy-3-chloro-N-hydroxy-5-methoxy-benzamidine

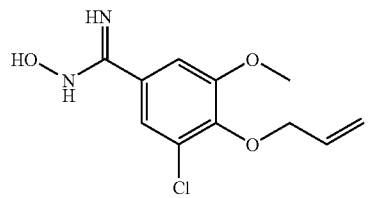

The title compound is prepared by allylating commercially available 3-chloro-4-hydroxy-5-methoxybenzaldehyde (see 4-Allyloxy-3-ethyl-N-hydroxy-5-methyl-benzamidine). The aldehyde is then transformed into the corresponding hydroxyamidine according to literature procedures (see 3-ethyl-4,N-dihydroxy-5-methyl-benzamidine); LC-MS: t$_R$=0.69 min; [M+1]$^+$=257.26.

4,N-Dihydroxy-3,5-dimethyl-benzamidine

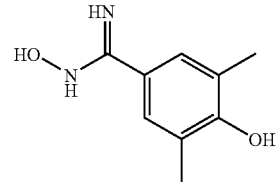

The title compound is prepared from commercially available 4-hydroxy-3,5-dimethyl-benzonitrile according to literature procedures (e.g. E. Meyer, A. C. Joussef, H. Gallardo, Synthesis 2003, 899-905); $^1$H NMR (CD$_3$OD): δ 7.20 (s, 2H), 2.20 (s, 6H).

3-Ethyl-4,N-dihydroxy-5-methyl-benzamidine

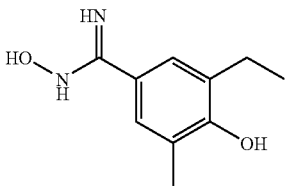

The title compound is prepared from commercially available 2-ethyl-6-methyl-phenol following literature procedures (G. Trapani, A. Latrofa, M. Franco, C. Altomare, E. Sanna, M. Usala, G. Biggio, G. Liso, J. Med. Chem. 41 (1998) 1846-1854; A. K. Chakraborti, G. Kaur, Tetrahedron 55 (1999) 13265-13268; E. Meyer, A. C. Joussef, H. Gallardo, Synthesis 2003, 899-905); LC-MS: t$_R$=0.55 min; $^1$H NMR (d$^6$-DMSO): δ 9.25 (s br, 1H), 7.21 (s, 2H), 5.56 (s, 2H), 2.55 (q, J=7.6 Hz, 2H), 2.15 (s, 3H), 1.10 (t, J=7.6 Hz, 3H).

3,5-Diethyl-4,N-dihydroxy-benzamidine

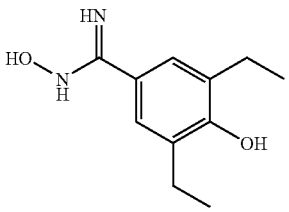

The title compound is prepared from commercially available 2,6-diethylaniline following literature procedures (G. G. Ecke, J. P. Napolitano, A. H. Filbey, A. J. Kolka, J. Org. Chem.

22 (1957) 639-642; and literature cited for 3-ethyl-4,N-dihydroxy-5-methyl-benzamidine); LC-MS: $t_R$=60 min; [M+1]$^+$=209.46.

3-Chloro-4,N-dihydroxy-5-methoxy-benzamidine

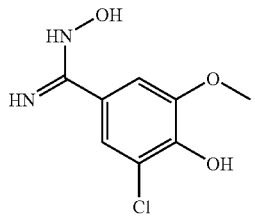

The title compound is prepared from commercially available 3-chloro-4-hydroxy-5-methoxy-benzaldehyde in analogy to the literature cited for 3-ethyl-4,N-dihydroxy-5-methyl-benzamidine; LC-MS: $t_R$=0.49 min; [M+1]$^+$=216.96; $^1$H NMR (D$_6$-DMSO): δ 3.84 (s, 3H), 5.79 (s, 2H), 7.22 (d, J=1.5 Hz, 1H), 7.27 (d, J=1.8 Hz, 1H), 9.52 (s, 1H), 9.58 (s br, 1 H).

[4-(N-Hydroxycarbamimidoyl)-phenyl]-acetic acid

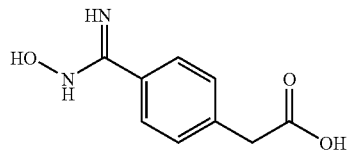

a) To a solution of methyl (4-cyanophenyl)acetate (4.00 g, 27.8 mmol) in MeOH (20 mL), hydroxylamine hydrochloride (3.17 g, 45.7 mmol) and NaHCO$_3$ (3.84 g, 45.7 mmol) is added. The suspension is stirred at 60° C. for 18 h before it is filtered and the filtrate is concentrated. The residue is dissolved in DCM, washed with water followed by brine, dried over MgSO$_4$, filtered, concentrated and dried to give methyl [4-(N-hydroxycarbamimidoyl)-phenyl]-acetate (3.67 g) as a colourless oil; LC-MS: $t_R$=0.50 min, [M+1]$^+$=209.05.

b) A solution of methyl [4-(N-hydroxycarbamimidoyl)-phenyl]-acetate (3.67 g, 17.6 mmol) in 25% aq. HCl (15 mL) is stirred at 65° C. for 4 h. The solvent is removed in vacuo and the residue is dried under high vacuum to give [4-(N-hydroxycarbamimidoyl)-phenyl]-acetic acid (3.80 g, presumably as hydrochloride) as a yellow solid; LC-MS: $t_R$=0.34 min, [M+1]$^+$=195.05.

{4-[5-(6-Isobutyl-5-methyl-pyridin-3-yl)-[1,2,4]oxadiazol-3-yl]-phenyl}-acetic acid

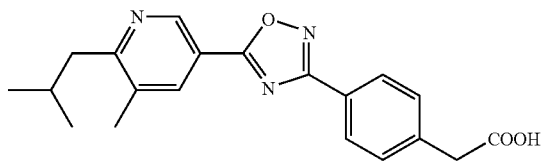

The title compound is prepared starting from Nicotinic acid 6 and [4-(N-hydroxycarbamimidoyl)-phenyl]-acetic acid in analogy to Example 13; LC-MS: $t_R$=0.96 min, [M+1]$^+$=352.39.

3-[2-Ethyl-4-(N-hydroxycarbamimidoyl)-6-methyl-phenyl]-propionic acid tert-butyl ester

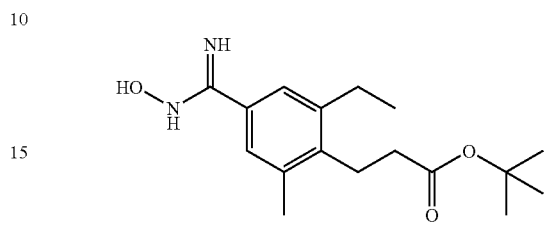

a) To a solution of 3-ethyl-4-hydroxy-5-methyl-benzoic acid (80.3 g, 0.446 mol) is DMF (500 mL), KHCO$_3$ (53.5 g, 0.535 mol) followed by benzylbromide (114.3 g, 0.668 mol) is added. The mixture is stirred at 50° C. for 18 h before it is cooled to rt, diluted with water (250 mL), and extracted with TBME (2×250 mL). The org. extracts are washed with water, and then concentrated. The crude product is purified by CC on silica gel eluting with heptane:EA 19:1 to 9:1 to give 3-ethyl-4-hydroxy-5-methyl-benzoic acid benzyl ester (108.5 g) as a beige solid; $^1$H NMR (CDCl$_3$): δ1.28 (t, J=7.5 Hz, 3H), 2.30 (s, 3H), 2.68 (q, J=7.8 Hz, 2H), 5.24 (s, 1H), 5.37 (s, 2H), 7.33-7.45 (m, 3H), 7.45-7.50 (m, 2H), 7.77 (s, 1H), 7.79 (s, 1H).

b) To a solution of 3-ethyl-4-hydroxy-5-methyl-benzoic acid benzyl ester (97.5 g, 0.361 mol) and pyridine (57.1 g, 0.721 mol) in DCM (1000 mL), a solution of trifluoromethanesulfonic anhydride (122.1 g, 0.433 mol) in DCM (100 mL) is added dropwise at 0° C. After complete addition, the mixture is stirred at rt for 2 h before it is washed with 2 N aq. HCl (500 mL) followed by water (500 mL). The org. extract is concentrated and dried to give 3-ethyl-5-methyl-4-trifluoromethanesulfonyloxy-benzoic acid (140.5 g) as an orange oil; $^1$H NMR δ 1.30 (t, J=7.5 Hz, 3H), 2.46 (s, 3H), 2.83 (q, J=7.5 Hz, 2H), 5.39 (s, 2H), 7.35-7.50 (m, 5H), 7.87 (s, 1H), 7.91 (s, 1H).

c) To a solution of 3-ethyl-5-methyl-4-trifluoromethanesulfonyloxy-benzoic acid (10.0 g, 25 mmol), tert.-butyl acrylate (6.37 g, 50 mmol), NEt$_3$ (5.03 g, 50 mmol), and DPPP (0.82 g, 2 mmol) in DMF (100 mL), Pd(OAc)$_2$ (0.45 g, 2 mmol) is added under a N$_2$-atmosphere. The mixture is stirred at 115° C. for 3 h before is cooled to rt, filtered over a celite pad. The pad is washed with TBME (250 mL) and water (500 mL) is added to the filtrate. The layers are separated and the org. layer is washed twice with water (2×500 mL), dried over MgSO$_4$ and evaporated to dryness. To the crude product is added EtOH (100 mL). A thick suspension forms. The solid material is collected, washed with ice-cold EtOH (10 mL) to give 4-(2-tert-butoxycarbonyl-vinyl)-3-ethyl-5-methyl-benzoic acid benzyl ester (3.8 g) as an off-white solid.

d) To a solution of 4-(2-tert-butoxycarbonyl-vinyl)-3-ethyl-5-methyl-benzoic acid benzyl ester (10.0 g, 26 mmol) in THF 100 mL), Pd/C (0.5 g, 20% Pd) is added under nitrogen. The mixture is stirred at rt for 48 h under 1 bar of H$_2$. The catalyst is filtered off over a celite pad and the filtrate is concentrated to dryness to give 4-(2-tert-butoxycarbonyl-ethyl)-3-ethyl-5-methyl-benzoic acid (7.64 g) as a white solid; ¹H NMR δ 1.29 (t, J=7.5 Hz, 3H), 1.49 (s, 9H), 2.36-2.41 (m, 2H), 2.74 (q, J=7.5 Hz, 2H), 2.99-3.05 (m, 2H), 7.77 (s, 1H), 7.80 (s, 1H).

e) To a solution of 4-(2-tert-butoxycarbonyl-ethyl)-3-ethyl-5-methyl-benzoic acid (36.0 g, 123 mmol) in isopropanol (400 mL), HOBT (18.3 g, 135 mmol) followed by EDC HCl (27.1 g, 142 mmol) is added. The mixture is stirred at rt for 1 h before aq. ammonia (69 mL of 25% solution) is added. Stirring is continued for 1 h before the mixture is diluted with DCM (500 mL) and washed with half sat. aq. NaHCO₃ solution (3×400 mL), followed by water (400 mL). The org. extract is dried over MgSO₄, filtered and concentrated. The crude product is triturated with TBME 8250 mL). The solid material is collected, washed with additional TBME (50 mL) and dried under high vacuum to give 3-(4-carbamoyl-2-ethyl-6-methyl-phenyl)-propionic acid tert-butyl ester (31.91 g) as a white solid.

f) To a solution of 3-(4-carbamoyl-2-ethyl-6-methyl-phenyl)-propionic acid tert-butyl ester (30.0 g, 103 mmol) and NEt₃ (31.3 g, 309 mmol) in DCM (300 mL), trifluoroacetic anhydride (23.8 g, 113 mmol) is added slowly. The exothermic reaction is kept below 5° C. with cooling. After complete addition, the mixture is stirred at rt for 1 h. The mixture is washed twice with water (2×300 mL) and the org. extract is evaporated to dryness to give 3-(4-cyano-2-ethyl-6-methyl-phenyl)-propionic acid tert-butyl ester (28.4 g) as a pale yellow oil; ¹H NMR δ 1.25 (t, J=7.5 Hz, 3H), 1.48 (s, 9H), 2.32-2.37 (m, 2H), 2.38 (s, 3H), 2.70 (q, J=7.5 Hz, 2H), 2.95-3.02 (m, 2H), 7.30 (s, 1H), 7.34 (s, 1H).

g) A solution of 3-(4-cyano-2-ethyl-6-methyl-phenyl)-propionic acid tert-butyl ester (37.0 g, 135 mmol), hydroxylamine hydrochloride (14.1 g, 203 mmol) and NEt₃ (27.4 g, 271 mmol) in MeOH (400 mL) is heated to reflux for 7 h before it is cooled to rt. The solvent is evaporated and the residue is taken up in isopropylacetate (500 mL) and washed twice with water (500 mL). The org. extract is dried over MgSO₄, filtered, evaporated and dried to give 3-[2-ethyl-4-(N-hydroxycarbamimidoyl)-6-methyl-phenyl]-propionic acid tert-butyl ester (40.8 g) as a pale yellow solid; ¹H NMR δ 1.26 (t, J=7.5 Hz, 3H), 1.49 (s, 9H), 2.33-2.41 (m, 5H), 2.66-2.74 (m, 2H), 2.93-3.01 (m, 2H), 4.85 (s, 1H), 7.28 (s, 2H).

3-[2-Ethyl-4-(N-hydroxycarbamimidoyl)-6-methyl-phenyl]-propionic acid

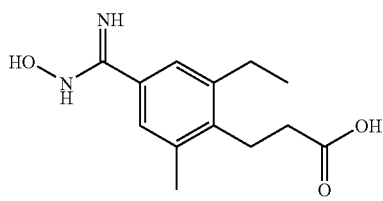

a) 3-(4-Cyano-2-ethyl-6-methyl-phenyl)-propionic acid ethyl ester is prepared in analogy to 3-(4-cyano-2-ethyl-6-methyl-phenyl)-propionic acid tert-butyl ester; ¹H NMR (CDCl₃): δ 1.21-1.31 (m, 6H), 2.37 (s, 3H), 2.41-2.47 (m, 2H), 2.69 (q, J=7.5 Hz, 2H), 2.99-3.05 (m, 2H), 4.18 (q, J=7.0 Hz, 2H), 7.30 (s, 1H), 7.33 (s, 1H).

b) A solution of 3-(4-cyano-2-ethyl-6-methyl-phenyl)-propionic acid ethyl ester (55.0 g, 224 mmol) in THF (220 mL) and 1N aq. NaOH solution (220 mL) is stirred at rt for 2 before it is diluted with water (200 mL) and extracted with DCM (2×200 mL). The aqueous phase is added to 32% aq. HCl solution (50 mL) at 15-30° C. A precipitate forms. The solid material is collected, washed with water and dried under high vacuum to give 3-(4-cyano-2-ethyl-6-methyl-phenyl)-propionic acid (40.87 g) as pale brown crystals; ¹H NMR (D₆-DMSO): δ 1.17 (t, J=7.5 Hz, 3H), 2.30-2.39 (m, 5H), 2.67 (q, J=7.3 Hz, 2H), 2.87-2.94 (m, 2H), 7.47 (s, 2H), 12.30 (s, 1H).

c) To a solution of 3-(4-cyano-2-ethyl-6-methyl-phenyl)-propionic acid (10.0 g, 46.0 mmol) in EtOH (80 mL), NEt₃ (13.97 g, 138.1 mmol) followed by hydroxylamine hydrochloride (6.40 g, 92.1 mmol) is added. The mixture is refluxed for 7 h before it is cooled to rt. The solvent is removed in vacuo. The residue is dissolved in 2 N aq. HCl and the pH is adjusted to 5 by adding 32% aq. NaOH solution. The precipitate that forms is collected, washed with water and dried under high vacuum at 40° C. for 18 h to give 3-[2-ethyl-4-(N-hydroxycarbamimidoyl)-6-methyl-phenyl]-propionic acid (11.7 g) as a beige crystalline powder; LC-MS: t_R=0.60 min, [M+1]⁺=251.09.

3-{2-Ethyl-4-[5-(6-isopropoxy-5-methyl-pyridin-3-yl)-[1,2,4]oxadiazol-3-yl]-6-methyl-phenyl}-propionic acid

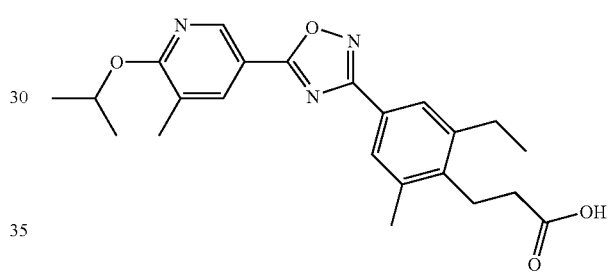

The title compound is prepared from Nicotinic acid 11 and 3-[2-ethyl-4-(N-hydroxycarbamimidoyl)-6-methyl-phenyl]-propionic acid in analogy to Example 13; LC-MS: t_R=1.15 min, [M+1]⁺=410.10.

3-Ethyl-4-hydroxy-5-methyl-benzoic acid

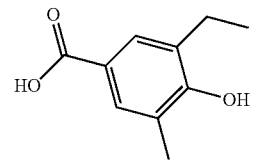

a) To an ice-cold solution of H₂SO₄ (150 mL) in water (250 mL) 2-ethyl-6-methylaniline (15.0 g, 111 mmol) is added. The solution is treated with ice (150 g) before a solution of NaNO₂ (10.7 g, 155 mmol) in water (150 mL) and ice (50 g) is added dropwise. The mixture is stirred at 0° C. for 1 h. 50% aq. H₂SO₄ (200 mL) is added and stirring is continued at rt for 18 h. The mixture is extracted with DCM, the org. extracts are dried over MgSO₄ and evaporated. The crude product is purified by CC on silica gel eluting with heptane:EA 9:1 to give 2-ethyl-6-methyl-phenol (8.6 g) as a crimson oil; LC-MS: t_R=0.89 min; ¹H NMR (CDCl₃): δ 7.03-6.95 (m, 2H), 6.80 (t, J=7.6 Hz, 1H), 4.60 (s, 1H), 2.64 (q, J=7.6 Hz, 2H), 2.25 (s, 3H), 1.24 (t, J=7.6 Hz, 3H).

b) A solution of 2-ethyl-6-methyl-phenol (8.40 g, 61.7 mmol) and hexamethylene tetraamine (12.97 g, 92.5 mmol) in acetic acid (60 mL) and water (14 mL) is heated to 115° C. The water is distilled off at 117° C. and collected with a Dean-Stark apparatus. Then the water separator is replaced by a reflux condenser and the mixture is refluxed for 3 h. The mixture is cooled to rt, diluted with water (100 mL) and extracted with EA. The org. extract is washed with sat. aq. NaHCO$_3$, dried over MgSO$_4$ and evaporated. The remaining solid is dissolved in EA and treated with heptane to initialize crystallisation. The solid material is collected and dried to give 3-ethyl-4-hydroxy-5-methyl-benzaldehyde (3.13 g) as a colourless crystalline powder, $^1$H NMR (CDCl$_3$): δ 9.83 (s, 1H), 7.58-7.53 (m, 2H), 5.30 (s br, 1H), 2.69 (q, J=7.6 Hz, 2H), 2.32 (s, 3H), 1.28 (t, J=7.6 Hz, 3H).

c) To a solution of 3-ethyl-4-hydroxy-5-methyl-benzaldehyde (78.8 g, 0.48 mol) in DMSO (585 mL), a solution of NaH$_2$PO$_4$ dihydrate (17.3 g, 0.144 mol) in water (160 mL) is added over a period of 13 min. The mixture is stirred at rt an a solution of NaClO$_2$ (65.17 g, 0.577 mol) in water (160 mL) is added while the mixture is cooled with an ice-bath. The mixture is stirred for 1 h before a second portion of NaClO$_2$ (43.44 g, 0.480 mol) in water (100 mL) is added while the temperature is kept between 25 and 40° C. with an ice-bath. Th yellow suspension is stirred at rt for 24 h before it is acidified with 32% aq. HCl to pH 2-3. The mixture is extracted with TBME (250 mL), the org. extract is washed with water, and the washings are extracted back with TBME. The solvent of the combined org. extracts is evaporated to give crude 3-ethyl-4-hydroxy-5-methyl-benzoic acid (80.3 g) as a yellow solid.

4-Allyloxy-3,5-dimethyl-benzoic acid hydrazide

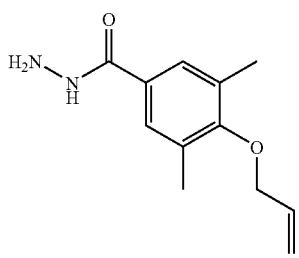

To a solution of 4-allyloxy-3,5-dimethyl-benzoic acid (Lit.: see U.S. Pat. No. 3,262,946) (5.26 g, 25.5 mmol) in CHCl$_3$ (75 mL) is added thionylchloride (7.5 mL) and the mixture is heated at reflux for 2 h. The mixture is evaporated and the residue, dissolved in DCM (50 mL), added to a cooled (0° C.) solution of 1M hydrazine in THF (75 mL) in DCM (250 mL). The mixture is slowly warmed to rt during 15 h, diluted with ether (150 mL) and washed with 1M aq. HCl (5×50 mL). The aq. extracts are washed with ether (50 mL) and the org. phases are discarded. The aq. extracts are basified with 33% aq. KOH and extracted with DCM (5×50 mL). The org. extracts are dried (Na$_2$SO$_4$), filtered and evaporated to give the title compound (5.39 g) as a white solid; LC-MS: t$_R$=0.71 min; [M+1]$^+$=221.20.

Methanesulfonic acid 2,2-dimethyl-[1,3]dioxan-5-yl methyl ester

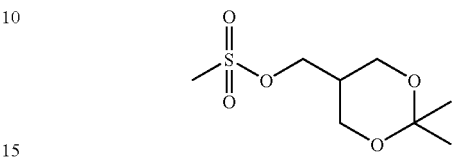

The title compound is prepared following the procedures given in B. Xu, A. Stephens, G. Kirschenheuter, A. F. Greslin, X. Cheng, J. Sennelo, M. Cattaneo, M. L. Zighetti, A. Chen, S.-A. Kim, H. S. Kim, N. Bischofberger, G. Cook, K. A. Jacobson, J. Med. Chem. 45 (2002) 5694-5709.

SYNTHESIS OF EXAMPLES

Example 1

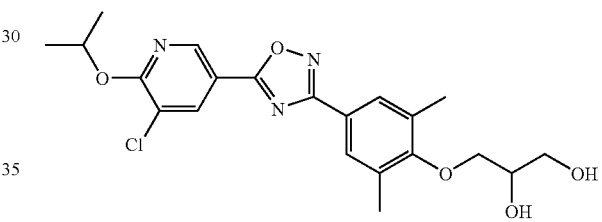

a) A solution of 5-chloro-6-isopropoxy-nicotinic acid (202.9 mg, 0.94 mmol), TBTU (332 mg, 1.04 mmol), Hünig's base (607 mg, 4.70 mmol), and 4-allyloxy-N-hydroxy-3,5-dimethyl-benzamidine (230 mg, 1.04 mmol) in DCM (7 mL) is stirred at rt for 24 h. The mixture is diluted with ether (150 mL), washed with 1N aq. HCl (2×20 mL), 1N aq. KHSO$_4$ solution (20 mL) and brine (20 mL), dried over Na$_2$SO$_4$, filtered and concentrated. The crude product is purified by MPLC on silica gel eluting with a gradient of EA in heptane to give 5-chloro-6-isopropoxy-nicotinic acid (4-allyloxy-N-hydroxy-3,5-dimethyl-benzamidine) ester (258 mg) as a white powder; LC-MS: t$_R$=1.12 min, [M+1]$^+$=418.07.

b) A solution of 5-chloro-6-isopropoxy-nicotinic acid (4-allyloxy-N-hydroxy-3,5-dimethyl-benzamidine) ester (200 mg, 0.48 mmol) in dioxane (6 mL) is stirred at 90° C. for 2 days. The solvent is evaporated to give crude 3-[3-(4-allyloxy-3,5-dimethyl-phenyl)-[1,2,4]oxadiazol-5-yl]-5-chloro-6-isopropoxy-pyridine (279 mg); LC-MS: t$_R$=1.27 min.

c) To a solution of 3-[3-(4-allyloxy-3,5-dimethyl-phenyl)-[1,2,4]oxadiazol-5-yl]-5-chloro-6-isopropoxy-pyridine (191 mg, 0.48 mmol) in acetone (10 mL) and water (1 mL), NMO (97 mg, 0.72 mmol) followed by OsO$_4$ (12 mg, 0.048 mmol) are added. The mixture is stirred at 45° C. for 16 h before it is diluted with 1N aq. KHSO$_4$-solution and extracted with ether (3×50 mL). The combined org. extracts are dried over Na$_2$SO$_4$, filtered and concentrated. A sample (15 mg) of the crude product (299 mg) is purified by chromatography on prep. TLC plates with heptane:EA 1:2 to give (RS)-3-{4-[5-(5-chloro-6-isopropoxy-pyridin-3-yl)-[1,2,4]oxadiazol-3- yl]-2,6-dimethyl-phenoxy}-propane-1,2-diol (10.6 mg); LC-MS: $t_R$=1.06 min, [M+1]⁺=434.06.

Example 2

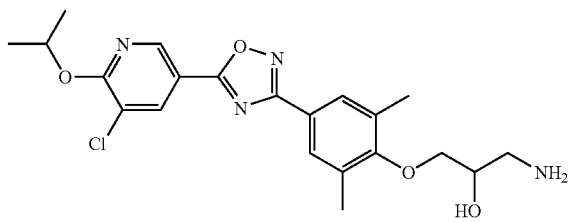

To a solution of crude (RS)-3-{4-[5-(5-chloro-6-isopropoxy-pyridin-3-yl)-[1,2,4]oxadiazol-3-yl]-2,6-dimethyl-phenoxy}-propane-1,2-diol (265 mg, 0.61 mmol) in THF (5 mL), Hünig's base (158 mg, 1.22 mmol) followed by methanesulfonylchloride (77 mg, 0.67 mmol) are added at 0° C. The mixture is stirred at rt for 16 h before 7 M NH₃ in MeOH (2 mL) is added. The mixture is stirred at 65° C. for 16 h before the solvent is removed in vacuo to give crude (RS)-1-amino-3-{4-[5-(5-chloro-6-isopropoxy-pyridin-3-yl)-[1,2,4]oxadiazol-3-yl]-2,6-dimethyl-phenoxy}-propan-2-01; LC-MS: $t_R$=0.92 min, [M+1+CH₃CN]⁺=474.44.

Example 3

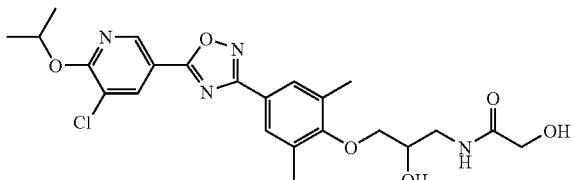

To a solution of (RS)-1-amino-3-{4-[5-(5-chloro-6-isopropoxy-pyridin-3-yl)-[1,2,4]oxadiazol-3-yl]-2,6-dimethyl-phenoxy}-propan-2-ol (313 mg, 0.6 mmol) in DCM (10 mL), glycolic acid (95 mg, 1.25 mmol) and Hünig's base (233 mg, 1.8 mmol) are added. The mixture is cooled to 0° C. and TBTU (236 mg, 0.74 mmol) is added. The mixture is stirred at 0° C. for 1 h, then at rt for 16 h before it is diluted with EA (250 mL), washed with 1N aq. NaOH solution (3×25 mL), 1N aq. KHSO₄ (25 mL) and brine (25 mL), dried over Na₂SO₄, filtered and concentrated. The crude product is purified by prep. HPLC to give N—((RS)-3-{4-[5-(5-chloro-6-isopropoxy-pyridin-3-yl)-[1,2,4]oxadiazol-3-yl]-2,6-dimethyl-phenoxy}-2-hydroxy-propyl)-2-hydroxy-acetamide (42 mg) as a white powder; LC-MS: $t_R$=1.06 min; [M+1]⁺=491.48; ¹H NMR (CD3OD) δ 1.45 (d, J=6.3 Hz, 6H), 2.38 (s, 6H), 3.47 (dd, J=13.6, 7.3 Hz, 1H), 3.66 (dd, J=13.6, 4.5 Hz, 1H), 3.87 (m, 2H), 4.04 (s, 2H), 4.14 (m, 1H), 5.52 (m, 1H), 7.78 (s, 2H), 8.43 (s, 1H), 8.85 (s, 1H)

Example 4

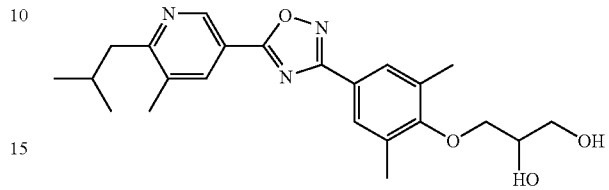

(RS)-3-{4-[5-(6-Isobutyl-5-methyl-pyridin-3-yl)-[1,2,4]oxadiazol-3-yl]-2,6-dimethyl-phenoxy}-propane-1,2-diol is prepared in analogy to Example 1; LC-MS: $t_R$=0.92 min, [M+1]⁺=412.21.

Example 5

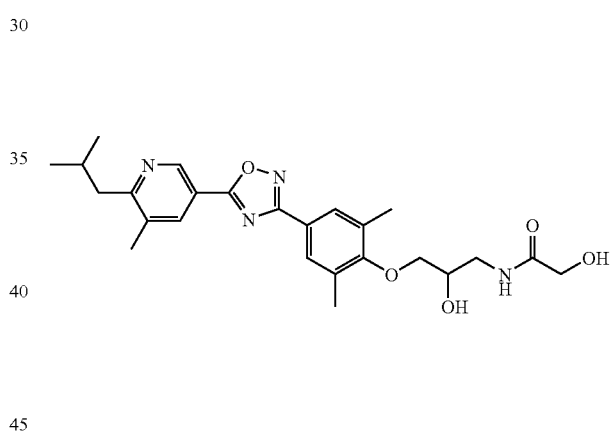

2-Hydroxy-N—((RS)-2-hydroxy-3-{4-[5-(6-isobutyl-5-methyl-pyridin-3-yl)-[1,2,4]oxadiazol-3-yl]-2,6-dimethyl-phenoxy}-propyl)-acetamide is prepared in analogy to Example 2 and 3; LC-MS: $t_R$=0.89 min, [M+1]⁺=469.57.

Example 6

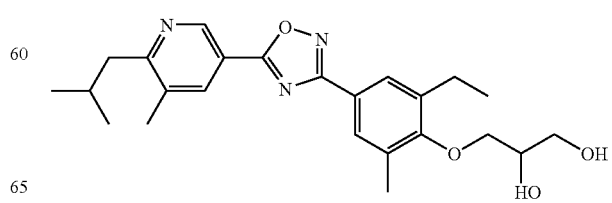

(RS)-3-{2-Ethyl-4-[5-(6-isobutyl-5-methyl-pyridin-3-yl)-[1,2,4]oxadiazol-3-yl]-6-methyl-phenoxy}-propane-1,2-diol is prepared in analogy to Example 1; LC-MS: $t_R$=0.95 min, [M+1]$^+$=426.14.

Example 7

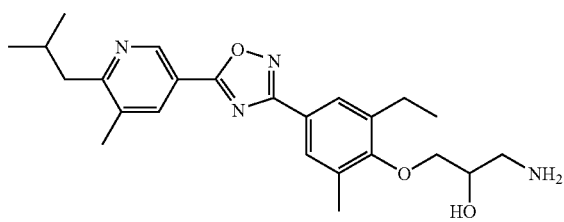

(RS)-1-Amino-3-{2-ethyl-4-[5-(6-isobutyl-5-methyl-pyridin-3-yl)-[1,2,4]oxadiazol-3-yl]-6-methyl-phenoxy}-propan-2-ol is prepared in analogy to Example 2; LC-MS: $t_R$=0.82 min, [M+1]$^+$=425.17.

Example 8

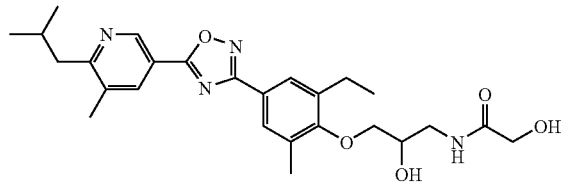

N—((RS)-3-{2-Ethyl-4-[5-(6-isobutyl-5-methyl-pyridin-3-yl)-[1,2,4]oxadiazol-3-yl]-6-methyl-phenoxy}-2-hydroxy-propyl)-2-hydroxy-acetamide is prepared in analogy to Example 3; LC-MS: $t_R$=0.91 min, [M+1]$^+$=483.21.

Example 9

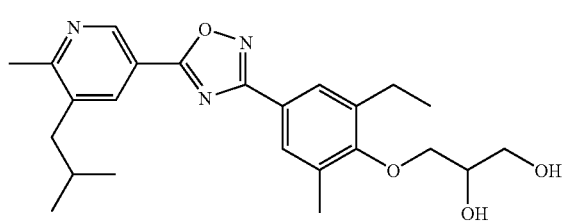

(RS)-3-{2-Ethyl-4-[5-(5-isobutyl-6-methyl-pyridin-3-yl)-[1,2,4]oxadiazol-3-yl]-6-methyl-phenoxy}-propane-1,2-diol is prepared in analogy to Example 1; LC-MS: $t_R$=0.96 min, [M+1]$^+$=426.12.

Example 10

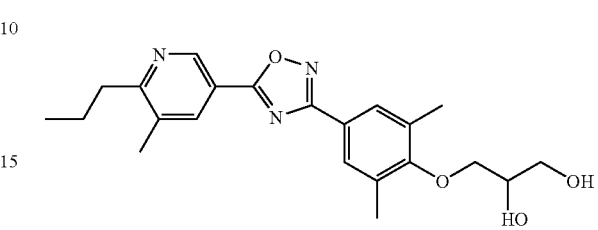

(RS)-3-{2,6-Dimethyl-4-[5-(5-methyl-6-propyl-pyridin-3-yl)-[1,2,4]oxadiazol-3-yl]-phenoxy}-propane-1,2-diol is prepared in analogy to Example 1; LC-MS: $t_R$=0.87 min, [M+1]$^+$=398.54.

Example 11

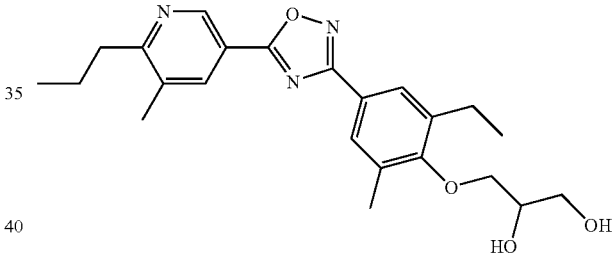

(RS)-3-{2-Ethyl-6-methyl-4-[5-(5-methyl-6-propyl-pyridin-3-yl)-[1,2,4]oxadiazol-3-yl]-phenoxy}-propane-1,2-diol is prepared in analogy to Example 1; LC-MS: $t_R$=0.91 min, [M+1]$^+$=412.56.

Example 12

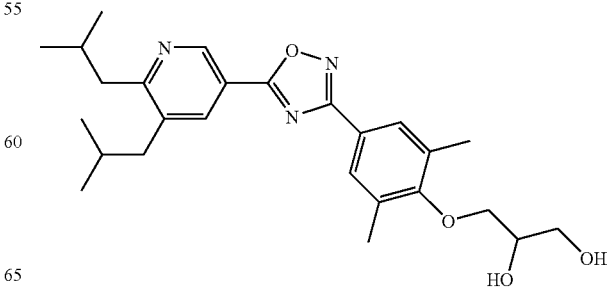

(RS)-3-{4-[5-(5,6-Diisobutyl-pyridin-3-yl)-[1,2,4]oxadiazol-3-yl]-2,6-dimethyl-phenoxy}-propane-1,2-diol is prepared in analogy to Example 1; LC-MS: $t_R$=1.01 min; [M+1]$^+$=454.56.

Example 13

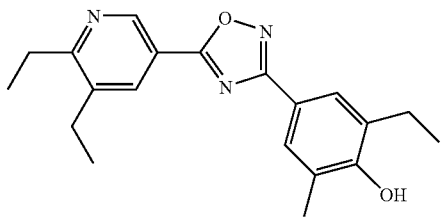

To a solution of 5,6-diethyl-nicotinic acid hydrochloride (920 mg, 4.3 mmol) and Hünig's base (2.76 g, 21 mmol) in DCM (50 mL) is added TBTU (1.785 g, 5.55 mmol) and the mixture is stirred at rt for 5 min. 3-Ethyl-4,N-dihydroxy-5-methyl-benzamidine (1.14 g, 4.7 mmol) is added and the mixture stirred for 0.5 h. The mixture is diluted with DCM, washed with sat. aq. NaHCO$_3$ solution, dried over MgSO$_4$, filtered and concentrated. The crude 5,6-diethyl-nicotinic acid (3-ethyl-4,N-dihydroxy-5-methyl-benzamidine) ester (LC-MS: $t_R$=0.79 min) is dissolved in dioxane (50 mL) and heated to 100° C. for 18 h. The solvent is evaporated and the crude product is purified by FC on silica gel eluting with heptane:EA 10:1 to give 4-[5-(5,6-diethyl-pyridin-3-yl)-[1,2,4]oxadiazol-3-yl]-2-ethyl-6-methyl-phenol (0.42 g) as a solid; LC-MS: $t_R$=1.03 min, [M+1]$^+$=338.09.

Example 14

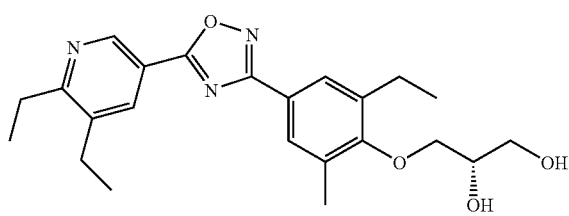

To a solution of 4-[5-(5,6-diethyl-pyridin-3-yl)-[1,2,4]oxadiazol-3-yl]-2-ethyl-6-methyl-phenol (100 mg, 0.296 mmol) in isopropanol (10 mL) and 3 N aq. NaOH (3 mL), (S)-3-chloro-1,2-propanediol (98 mg, 0.89 mmol) is added. The mixture is stirred at 60° C. for 24 h before another portion of (S)-3-chloro-1,2-propanediol (98 mg, 0.89 mmol) is added. Stirring is continued at 60° C. for 2 days. The mixture is diluted with EA and washed with sat. aq. NaHCO$_3$ solution. The org. extract is dried over MgSO$_4$, filtered and evaporated. The crude product is purified by chromatography on prep. TLC plates with EA-heptane to give (S)-3-{4-[5-(5,6-diethyl-pyridin-3-yl)-[1,2,4]oxadiazol-3-yl]-2-ethyl-6-methyl-phenoxy}-propane-1,2-diol (14 mg) as a red oil; LC-MS: $t_R$=0.93 min, [M+1]$^+$=412.16.

Example 15

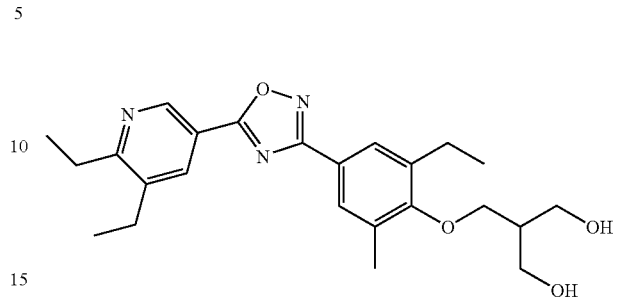

2-{4-[5-(5,6-Diethyl-pyridin-3-yl)-[1,2,4]oxadiazol-3-yl]-2-ethyl-6-methyl-phenoxymethyl}-propane-1,3-diol is prepared in two steps in analogy to Example 14 using methanesulfonic acid 2,2-dimethyl-[1,3]dioxan-5-ylmethyl ester as the alkylating agent. The obtained protected diol (32 mg) is dissolved in THF (5 mL) and water (0.5 mL) and TFA (0.25 mL) are added. The mixture is stirred at rt for 1 h, diluted with EA and washed with sat. aq. NaHCO$_3$. The org. phase is evaporated and the residue purified by chromatography on prep. TLC plates with DCM-MeOH to give 2-{4-[5-(5,6-diethyl-pyridin-3-yl)-[1,2,4]oxadiazol-3-yl]-2-ethyl-6-methyl-phenoxymethyl}-propane-1,3-diol; LC-MS: $t_R$=0.95 min, [M+1]$^+$=426.09.

Example 16

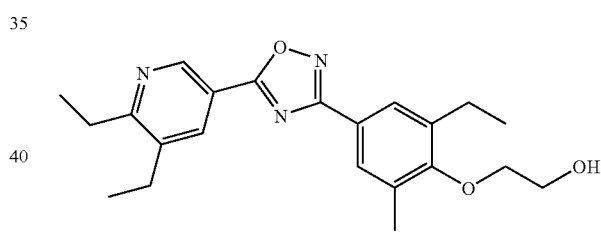

2-{4-[5-(5,6-Diethyl-pyridin-3-yl)-[1,2,4]oxadiazol-3-yl]-2-ethyl-6-methyl-phenoxy}-ethanol is prepared in analogy to Example 14 using bromoethanol as the alkylating agent; LC-MS: $t_R$=1.01 min; [M+1]$^+$=382.17; $^1$H NMR (CDCl$_3$) δ 1.22-1.45 (m, 9H), 2.42 (s, 3H), 2.72-2.87 (m, 4H), 2.96 (q, J=7.5 Hz, 2H), 4.00 (m, 5H), 7.89 (s, 1H), 7.90 (s, 1H), 8.24 (s, 1H), 9.21 (s, 1H).

Example 17

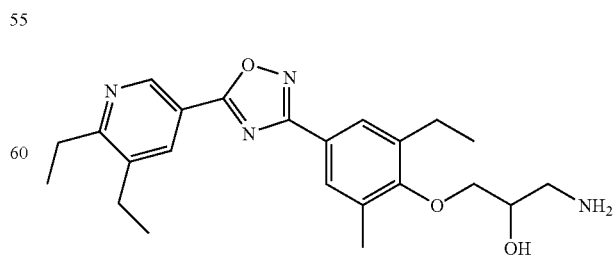

a) To a solution of 4-[5-(5,6-diethyl-pyridin-3-yl)-[1,2,4]oxadiazol-3-yl]-2-ethyl-6-methyl-phenol (150 mg, 0.445 mmol) in isopropanol (10 mL) and 3 N aq. NaOH (3 mL), epichlorhydrine (164 mg, 1.78 mmol) is added. The mixture is stirred at rt for 20 h. The mixture is diluted with EA and washed with sat. aq. NaHCO$_3$ solution. The org. extract is dried over MgSO$_4$, filtered and evaporated. The crude product is purified by chromatography on prep. TLC plates with EA-heptane to give (RS)-2,3-diethyl-5-[3-(3-ethyl-5-methyl-4-oxiranylmethoxy-phenyl)-[1,2,4]oxadiazol-5-yl]-pyridine (92 mg) as an oil.

b) (RS)-2,3-Diethyl-5-[3-(3-ethyl-5-methyl-4-oxiranyl methoxy-phenyl)-[1,2,4]oxadiazol-5-yl]-pyridine (92 mg) is dissolved in 7N NH$_3$ in MeOH (20 mL) and heated in a screw cap bottle at 60° C. for 15 h. The mixture is evaporated to give crude (RS)-1-amino-3-{4-[5-(5,6-diethyl-pyridin-3-yl)-[1,2,4]oxadiazol-3-yl]-2-ethyl-6-methyl-phenoxy}-propan-2-ol (99 mg); LC-MS: $t_R$=0.80 min, [M+1]$^+$=411.09.

Example 18

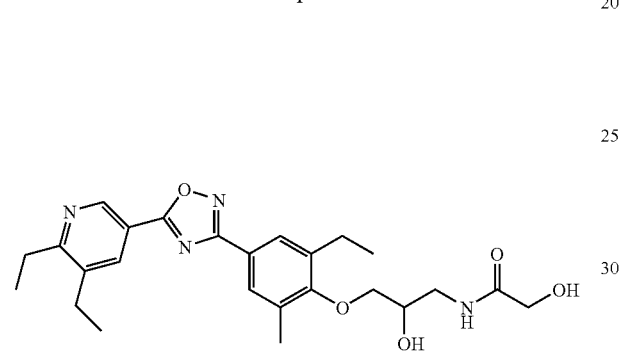

To a solution of (RS)-1-amino-3-{4-[5-(5,6-diethyl-pyridin-3-yl)-[1,2,4]oxadiazol-3-yl]-2-ethyl-6-methyl-phenoxy}-propan-2-ol (99 mg, 0.24 mmol), glycolic acid (18.5 mg, 0.244 mmol) and Hünig's base (78 mg, 0.61 mmol) in DCM (5 mL) is added PyBOP (126.7 mg, 0.24 mmol) and the mixture is stirred at rt for 30 min. The mixture is diluted with EA, washed with sat. aq. NaHCO$_3$ solution, dried over MgSO$_4$, filtered and concentrated. The crude product is purified by chromatography on prep. TLC plates eluting with DCM:MeOH 10:1 to give N—((RS)-3-{4-[5-(5,6-diethyl-pyridin-3-yl)-[1,2,4]oxadiazol-3-yl]-2-ethyl-6-methyl-phenoxy}-2-hydroxy-propyl)-2-hydroxy-acetamide (90 mg) as an oil; LC-MS: $t_R$=0.88 min, [M+1]$^+$=469.25.

Example 19

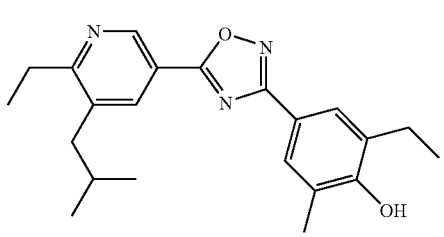

2-Ethyl-4-[5-(6-ethyl-5-isobutyl-pyridin-3-yl)-[1,2,4]oxadiazol-3-yl]-6-methyl-phenol is prepared in analogy to Example 13; LC-MS: $t_R$=1.09 min, [M+1]$^+$=366.19.

Example 20

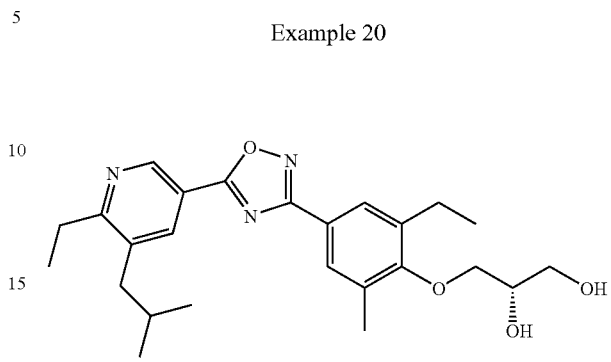

(S)-3-{2-Ethyl-4-[5-(6-ethyl-5-isobutyl-pyridin-3-yl)-[1,2,4]oxadiazol-3-yl]-6-methyl-phenoxy}-propane-1,2-diol is prepared in analogy to Example 14; LC-MS: $t_R$=1.00 min, [M+1]$^+$=440.20.

Example 21

(S)-2-{2-Ethyl-4-[5-(6-ethyl-5-isobutyl-pyridin-3-yl)-[1,2,4]oxadiazol-3-yl]-6-methyl-phenoxy}-ethanol is prepared in analogy to Example 16; LC-MS: $t_R$=1.08 min, [M+1]$^+$=410.15.

Example 22

(RS)-1-Amino-3-{2-ethyl-4-[5-(6-ethyl-5-isobutyl-pyridin-3-yl)-[1,2,4]oxadiazol-3-yl]-6-methyl-phenoxy}-propan-2-ol is prepared in analogy to Example 17; LC-MS: $t_R$=0.85 min, [M+1]$^+$=439.17.

Example 23

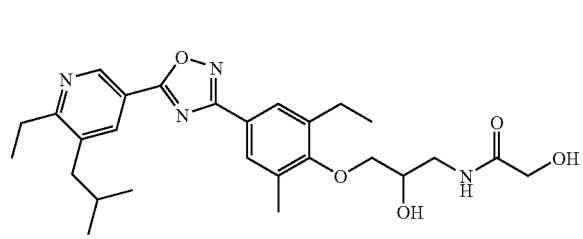

N—((RS)-3-{2-Ethyl-4-[5-(6-ethyl-5-isobutyl-pyridin-3-yl)-[1,2,4]oxadiazol-3-yl]-6-methyl-phenoxy}-2-hydroxy-propyl)-2-hydroxy-acetamide is prepared in analogy to Example 18; LC-MS: $t_R$=0.95 min, [M+1]$^+$=497.17.

Example 24

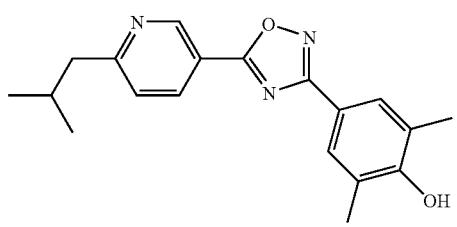

4-[5-(6-Isobutyl-pyridin-3-yl)-[1,2,4]oxadiazol-3-yl]-2,6-dimethyl-phenol is prepared in analogy to Example 13; LC-MS: $t_R$=1.04 min, [M+1]$^+$=324.36.

Example 25

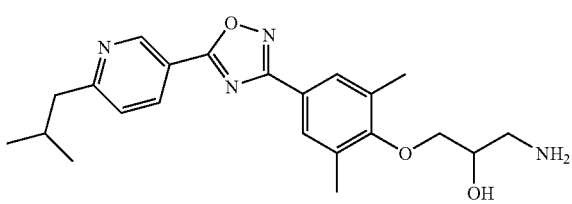

(RS)-1-Amino-3-{4-[5-(6-isobutyl-pyridin-3-yl)-[1,2,4]oxadiazol-3-yl]-2,6-dimethyl-phenoxy}-propan-2-ol is prepared in analogy to Example 17; LC-MS: $t_R$=0.8 min.

Example 26

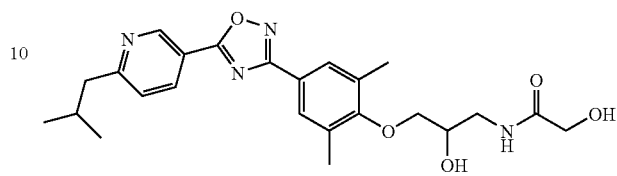

2-Hydroxy-N—((RS)-2-hydroxy-3-{4-[5-(6-isobutyl-pyridin-3-yl)-[1,2,4]oxadiazol-3-yl]-2,6-dimethyl-phenoxy}-propyl)-acetamide is prepared in analogy to Example 18; LC-MS: $t_R$=0.89 min, [M+1]$^+$=455.48.

Example 27

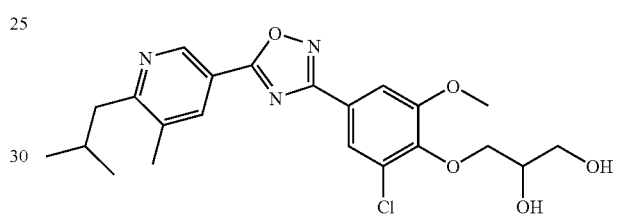

(RS)-3-{2-Chloro-4-[5-(6-isobutyl-5-methyl-pyridin-3-yl)-[1,2,4]oxadiazol-3-yl]-6-methoxy-phenoxy}-propane-1,2-diol is prepared in analogy to Example 1; LC-MS: $t_R$=0.94 min, [M+1]$^+$=448.21.

Example 28

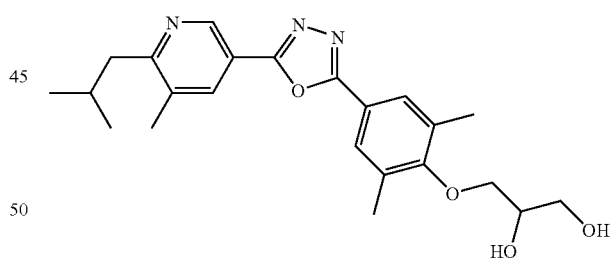

a) To a solution of 6-isobutyl-5-methyl-nicotinic acid hydrochloride (50 mg, 0.22 mmol), DIPEA (0.12 mL, 0.7 mmol) and TBTU (97 mg, 0.30 mmol) in DCM (5 mL) is added at 0° C. 4-allyloxy-3,5-dimethyl-benzoic acid hydrazide (50.6 mg, 0.23 mmol) and the mixture is stirred at 0° C. for 4 h. The mixture is diluted with EA (15 mL) and washed with 1M aq. NaH$_2$PO$_4$ (5 mL), 1M aq. NaOH (5 mL) and water (5 mL). The org. phase is dried (MgSO$_4$), filtered and evaporated to provide 6-isobutyl-5-methyl-nicotinic acid N'-(4-allyloxy-3,5-dimethyl-benzoyl)-hydrazide (85 mg); LC-MS: $t_R$=0.81 min, [M+1]$^+$=396.20.

b) A solution of 6-isobutyl-5-methyl-nicotinic acid N'-(4-allyloxy-3,5-dimethyl-benzoyl)-hydrazide (89 mg, 0.224 mmol) and Burgess reagent (162 mg, 0.68 mmol) in THF (4 mL) is heated in a microwave oven at 110° C. for 6 min. The mixture is diluted with EA (15 mL) and washed with 1M aq. NaH$_2$PO$_4$ (5 mL), 1M aq. NaOH (5 mL) and water (5 mL). The org. phase is dried (MgSO$_4$), filtered and evaporated to provide crude 5-[5-(4-allyloxy-3,5-dimethyl-phenyl)-[1,3,4] oxadiazol-2-yl]-2-isobutyl-3-methyl-pyridine (80 mg); LC-MS: $t_R$=1.07 min, [M+1]$^+$=378.3.

c) (RS)-3-{4-[5-(6-Isobutyl-5-methyl-pyridin-3-yl)-[1,3, 4]oxadiazol-2-yl]-2,6-dimethyl-phenoxy}-propane-1,2-diol is prepared from 5-[5-(4-allyloxy-3,5-dimethyl-phenyl)-[1, 3,4]oxadiazol-2-yl]-2-isobutyl-3-methyl-pyridine in analogy to Example 1; LC-MS: $t_R$=0.83 min; [M+1]$^+$=412.23; $^1$H NMR (D$_6$-DMSO) δ 0.94 (d, J=6.5 Hz, 6H), 2.19 (hept, J=6.5 Hz, 1H), 2.36 (s, 6H), 2.42 (s, 3H), 2.73 (d, J=7.3 Hz, 2H), 3.50 (t, J=5.5 Hz, 2H), 3.76 (m, 1H), 3.84 (m, 1H), 3.89 (m, 1H), 4.65 (t, J=5.5 Hz, 1H), 4.97 (d, J=5.0 Hz, 1H), 7.84 (s, 2H), 8.24 (d, J=1.0 Hz, 1H), 9.05 (d, J=1.5 Hz, 1H).

Example 29

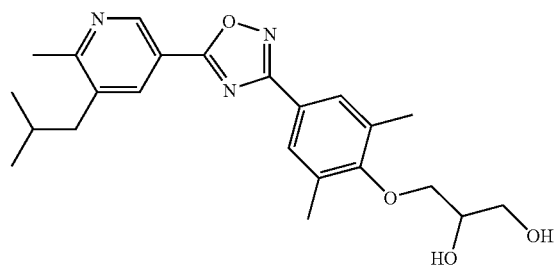

Starting from nicotinic acid 2, (RS)-3-{4-[5-(5-isobutyl-6-methyl-pyridin-3-yl)-[1,2,4]oxadiazol-3-yl]-2,6-dimethyl-phenoxy}-propane-1,2-diol is prepared in analogy to Example 1; LC-MS: $t_R$=0.93 min; [M+1]$^+$=412.18.

Examples 30 to 34

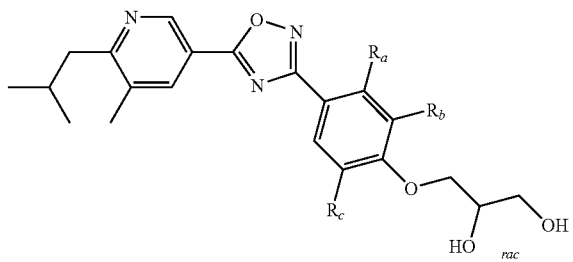

The following examples are prepared in analogy to Example 1 starting from nicotinic acid 6.

|  |  |  |  | LC-MS | |
|---|---|---|---|---|---|
| Example | R$_a$ | R$_b$ | R$_c$ | $t_R$ [min] | [M + H]$^+$ |
| 30 | H | H | H | 0.83 | 384.50 |
| 31 | CH$_3$ | H | H | 0.86 | 398.48 |
| 32 | H | OCH$_3$ | H | 0.75 | 414.20 |
| 33 | H | Br | H | 0.93 | 462.20 |
| 34 | H | CH$_3$ | Cl | 0.95 | 432.26 |

Example 34

$^1$H NMR (CDCl$_3$): δ1.01 (d, J=6.8 Hz, 6H), 2.18-2.31 (m, 1H), 2.45 (s, 3H), 2.46 (s, 3H), 2.80 (d, J=7.3 Hz, 2H), 3.82-3.96 (m, 2H), 4.06-4.13 (m, 2H), 4.15-4.23 (m, 1H), 7.95 (d, J=0.8 Hz, 1H), 8.09 (d, J=1.5 Hz, 1H), 8.21 (s, 1H), 9.19 (s, 1H).

Examples 35 to 39

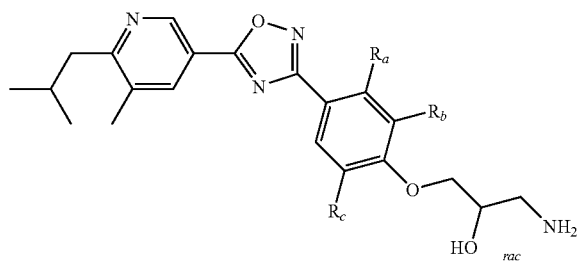

The following examples are prepared from previous examples in analogy to Example 2.

|  |  |  |  | LC-MS | |
|---|---|---|---|---|---|
| Example | R$_a$ | R$_b$ | R$_c$ | $t_R$ [min] | [M + H]$^+$ |
| 35 | CH$_3$ | H | H | 0.78 | 397.07 |
| 36 | H | OCH$_3$ | H | 0.68 | 413.17 |
| 37 | H | CH$_3$ | Cl | 0.82 | 431.49 |
| 38 | H | OCH$_3$ | Cl | 0.81 | 447.15 |
| 39 | H | CH$_3$ | CH$_3$ |  |  |

Examples 40 to 43

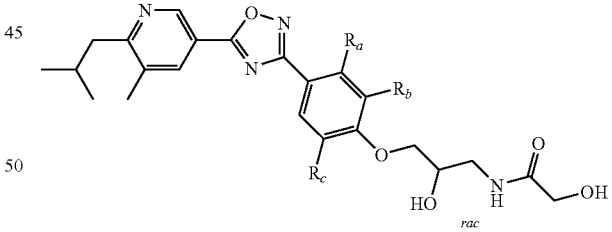

The following examples are prepared from previous examples in analogy to Example 3.

|  |  |  |  | LC-MS | |
|---|---|---|---|---|---|
| Example | R$_a$ | R$_b$ | R$_c$ | $t_R$ [min] | [M + H]$^+$ |
| 40 | CH$_3$ | H | H | 0.84 | 455.45 |
| 41 | H | OCH$_3$ | H | 0.73 | 471.22 |
| 42 | H | CH$_3$ | Cl | 0.90 | 489.20 |
| 43 | H | OCH$_3$ | Cl | 0.90 | 505.16 |

Example 40

$^1$H NMR (CDCl$_3$): δ1.01 (d, J=6.5 Hz, 6H), 2.17-2.30 (m, 1H), 2.46 (s, 3H), 2.68 (s, 3H), 2.80 (d, J=7.3 Hz, 2H), 3.13-3.19 (m, 1H), 3.47-3.56 (m, 1H), 3.72-3.80 (m, 1H), 3.99-4.08 (m, 2H), 4.17-4.24 (m, 3H), 6.85-6.90 (m, 2H), 7.08 (t br, J=5.5 Hz, 1H), 8.06 (d, J=8.3 Hz, 1H), 8.21 (s, 1H), 9.20 (s, 1H)

Example 44

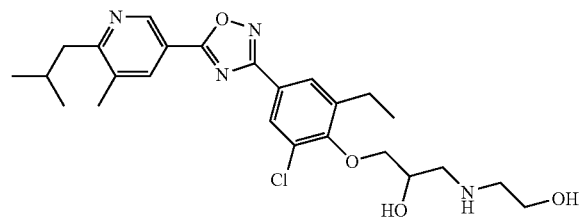

(RS)-1-{2-Chloro-4-[5-(6-isobutyl-5-methyl-pyridin-3-yl)-[1,2,4]oxadiazol-3-yl]-6-methoxy-phenoxy}-3-(2-hydroxy-ethylamino)-propan-2-ol is prepared from Example 27 in analogy to Example 2 by reacting the methansulfonylated intermediate with ethanolamine, LC-MS: t$_R$=0.82 min, [M+1]$^+$=491.06; $^1$H NMR (CDCl$_3$): δ1.00 (d, J=6.5 Hz, 6H), 2.18-2.29 (m, 1H), 2.46 (s, 3H), 2.79 (d, J=7.3 Hz, 2H), 2.83-2.92 (m, 4H), 3.68-3.73 (m, 2H), 4.01 (s, 3H), 4.04-4.16 (m, 2H), 4.24-4.31 (m, 1H), 7.64 (s, 1H), 7.87 (s, 1H), 8.21 (s, 1H), 9.18 (s, 1H).

Examples 45 and 46

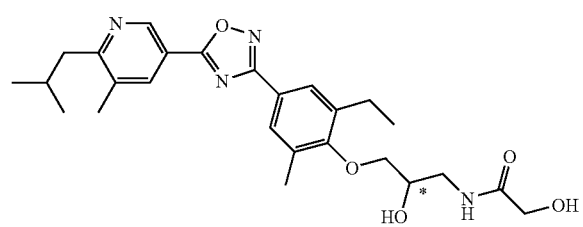

The racemic compound of Example 8 is resolved into pure enantiomers by prep. HPLC on a chiral stationary phase (ChiralPak ADH 4.6×250 mm, 5 µm, 20% EtOH containing 0.1% diethylamine in heptane, 40 min, flow: 0.8 mL/min).

| Example | *Chirality | Retention time [min] |
|---|---|---|
| 45 | R | 13.5 |
| 46 | S | 11.8 |

Example 47

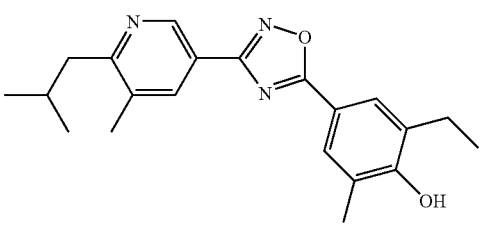

2-Ethyl-4-[3-(6-isobutyl-5-methyl-pyridin-3-yl)-[1,2,4]oxadiazol-5-yl]-6-methyl-phenol is prepared from N-hydroxy-6-isobutyl-5-methyl-nicotinamidine and 3-ethyl-4-hydroxy-5-methyl-benzoic acid in analogy to Example 13, LC-MS: t$_R$=1.02 min, [M+1]$^+$=352.09.

Examples 48 to 53

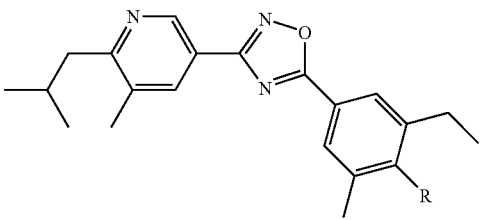

Starting from Example 47, the following examples are prepared in analogy to previous examples.

| | in analogy to | | LC-MS | |
|---|---|---|---|---|
| Example | Example | R | t$_R$ [min] | [M + H]$^+$ |
| 48 | 14 | ![structure](O^OH with OH) | 0.99 | 425.82 |
| 49 | 14 | ![structure](O^OH with OH) | 0.99 | 425.90 |
| 50 | 17 | ![structure](O^NH$_2$ with OH) | 0.74 | 425.08 |

| in analogy to | | | LC-MS | |
|---|---|---|---|---|
| Example | Example | R | $t_R$ [min] | $[M + H]^+$ |
| 51 | 17 | ![structure] O-CH2-CH(OH)-CH2-NH2 | 0.74 | 425.24 |
| 52 | 18 | ![structure] O-CH2-CH(OH)-CH2-NH-C(O)-CH2-OH | 0.92 | 483.12 |
| 53 | 18 | ![structure] O-CH2-CH(OH)-CH2-NH-C(O)-CH2-OH | 0.92 | 483.07 |

Example 49

$^1$H NMR (CDCl$_3$): δ 1.00 (d, J=6.3 Hz, 6H), 1.33 (t, J=7.3 Hz, 3H), 2.17-2.27 (m, 2H), 2.43 (s, 6H), 2.79 (m, 4H), 2.90 (s br, 1H), 3.82-4.01 (m, 4H), 4.15-4.24 (m, 1H), 7.93 (s, 1H), 7.94 (s, 1H), 8.18 (s, 1H), 9.15 (s, 1H).

Example 53

$^1$H NMR (CDCl$_3$): δ 1.01 (d, J=6.5 Hz, 6H), 1.33 (t, J=7.3 Hz, 3H), 2.16-2.28 (m, 1H), 2.41 (s, 3H), 2.44 (s, 3H), 2.74-2.82 (m, 4H), 3.39 (s br, 1H), 3.49-3.58 (m, 1H), 3.77-3.95 (m, 3H), 4.20-4.27 (m, 3H), 7.01 (s br, 1H), 7.93 (s, 1H), 7.94 (s, 1H), 8.19 (s, 1H), 9.15 (s, 1H).

Example 54

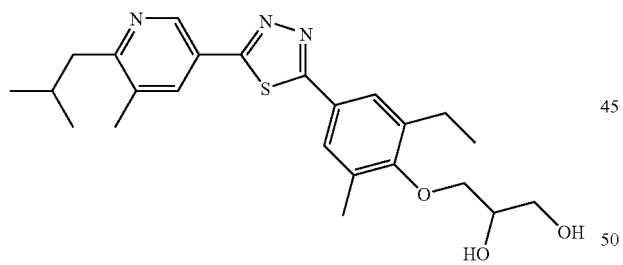

a) To a solution of nicotinic acid 6 (50 mg, 0.218 mmol) in DCM (5 mL), a solution of TBTU (97 mg, 0.301 mmol) followed by DIPEA (90 mg, 0.696 mmol) in DCM (5 mL) is added. The mixture is stirred and cooled to 0° C. before 4-allyloxy-3,5-dimethyl-benzoic acid hydrazide (51 mg, 0.232 mmol) is added. The mixture is stirred at 0° C. for 16 h before it is diluted with EA (15 mL), washed with sat. aq. NaHCO$_3$ solution (5 mL) and 1M aq. NaOH (5 mL), dried over MgSO$_4$, filtered and concentrated and dried under vacuum to give the hydrazide intermediate; LC-MS: $t_R$=0.81 min, $[M+1]^+$=396.37. To a solution of this material in THF (3 mL), Lawesson's reagent (129 mg, 0.318 mmol) is added and the mixture is heated in the microwave at 110° C. for 5 min. The mixture is diluted with EA (30 mL), washed with sat. aq. Na$_2$CO$_3$ solution, dried over Na$_2$SO$_4$, filtered and concentrated. The crude product is purified on prep. TLC plates with DCM containing 10% of 7 N NH$_3$ in MeOH to give 5-[5-(4-allyloxy-3,5-dimethyl-phenyl)-[1,3,4]thiadiazol-2-yl]-2-isobutyl-3-methyl-pyridine (67 mg) as a yellow solid, LC-MS: $t_R$=1.04 min, $[M+1]^+$=394.10.

b) 5-[5-(4-Allyloxy-3,5-dimethyl-phenyl)-[1,3,4]thiadiazol-2-yl]-2-isobutyl-3-methyl-pyridine is treated with OsO$_4$ as described in step c) of Example 1 to give (RS)-3-{4-[5-(6-isobutyl-5-methyl-pyridin-3-yl)-[1,3,4]thiadiazol-2-yl]-2,6-dimethyl-phenoxy}-propane-1,2-diol; LC-MS: $t_R$=0.78 min, $[M+1]^+$=428.50; $^1$H NMR (CDCl$_3$): δ 1.01 (d, J=6.5 Hz, 6H), 2.17-2.28 (m, 1H), 2.39 (s, 6H), 2.43 (s, 3H), 2.76 (d, J=7.3 Hz, 2H), 3.82-3.99 (m, 4H), 4.14-4.21 (m, 1H), 7.70 (s, 2H), 8.13 (s, 1H), 8.90 (s, 1H).

Example 55

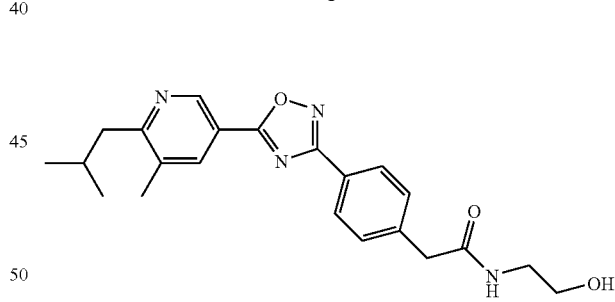

To a solution of {4-[5-(6-isobutyl-5-methyl-pyridin-3-yl)-[1,2,4]oxadiazol-3-yl]-phenyl}-acetic acid (50 mg, 142 µmol) in DMF (3 mL), EDC HCl (33 mg, 171 µmol), HOBt (23 mg, 171 µmol) and DIPEA (28 mg, 213 µmol) is added. The mixture is stirred at rt for 5 min before ethanolamine (10 mg, 157 µmol) is added. Stirring is continued at rt for 72 h. The mixture is diluted with EA, washed with water, and concentrated. The crude product is purified on prep. TLC plates with DCM containing 10% of MeOH to give N-(2-hydroxy-ethyl)-2-{4-[5-(6-isobutyl-5-methyl-pyridin-3-yl)-[1,2,4]oxadiazol-3-yl]-phenyl}-acetamide (26 mg) as a white solid; LC-MS: $t_R$=0.82 min, $[M+1]^+$=395.15; $^1$H NMR (CDCl$_3$): δ 1.01 (d, J=6.5 Hz, 6H), 2.19-2.29 (m, 1H), 2.46 (s, 3H), 2.53 (s br, 1H), 2.80 (d, J=7.3 Hz, 2H), 3.44 (q, J=4.8 Hz, 2H), 3.69 (s, 2H), 3.71-3.75 (m, 2H), 5.96 (s br, 1H), 7.46 (d, J=7.5 Hz, 2H), 8.18 (d, J=7.8 Hz, 2H), 8.17 (s), 8.19 (s), 8.22 (s, 1H), 9.20 (s, 1H).

Example 56

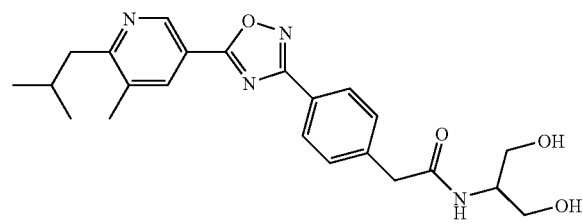

N-(2-Hydroxy-1-hydroxymethyl-ethyl)-2-{4-[5-(6-isobutyl-5-methyl-pyridin-3-yl)-[1,2,4]oxadiazol-3-yl]-phenyl}-acetamide is prepared in analogy to Example 55 using 2-amino-propane-1,3-diol; $t_R$=0.78 min, $[M+1]^+$=425.19.

Example 57

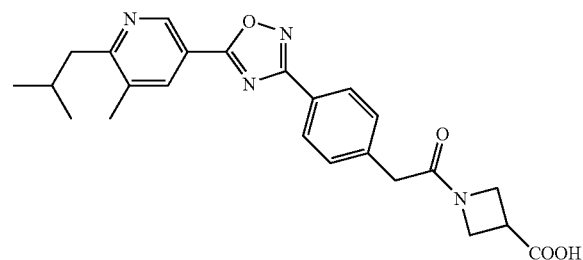

1-(2-{4-[5-(6-Isobutyl-5-methyl-pyridin-3-yl)-[1,2,4]oxadiazol-3-yl]-phenyl}-acetyl)-azetidine-3-carboxylic acid is prepared from {4-[5-(6-Isobutyl-5-methyl-pyridin-3-yl)-[1,2,4]oxadiazol-3-yl]-phenyl}-acetic acid and azetidine-3-carboxylic acid methyl ester in analogy to Example 55; stirring this material in 3 N aq. NaOH/dioxane at rt for 20 h gives the desired compound; LC-MS: $t_R$=0.60, $[M+1]^+$=434.96.

Example 58

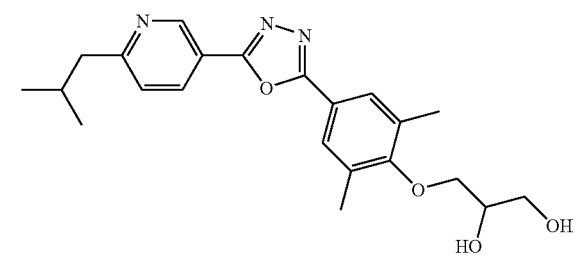

(RS)-3-{4-[5-(6-Isobutyl-pyridin-3-yl)-[1,3,4]oxadiazol-2-yl]-2,6-dimethyl-phenoxy}-propane-1,2-diol is prepared in analogy to Example 28 starting from Nicotinic acid 8; LC-MS: $t_R$=0.85, $[M+1]^+$=398.36.

Example 59

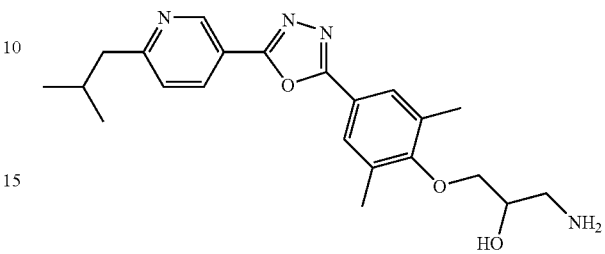

(RS)-1-Amino-3-{4-[5-(6-isobutyl-pyridin-3-yl)-[1,3,4]oxadiazol-2-yl]-2,6-dimethyl-phenoxy}-propan-2-ol is prepared from Example 58 in analogy to Example 2; LC-MS: $t_R$=0.75, $[M+1]^+$=397.29.

Example 60

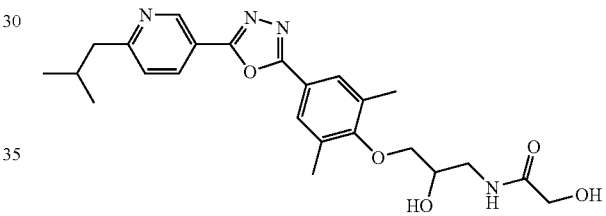

(RS)-2-Hydroxy-N-(2-hydroxy-3-{4-[5-(6-isobutyl-pyridin-3-yl)-[1,3,4]oxadiazol-2-yl]-2,6-dimethyl-phenoxy}-propyl)-acetamide is prepared from Example 59 in analogy to Example 3; LC-MS: $t_R$=0.80, $[M+1]^+$=455.19; $^1$H NMR (CD$_3$OD): δ0.97 (d, J=6.7 Hz, 6H), 2.06-2.20 (m, 1H), 2.38 (s, 6H), 2.76 (d, J=7.0 Hz, 2H), 3.38-3.57 (m, 1H), 3.59-3.73 (m, 1 H), 3.78-3.94 (m, 2H), 4.01 (s, 2H), 4.05-4.16 (m, 1H), 7.50 (d, J=7.9 Hz, 1H), 7.81 (s, 2H), 8.41 (dd, J=8.2, 2.1 Hz, 1H), 9.16 (d, J=2.1 Hz, 1H).

Examples 61 to 70

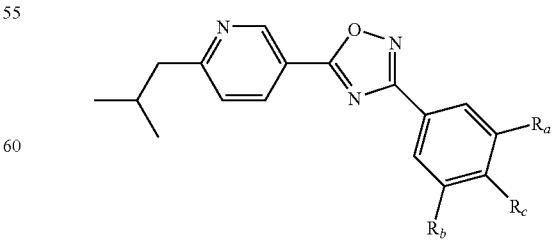

The following examples are prepared in analogy to previous examples starting from nicotinic acid 8.

| Example | in analogy to Example | $R_a$ | $R_b$ | $R_c$ | LC-MS $t_R$ [min] | $[M+H]^+$ |
|---|---|---|---|---|---|---|
| 61 | 13 | CH₃ | CH₃ | OH | 1.04 | 324.36 |
| 62 | 13 | OCH₃ | Cl | OH | 1.03 | 360.01 |
| 63 | 17 | CH₂CH₃ | CH₃ | 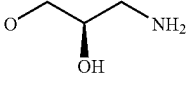 | 0.81 | 411.47 |
| 64 | 17 | CH₂CH₃ | CH₃ | 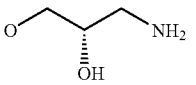 | 0.81 | 411.41 |
| 65 | 18 | CH₂CH₃ | CH₃ | 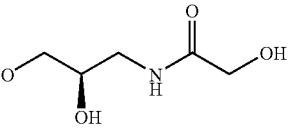 | 0.92 | 469.25 |
| 66 | 18 | CH₂CH₃ | CH₃ | 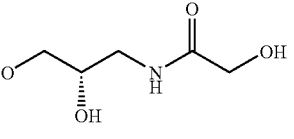 | 0.92 | 469.24 |
| 67 | 17 | OCH₃ | Cl | 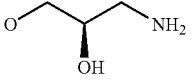 | 0.81 | 433.12 |
| 68 | 17 | OCH₃ | Cl | 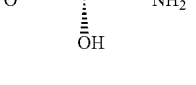 | 0.81 | 433.10 |
| 69 | 18 | OCH₃ | Cl | 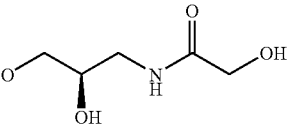 | 0.91 | 491.02 |
| 70 | 18 | OCH₃ | Cl | 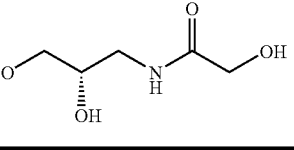 | 0.91 | 491.04 |

Example 66

¹H NMR (CDCl₃): δ0.99 (d, J=6.5 Hz, 6H), 1.33 (t, J=7.5 Hz, 3H), 2.15-2.26 (m, 1H), 2.40 (s, 3H), 2.72-2.83 (m, 4H), 3.49-3.58 (m, 1H), 3.78-3.94 (m, 3H), 4.17-4.26 (m, 3H), 6.98 (s br, 1H), 7.34 (d, J=8.3 Hz, 1H), 7.88 (s, 1H), 7.89 (s, 1H), 8.39 (dd, J=8.0, 2.0 Hz, 1H), 9.37 (d, J=1.3 Hz, 1H).

Example 75

¹H NMR (CDCl₃): δ1.01 (d, J=6.8 Hz, 6H), 1.33 (m, 6H), 2.15 (s br, 1H), 2.22-2.34 (m, 2H), 2.42 (s, 3H), 2.73-2.85 (m, 4H), 3.51 (s, 1H), 3.96-4.09 (m, 5H), 7.89 (s, 1H), 7.92 (s, 1H), 8.25 (d, J=1.8 Hz, 1H), 9.21 (d, J=2.0 Hz, 1H).

Examples 71 to 77

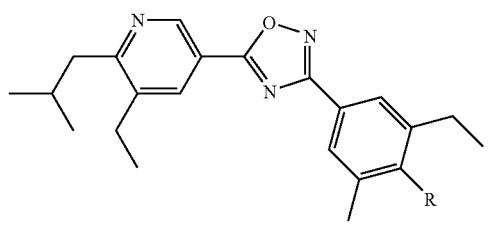

The following examples are prepared from nicotinic acid 9 and 3-ethyl-4,N-dihydroxy-5-methyl-benzamidine in analogy to previous examples.

Examples 78 to 81

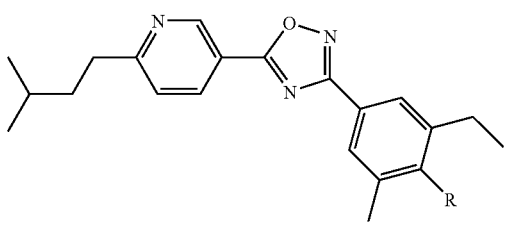

The following examples are prepared from Nicotinic acid 10 and 3-ethyl-4,N-dihydroxy-5-methyl-benzamidine in analogy to previous examples.

| Example | in analogy to Example | R | LC-MS $t_R$ [min] | $[M + H]^+$ |
|---|---|---|---|---|
| 71 | 13 | OH | 1.08 | 366.10 |
| 72 | 16 | O~~OH | 1.06 | 410.15 |
| 73 | 16 | O~~~OH | 1.09 | 424.32 |
| 74 | 14 | O~CH(OH)~CH₂OH | 0.98 | 440.29 |
| 75 | 15 | O~CH(CH₂OH)₂ | 1.01 | 454.37 |
| 76 | 17 | O~CH(OH)~CH₂NH₂ rac | 0.85 | 439.28 |
| 77 | 18 | O~CH(OH)~CH₂NHC(O)CH₂OH rac | 0.94 | 497.36 |

| | in analogy to | | | LC-MS | |
|---|---|---|---|---|---|
| Example | Example | R | | $t_R$ [min] | $[M + H]^+$ |
| 78 | 13 | OH | | 1.05 | 352.52 |
| 79 | 16 |  | | 1.04 | 396.15 |
| 80 | 14 | 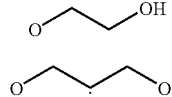 | | 0.96 | 426.11 |
| 81 | 15 | 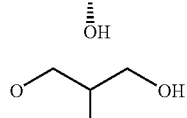 | | 0.99 | 440.24 |
Example 81
$^1$H NMR (CDCl$_3$): δ1.01 (d, J=6.0 Hz, 6H), 1.33 (t, J=7.8 Hz, 3H), 1.67-1.77 (m, 2H), 2.14 (s br, 1H), 2.27-2.35 (m, 1H), 2.42 (s, 3H), 2.77 (q, J=7.5 Hz, 2H), 2.93-2.99 (m, 2H), 3.99-4.09 (m, 5H), 7.86-7.91 (m, 3H), 7.94 (s, 1H), 8.79 (d, J=5.0 Hz, 1H).
Examples 82 to 88
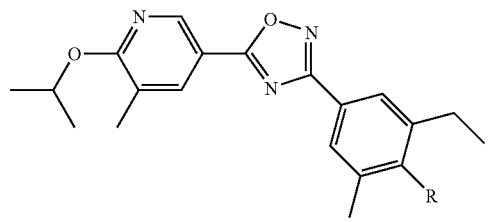
The following examples are prepared in analogy to previous examples starting from Nicotinic acid 11 and 3-ethyl-4,N-dihydroxy-5-methyl-benzamidine.
| | in analogy to | | LC-MS | |
|---|---|---|---|---|
| Example | Example | R | $t_R$ [min] | $[M + H]^+$ |
| 82 | 13 | OH | 1.18 | 354.14 |
| 83 | 14 |  | 1.08 | 428.21 |
| 84 | 14 | 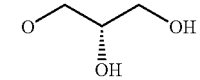 | 1.08 | 428.21 |
| 85 | 17 |  | 0.88 | 427.13 |
| 86 | 17 | 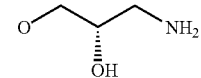 | | |
| 87 | 18 | 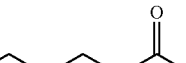 | 1.03 | 485.28 |
| 88 | 18 |  | 1.03 | 485.23 |

Example 88

$^1$H NMR (CDCl$_3$): δ1.32 (t, J=7.5 Hz, 3H), 1.42 (d, J=6.0 Hz, 6H), 2.28 (s, 3H), 2.39 (s, 3H), 2.75 (q, J=7.5 Hz, 2H), 3.41 (m, 1H), 3.48-3.58 (m, 1H), 3.76-3.93 (m, 3H), 4.17-4.25 (m, 3H), 5.43-5.52 (m, 1H), 7.03 (t br, J=4.3 Hz, 1H), 7.85 (s, 1H), 7.87 (s, 1H), 8.14 (s, 1H), 8.84 (s, 1H).

Example 89

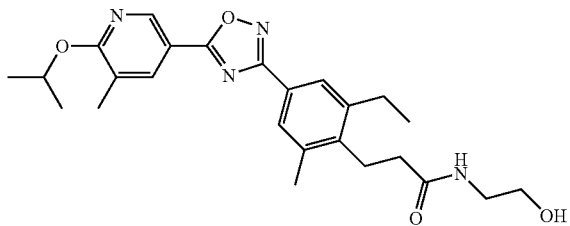

3-{2-Ethyl-4-[5-(6-isopropoxy-5-methyl-pyridin-3-yl)-[1,2,4]oxadiazol-3-yl]-6-methyl-phenyl}-N-(2-hydroxy-ethyl)-propionamide is prepared from 3-{2-ethyl-4-[5-(6-isopropoxy-5-methyl-pyridin-3-yl)-[1,2,4]oxadiazol-3-yl]-6-methyl-phenyl}-propionic acid in analogy to Example 55; LC-MS: t$_R$=1.07, [M+1]$^+$=453.23; $^1$H NMR (CDCl$_3$): δ1.31 (t, J=7.3 Hz, 3H), 1.42 (d, J=5.5 Hz, 6H), 2.28 (s, 3H), 2.38-2.48 (m, 5H), 2.53 (s br, 1H), 2.77 (q, J=7.3 Hz, 2H), 3.06-3.14 (m, 2H), 3.42-3.50 (m, 2H), 3.71-3.79 (m, 2H), 5.42-5.52 (m, 1H), 5.89 (s br, 1H), 7.82 (s, 1H), 7.85 (s, 1H), 8.15 (s, 1H), 8.85 (s, 1H).

Examples 90 to 92

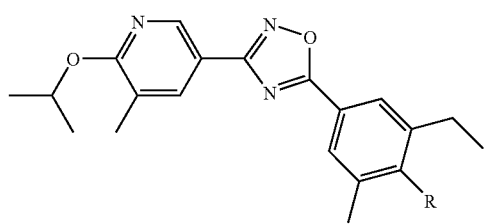

The following examples are prepared in analogy to Example 13 starting from 3-ethyl-4-hydroxy-5-methyl-benzoic acid and N-hydroxy-6-isopropoxy-5-methyl-nicotinamidine.

| Example | in analogy to Example | R | LC-MS t$_R$ [min] | [M + H]$^+$ |
|---|---|---|---|---|
| 90 | 13 | OH | 1.18 | 354.10 |
| 91 | 14 | ![structure with OH, OH] | 1.12 | 428.05 |
| 92 | 14 | ![structure with OH, OH] | 1.12 | 428.06 |

Example 92

$^1$H NMR (CDCl$_3$): δ1.34 (t, J=7.5 Hz, 3H), 1.41 (d, J=6.0 Hz, 6H), 2.03 (t, J=6.0 Hz, 1H), 2.27 (s, 3H), 2.43 (s, 3H), 2.70 (d, J=5.0 Hz, 1H), 2.79 (q, J=7.3 Hz, 2H), 3.82-3.99 (m, 4H), 4.15-4.21 (m, 1H), 5.41-5.49 (m, 1H), 7.92 (s, 1H), 7.96 (s, 1H), 8.11 (s, 1H), 8.79 (s, 1H).

II) Biology

GTPγS Assay to Determine EC$_{50}$ Values

GTPγS binding assays are performed in 96 well microtiter plates (Nunc, 442587) in a final volume of 200 μl, using membrane preparations of CHO cells expressing recombinant human S1P1 receptor. Assay conditions are 20 mM Hepes (Fluka, 54461), 100 mM NaCl (Fluka, 71378), 5 mM MgCl$_2$ (Fluka, 63064), 0.1% BSA (Calbiochem, 126609), 1 μM GDP (Sigma, G-7127), 2.5% DMSO (Fluka, 41644), 50 μM $^{35}$S-GTPγS (Amersham Biosciences, SJ1320). The pH is 7.4. Test compounds are dissolved and diluted in 100% DMSO and pre-incubated at room temperature for 30 min in 150 μl of the above assay buffer, in the absence of $^{35}$S-GTPγS. After addition of 50 μl of $^{35}$S-GTPγS, the assay is incubated for 1 h at rt. The assay is terminated by transfer of the reaction mixture to a Multiscreen plate (Millipore, MAHFC1H60) using a cell harvester from Packard Biosciences, and the plates are washed with ice-cold 10 mM Na$_2$HPO$_4$/NaH$_2$PO$_4$ (70%/30%), dried, sealed at the bottom and, after addition of 25 μl MicroScint20 (Packard Biosciences, order#6013621), sealed on the top. Membrane-bound $^{35}$S-GTPγS is measured with a TopCount from Packard Biosciences.

EC$_{50}$ is the concentration of agonist inducing 50% of the maximal specific $^{35}$S-GTPγS binding. Specific binding is determined by subtracting non-specific binding from maximal binding. Maximal binding is the amount of cpm bound to the Multiscreen plate in the presence of 10 μM of S1P. Non-specific binding is the amount of binding in the absence of an agonist in the assay.

Agonistic activities (EC$_{50}$ values) of 62 from 92 exemplified compounds have been measured. Measured EC$_{50}$ values are in the range of 0.1 to 9410 nM with an average of 492 nM. Agonistic activities of selected compounds are displayed in Table 1.

TABLE 1

| Compound of Example | EC$_{50}$ [nM] |
|---|---|
| 1 | 0.6 |
| 5 | 2.7 |
| 42 | 0.6 |
| 43 | 4.0 |
| 77 | 1.2 |
| 88 | 0.1 |
| 89 | 3.5 |
| 92 | 5.1 |

Assessment of In Vivo Efficacy

The efficacy of the compounds of Formula (I) is assessed by measuring the circulating lymphocytes after oral administration of 3 to 30 mg/kg of a compound of Formula (I) to normotensive male Wistar rats. The animals are housed in climate-controlled conditions with a 12 h-light/dark cycle, and have free access to normal rat chow and drinking water. Blood is collected before and 3, 6 and 24 h after drug administration. Full blood is subjected to hematology using Advia Hematology system (Bayer Diagnostics, Zurich, Switzerland).

All data are presented as mean±SEM. Statistical analyses are performed by analysis of variance (ANOVA) using Statistica (StatSoft) and the Student-Newman-Keuls procedure for multiple comparisons. The null hypothesis is rejected when p<0.05.

As an example, Table 2 shows the effect on lymphocyte counts 6 h after oral administration of 10 mg/kg of a compound of the present invention to normotensive male Wistar rats as compared to a group of animals treated with vehicle only. Lymphocyte counts 6 h after oral administration have been measured for 6 exemplified compounds and are in the range of −77% to −61% with an average of −68%.

TABLE 2

| Compound of Example | Lymphocyte counts |
|---|---|
| 3 | −71% |
| 8 | −61% |
| 12 | −61% |
| 74 | −77% |
| 84 | −76% |

The invention claimed is:
1. A compound of the Formula (I),

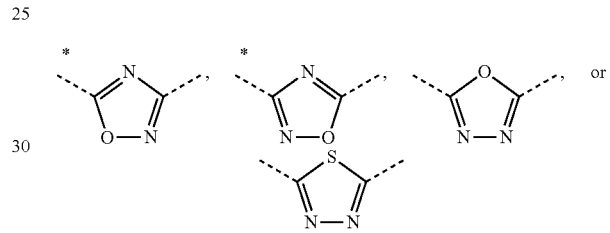

Formula (I)

wherein
A represents

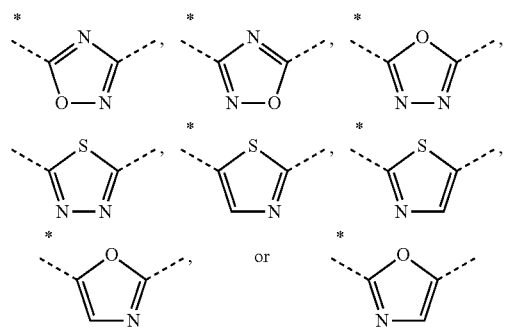

wherein the asterisks indicate the bond that is linked to the pyridine group of Formula (I);
$R^1$ represents hydrogen, $C_{1-4}$-alkyl, or chloro;
$R^2$ represents $C_{1-5}$-alkyl or $C_{1-4}$-alkoxy;
$R^3$ represents hydrogen, $C_{1-4}$-alkyl, $C_{1-4}$-alkoxy, or halogen;
$R^4$ represents hydrogen, $C_{1-4}$-alkyl, $C_{1-4}$-alkoxy, halogen, trifluoromethyl or trifluoromethoxy;
$R^5$ represents 2,3-dihydroxypropyl, di-(hydroxy-$C_{1-4}$-alkyl)-$C_{1-4}$-alkyl, —$CH_2$—$(CH_2)_k$—$NHSO_2R^{53}$, —$(CH_2)$—$CH(OH)$—$CH_2$—$NHSO_2R^{53}$, —$CH_2$—$(CH_2)_k$—$NHCOR^{54}$, —$(CH_2)_n$$CH(OH)$—$CH_2$—$NHCOR^{54}$, —$CH_2$—$(CH_2)_n$—$CONR^{51}R^{52}$, —$(CH_2)_n$—$CH(OH)$—$CH_2$—$NR^{51}R^{52}$, hydroxy, hydroxy-$C_{2-5}$-alkoxy, di-(hydroxy-$C_{1-4}$-alkyl)-$C_{1-4}$-alkoxy, 2,3-dihydroxy-propoxy, 2-hydroxy-3-methoxy-propoxy, —$OCH_2$—$(CH_2)_m$—$NR^{51}R^{52}$, —$OCH_2$—$CH(OH)$—$CH_2$—$NR^{51}R^{52}$, —$OCH_2$—$(CH_2)_m$—$NHSO_2R^{53}$, —$OCH_2$—$CH(OH)$—$CH_2$—$NHSO_2R^{53}$, —$OCH_2$—$(CH_2)_m$—$NHCOR^{54}$, —$OCH_2$—$CH(OH)$—$CH_2$—$NHCOR^{54}$;
$R^{51}$ represents hydrogen, 2-hydroxyethyl, 2-hydroxy-1-hydroxymethyl-ethyl, 2,3-dihydroxypropyl, carboxymethyl, 1-($C_{1-5}$-alkylcarboxy)methyl, 2-carboxyethyl, or 2-($C_{1-5}$-alkylcarboxy)ethyl;
$R^{52}$ represents hydrogen;
$R^{53}$ represents $C_{1-3}$-alkyl, methylamino, ethylamino, or dimethylamino;
$R^{54}$ represents hydroxymethyl, hydroxyethyl, aminomethyl, methylaminomethyl, dimethylaminomethyl, aminoethyl, 2-methylamino-ethyl, or 2-dimethylamino-ethyl;
k represents the integer 1, 2, or 3;
m represents the integer 1 or 2;
n represents 0, 1, or 2; and
$R^6$ represents hydrogen, $C_{1-4}$-alkyl or halogen;
in free or salt form.

2. The compound according to claim 1, wherein A represents

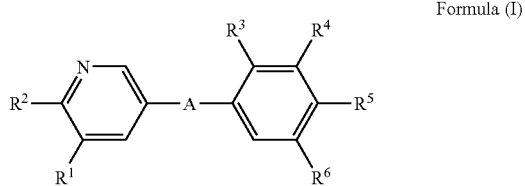

wherein the asterisks indicate the bond that is linked to the pyridine group of Formula (I), in free or salt form.

3. The compound according to claim 1, wherein A represents

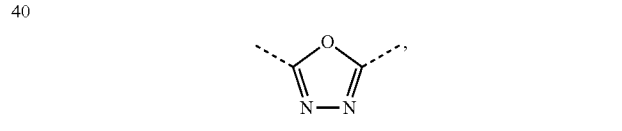

in free or salt form.

4. The compound according to claim 1, wherein $R^1$ represents $C_{1-4}$-alkyl or chloro, in free or salt form.

5. The compound according to claim 1, wherein $R^1$ represents $C_{1-4}$-alkyl, in free or salt form.

6. The compound according to claim 1, wherein $R^2$ represents $C_{1-5}$-alkyl, in free or salt form.

7. The compound according to claim 1, wherein $R^2$ represents n-propyl, or iso-butyl, in free or salt form.

8. The compound according to claim 1, wherein $R^2$ represents $C_{1-4}$-alkoxy, in free or salt form.

9. The compound according to claim 1, wherein $R^3$ represents hydrogen, in free or salt form.

10. The compound according to claim 1, wherein $R^3$ represents hydrogen; and $R^4$ represents $C_{1-4}$-alkyl, or $C_{1-4}$-alkoxy; and $R^6$ represents $C_{1-4}$-alkyl, or halogen, in free or salt form.

11. The compound according to claim 1, wherein $R^3$ represents hydrogen, $R^4$ represents $C_{1-3}$-alkyl, or methoxy, and $R^6$ represents methyl, ethyl, or halogen, in free or salt form.

12. The compound according to claim 1, wherein $R^5$ represents 2,3-dihydroxypropyl, di-(hydroxy-$C_{1-4}$-alkyl)-$C_{1-4}$- alkyl, —CH$_2$—(CH$_2$)$_k$—NHSO$_2$R$^{53}$, —(CH$_2$)—CH(OH)—CH$_2$—NHSO$_2$R$^{53}$, —CH$_2$—(CH$_2$)$_k$—NHCOR$^{54}$, —(CH$_2$)$_n$CH(OH)—CH$_2$—NHCOR$^{54}$, —CH$_2$—(CH$_2$)$_n$—CONR$^{51}$R$^{52}$, —(CH$_2$)$_n$CH(OH)—CH$_2$—NR$^{51}$R$^{52}$, hydroxy, hydroxy-C$_{2-5}$-alkoxy, di-(hydroxy-C$_{1-4}$-alkyl)-C$_{1-4}$-alkoxy, 2,3-dihydroxy-propoxy, 2-hydroxy-3-methoxy-propoxy, —OCH$_2$—(CH$_2$)$_m$—NR$^{51}$R$^{52}$, —OCH$_2$—CH(OH)—CH$_2$—NR$^{51}$R$^{52}$, —OCH$_2$—(CH$_2$)$_m$—NHSO$_2$R$^{53}$, —OCH$_2$—CH(OH)—CH$_2$—NHSO$_2$R$^{53}$, —OCH$_2$—(CH$_2$)$_m$—NHCOR$^{54}$, or —OCH$_2$—CH(OH)—CH$_2$—NHCOR$^{54}$, in free or salt form.

13. The compound according to claim 1, wherein R$^5$ represents 2,3-dihydroxypropyl, —CH$_2$—(CH$_2$)$_k$—NR$^{51}$R$^{52}$, —CH$_2$—(CH$_2$)$_k$—NHCOR$^{54}$, —(CH$_2$)$_n$CH(OH)—CH$_2$—NHCOR$^{54}$, —CH$_2$—(CH$_2$)$_n$—CONR$^{51}$R$^{52}$, —(CH$_2$)$_n$CH(OH)—CH$_2$—NR$^{51}$R$^{52}$, hydroxy-C$_{2-5}$-alkoxy, di-(hydroxy-C$_{1-4}$-alkyl)-C$_{1-4}$-alkoxy, 2,3-dihydroxy-propoxy, 2-hydroxy-3-methoxy-propoxy, —OCH$_2$—(CH$_2$)$_m$—NR$^{51}$R$^{52}$, —OCH$_2$—CH(OH)—CH$_2$—NR$^{51}$R$^{52}$, —OCH$_2$—(CH$_2$)$_m$—NHCOR$^{54}$, or —OCH$_2$—CH(OH)—CH$_2$—NHCOR$^{54}$, in free or salt form.

14. The compound according to claim 1, wherein R$^5$ represents hydroxy-C$_{2-5}$-alkoxy, di-(hydroxy-C$_{1-4}$-alkoxy, 2,3-dihydroxy-propoxy, —OCH$_2$—(CH$_2$)$_m$—NR$^{51}$R$^{52}$, —OCH$_2$—CH(OH)—CH$_2$—NR$^{51}$R$^{52}$, —OCH$_2$—(CH$_2$)$_m$—NHCOR$^{54}$, or —OCH$_2$—CH(OH)—CH$_2$—NHCOR$^{54}$, in free or salt form.

15. The compound according to claim 1, wherein R$^5$ represents 3-hydroxy-2-hydroxymethyl-propoxy, 2,3-dihydroxy-propoxy, or —OCH$_2$—CH(OH)—CH$_2$—NHCOR$^{54}$, in free or salt form.

16. The compound according to claim 1 selected from the group consisting of:
- 3-{4-[5-(5-Chloro-6-isopropoxy-pyridin-3-yl)-[2,4]oxadiazol-3-yl]-2,6-dimethyl-phenoxy}-propane-1,2-diol;
- N-(3-{4-[5-(5-Chloro-6-isopropoxy-pyridin-3-yl)-[1,2,4]oxadiazol-3-yl]-2,6-dimethyl-phenoxy}-2-hydroxy-propyl)-2-hydroxy-acetamide;
- 3-{4-[5-(6-Isobutyl-5-methyl-pyridin-3-yl)-[1,2,4]oxadiazol-3-yl]-2,6-dimethyl-phenoxy}-propane-1,2-diol;
- 2-Hydroxy-N-(2-hydroxy-3-{4-[5-(6-isobutyl-5-methyl-pyridin-3-yl)-[1,2,4]oxadiazol-3-yl]-2,6-dimethyl-phenoxy}-propyl)-acetamide;
- N-(3-{2-Ethyl-4-[5-(6-isobutyl-5-methyl-pyridin-3-yl)-[1,2,4]oxadiazol-3-yl]-6-methyl-phenoxy}-2-hydroxy-propyl)-2-hydroxy-acetamide;
- 3-{4-[5-(5,6-Diisobutyl-pyridin-3-yl)-[2,4]oxadiazol-3-yl]-2,6-dimethyl-phenoxy}-propane-1,2-diol;
- N-(3-{4-[5-(5,6-Diethyl-pyridin-3-yl)-[1,2,4]oxadiazol-3-yl]-2-ethyl-6-methyl-phenoxy}-2-hydroxy-propyl)-2-hydroxy-acetamide;
- 2-Hydroxy-N-(2-hydroxy-3-{4-[5-(6-isobutyl-5-methyl-pyridin-3-yl)-[1,2,4]oxadiazol-3-yl]-3-methyl-phenoxy}-propyl)-acetamide;
- N-(3-{2-Chloro-4-[5-(6-isobutyl-5-methyl-pyridin-3-yl)-[1,2,4]oxadiazol-3-yl]-6-methyl-phenoxy}-2-hydroxy-propyl)-2-hydroxy-acetamide;
- N-(3-{2-Chloro-4-[5-(6-isobutyl-5-methyl-pyridin-3-yl)-[1,2,4]oxadiazol-3-yl]-6-methoxy-phenoxy}-2-hydroxy-propyl)-2-hydroxy-acetamide;
- N—((R)-3-{2-Ethyl-4-[5-(6-isobutyl-5-methyl-pyridin-3-yl)-[1,2,4]oxadiazol-3-yl]-6-methyl-phenoxy}-2-hydroxy-propyl)-2-hydroxy-acetamide;
- N—((S)-3-{2-Ethyl-4-[3-(6-isobutyl-5-methyl-pyridin-3-yl)-[1,2,4]oxadiazol-5-yl]-6-methyl-phenoxy}-2-hydroxy-propyl)-2-hydroxy-acetamide;
- N—((S)-3-{2-Ethyl-4-[5-(6-isobutyl-pyridin-3-yl)-[1,2,4]oxadiazol-3-yl]-6-methyl-phenoxy}-2-hydroxy-propyl)-2-hydroxy-acetamide;
- (S)-3-{2-Ethyl-4-[5-(5-ethyl-6-isobutyl-pyridin-3-yl)-[1,2,4]oxadiazol-3-yl]-6-methyl-phenoxy}-propane-1,2-diol;
- N-(3-{2-Ethyl-4-[5-(5-ethyl-6-isobutyl-pyridin-3-yl)-[1,2,4]oxadiazol-3-yl]-6-methyl-phenoxy}-2-hydroxy-propyl)-2-hydroxy-acetamide;
- (R)-3-{2-Ethyl-4-[5-(6-isopropoxy-5-methyl-pyridin-3-yl)-[1,2,4]oxadiazol-3-yl]-6-methyl-phenoxy}-propane-1,2-diol;
- (S)-3-{2-Ethyl-4-[5-(6-isopropoxy-5-methyl-pyridin-3-yl)-[1,2,4]oxadiazol-3-yl]-6-methyl-phenoxy}-propane-1,2-diol;
- N—((R)-3-{2-Ethyl-4-[5-(6-isopropoxy-5-methyl-pyridin-3-yl)-[1,2,4]oxadiazol-3-yl]-6-methyl-phenoxy}-2-hydroxy-propyl)-2-hydroxy-acetamide;
- N—((S)-3-{2-Ethyl-4-[5-(6-isopropoxy-5-methyl-pyridin-3-yl)-[1,2,4]oxadiazol-3-yl]-6-methyl-phenoxy}-2-hydroxy-propyl)-2-hydroxy-acetamide;
- 3-{2-Ethyl-4-[5-(6-isopropoxy-5-methyl-pyridin-3-yl)-[1,2,4]oxadiazol-3-yl]-6-methyl-phenyl}-N-(2-hydroxy-ethyl)-propionamide;
- (R)-3-{2-Ethyl-4-[3-(6-isopropoxy-5-methyl-pyridin-3-yl)-[1,2,4]oxadiazol-5-yl]-6-methyl-phenoxy}-propane-1,2-diol;
- (S)-3-{2-Ethyl-4-[3-(6-isopropoxy-5-methyl-pyridin-3-yl)-[1,2,4]oxadiazol-5-yl]-6-methyl-phenoxy}-propane-1,2-diol; and
- 3-{2-Ethyl-4-[5-(6-isopropoxy-5-methyl-pyridin-3-yl)-[1,2,4]oxadiazol-3-yl]-6-methyl-phenyl}-propionic acid, in free or salt form.

17. A pharmaceutical composition comprising a compound according to claim 1, in free or pharmaceutically acceptable salt form, and a pharmaceutically acceptable carrier.

* * * * *